United States Patent
Baillie

(10) Patent No.: US 9,981,005 B2
(45) Date of Patent: May 29, 2018

(54) METHODS FOR INCREASING DISC1 IN A SUBJECT WITH SCHIZOPHRENIA OR BIPOLAR DISORDER BY AN ANTAGONIST INHIBITING DISC1 BINDING TO FBXW7

(71) Applicant: The University Court of the University of Glasgow, Glasgow (GB)

(72) Inventor: George Baillie, Glasgow (GB)

(*) Notice: Subject to any disclaimer, the term of this patent is extended or adjusted under 35 U.S.C. 154(b) by 0 days. days.

(21) Appl. No.: 15/025,273

(22) PCT Filed: Sep. 29, 2014

(86) PCT No.: PCT/GB2014/052927
§ 371 (c)(1),
(2) Date: Mar. 26, 2016

(87) PCT Pub. No.: WO2015/044679
PCT Pub. Date: Apr. 2, 2015

(65) Prior Publication Data
US 2016/0206679 A1    Jul. 21, 2016

(30) Foreign Application Priority Data

Sep. 27, 2013 (GB) .................................. 1317207.7

(51) Int. Cl.
| | |
|---|---|
| A61K 38/00 | (2006.01) |
| A61K 38/04 | (2006.01) |
| A61K 38/16 | (2006.01) |
| C07K 14/00 | (2006.01) |
| A61K 38/08 | (2006.01) |
| G01N 33/566 | (2006.01) |
| G01N 33/68 | (2006.01) |

(52) U.S. Cl.
CPC ........... *A61K 38/08* (2013.01); *G01N 33/566* (2013.01); *G01N 33/6896* (2013.01); *G01N 2333/47* (2013.01); *G01N 2500/02* (2013.01); *G01N 2800/28* (2013.01); *G01N 2800/2814* (2013.01); *G01N 2800/30* (2013.01); *G01N 2800/52* (2013.01)

(58) Field of Classification Search
CPC ............ C12Q 1/6883; A01K 2227/105; A01K 2267/0312; A01K 2267/0318; A61K 38/16; A61K 48/00; G01N 2333/47; G01N 2800/28; G01N 33/566; G01N 33/6896
See application file for complete search history.

(56) References Cited

U.S. PATENT DOCUMENTS

| 8,263,547 B2 * | 9/2012 | Tsai | ........................ | A61K 31/00 435/4 |
| 2010/0015130 A1 * | 1/2010 | Tsai | ........................ | A61K 31/00 514/1.1 |
| 2013/0004517 A1 * | 1/2013 | Tsai | ........................ | A61K 31/00 424/172.1 |

FOREIGN PATENT DOCUMENTS

| EP | 0120694 A | 10/1984 | |
| EP | 0125023 A | 11/1984 | |
| WO | WO93/011161 | 6/1993 | |
| WO | WO94/13804 | 6/1994 | |
| WO | WO03/102587 | 12/2003 | |
| WO | WO 2009154697 A2 * | 12/2009 | ............ A61K 31/00 |
| WO | WO2012/139732 | 10/2012 | |
| WO | WO2012139732 | * 10/2012 | |

OTHER PUBLICATIONS

Bowie et al. Science, 1990, 247:1306-1310.*
Pawson et al. 2003, Science 300:445-452.*
Burgess et al. J of Cell Bio. 1990, 111:2129-2138.*
Egleton and Davis (2005) Development of Neuropeptide Drugs that Cross the Blood-Brain Barrier. NeuroRx, vol. 2(1):44-53.
Gabathuler, R. (2010) Approaches to transport therapeutic drugs across the blood-brain barrier to treat brain diseases. Neurobiology of Disease 37:48-57.
Blackwood, D.H., et al., (2001) Schizophrenia and Affective Disorders; Am J Hum Genet, 69(2): p. 428-33.
Bodor, D.L. et al., (2012) Analysis of Protein Turnover by Quantitative SNAP-Based Pulse-Chase Imaging. Current Protocols in Cell Biology (Supp. 55), 8.8.1-8.8.34.
Bradshaw, N.J., et al., PKA Phosphorylation of NDE1 is DISC1/PDE4 Dependent and Modulates its Interaction with LIS1 and NDEL1. J Neurosci, (2011) 31(24):9043-54.
Brandon, N.J. and A. Sawa, (2011) Linking neurodevelopmental and synaptic theories of mental illness through DISC1. Nat Rev Neurosci, 12(12):707-22.
Cajigas, I.J., et al., (2010) Protein homeostasis and synaptic plasticity. EMBO J, 29(16):2746-52.
Camargo, L.M., et al., (2007) Disrupted in Schizophrenia 1 Interactome: evidence for the close connectivity of risk genes and a potential synaptic. Mol Psychiatry, 12(1):74-86.
Carlyle, B.C., et al., (2011) Co-ordinated action of DISC1, PDE4B and GSK3b in modulation of cAMP signalling. Mol Psychiatry. 16(7):693-694.
Crepel, A., et al., (2010) DISC1 duplication in two brothers with autism and mild mental retardation. Clin Genet, 77(4):389-94.
Emsley, P., and Cowtan, K. (2004). Coot: model-building tools for molecular graphics. Acta crystallographica 60:2126-2132.
Esseku and Adeyeye (2011) Bacteria and pH-Sensitive Polysaccharide-Polymer Films for Colon Targeted Delivery. Therapeutic Drug Carrier Systems, 28(5):395-445.

(Continued)

*Primary Examiner* — Chang-Yu Wang
(74) *Attorney, Agent, or Firm* — FisherBroyles, LLP; Victoria L. Boyd

(57) ABSTRACT

The invention relates to the finding that turnover of DISC1 (Disrupted in schizophrenia 1) is mediated by the F-box-containing protein FBXW7 (F-box/WD repeat-containing protein 7). The sequence within DISC1 that binds to FBXW7 and targets DISC1 for turnover by the ubiquitin-proteasome system is identified. The invention provides antagonists that inhibit this interaction and methods of using these antagonists to decrease DISC1 turnover, for example in treatment of neuropsychiatric disorders, as well as methods of identifying new antagonists.

4 Claims, 7 Drawing Sheets

(56) References Cited

OTHER PUBLICATIONS

Eykelenboom, et al., (2012) A t(1;11) translocation linked to schizophrenia and affective disorders gives rise to aberrant chimeric DISC1 . Hum Mol Genet, 21(15):3374-86.
Friedman and Stahl, Biotechnol. Appl. Biochem. (2009) 53: 1-29.
Gebauer and Skerra, Current Op. Chem. Biol. 2009, 13: 245-255.
Hannoun, et al., (2010) Post-translational modification by SUMO. Toxicology 278(3):288-93.
Hanson and Frey, (2008) Intranasal delivery bypasses the blood-brain barrier to target therapeutic agents to the central nervous system. BMC Neuroscience, 9 (Suppl. 3):S5.
Hao, et al., (2007) Structure of a FBXW7-Skpl-cyclin E complex: multisite-phosphorylated substrate recognition by SCF ubiquitin ligases. Mol Cell 26(1):131-143.
Herve, et al., (2008) CNS Delivery Via Adsorptive Transcytosis. The AAPS Journal, 10(3):455-472.
Holliger, et al., Proc. Nat. Acad. Sci. USA 90, 6444-6448, 1993.
Huston, et al., PNAS USA, 85, 5879-5883, 1988.
Ishizuka, et al., (2011) DISC1-dependent switch from progenitor proliferation to migration in the developing cortex. Nature 473(7345):92-6.
Jaaro-Peled, H., (2009) Gene models of schizophrenia: DISC1 mouse models. Prog Brain Res. 179:75-86.
Kamiya, et al., (2012) DISC1 pathway in brain development: exploring therapeutic targets for major psychiatric disorders. Front Psychiatry, 3:25.
Millar, et al., (2005) DISC1 and PDE4B Are Interacting Genetic Factors in Schizophrenia That Regulate cAMP Signaling. Science, 310(5751):1187-91.
Otwinowski and Minor (1997). Processing of X-ray diffraction data collected in oscillation mode. Methods Enzymol. 276:307-326.
Owen, M.J. (2012) Implications of Genetic Findings for Understanding Schizophrenia. Schizophr Bull, 38(5):904-7.
Porteous, et al., (2011) DISC1 at 10: connecting psychiatric genetics and neuroscience. Trends Mol Med, 17(12):699-706.
Schulman, B.A., et al., (2000). Insights into SCF ubiquitin ligases from the structure of the Skp1-Skp2 complex. Nature 408:381-386.
Schurov, et al., (2004) Expression of disrupted in schizophrenia 1 (DISC1) protein in the adult and developing mouse brain indicates . . . Mol Psychiatry, 9(12):1100-10.
Shi, et al., (2012) SNAP-tag Based Proteomics Approach for the Study of the Retrograde Route. Traffic, 13(7):914-25.
Tai and Schuman, (2008) Ubiquitin, the proteasome and protein degradation in neuronal function and dysfunctionNat Rev Neurosci, 9(11):826-38.
Vagin and Teplyakov (2010). Molecular replacement with MOLREP. Acta Crystallographica 66:22-25.
Gordon, et al., (1993) Peptide Azoles: A New Class of Biologically-Active Dipeptide Mimetics. Bioorg. & Med. Chem. Letters 3(5):915-920.
Prokai-Tatrai and Prokai (2009) Prodrugs of Thyrotropin-Releasing Hormone and Related Peptides as Central Nervous System Agents. Molecules 14:633-654.
Williams, et al., (2009) A 1q42 Deletion Involving DISC1, DISC2, and TSNAX in an Autism Spectrum Disorder. Am J Med Genet A, 149A(8):1758-62.
Winn, M.D., et al., (2003). Macromolecular TLS refinement in REFMAC at moderate resolutions. Methods in Enzymology 374:300-321.
International Search Report and Written Opinion for PCT App. No. PCT/GB2014/052927, dated Mar. 3, 2015.
Banks, W.A. (2009) Characteristics of compounds that cross the blood-brain barrier. BMC Neurology 2009, 9(Suppl 1):S3 doi:10.1186/1471-2377-9-S1-S3.
Bord, L., et al., (2006) Primate disrupted-in-schizophrenia-1 (DISC1): High divergence of a gene for major mental illnesses in recent evolution. Neuroscience Res. 56:286-293.

* cited by examiner

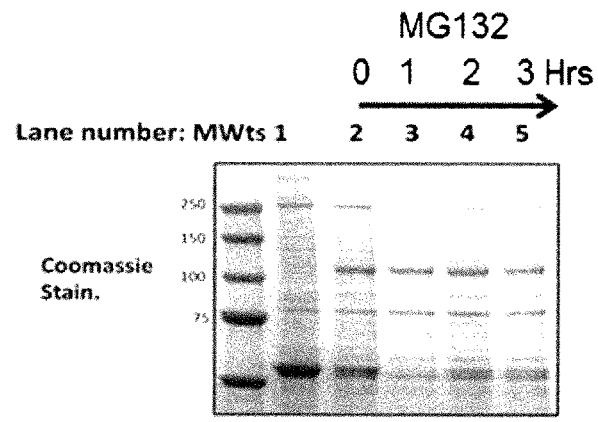
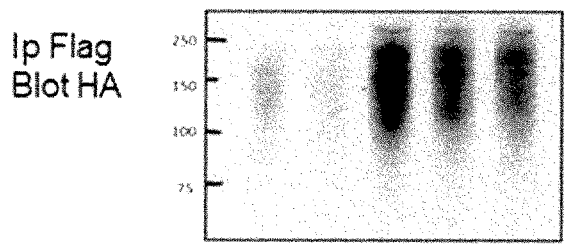
Flag_DISC1 + HA_Ub_2hr_MG132
4.100 No ubiquitination
4.150 $^{360}$LQEDAVENDDYDKAETLQQR$^{379}$ + GlyGly (K) HIGH MASCOT SCORE!
4.200 $^{7}$SLNLSLKEITTK$^{18}$ + 2 GlyGly (K)
4.250 $^{41}$LGSVKEDYNR$^{50}$ + GlyGly (K)
Summary of the peptides in DISC1 that are found to be ubiquitinated by Mass Spectrometry techniques.
Fig. 4

(A)

| | | |
|---|---|---|
| Notch1 | 2119 | HGAPLGG T PTL S PPLCSPNGYLGSL |
| CyclinE | 573 | PLPSGLL T PPQ S GKKQSSGPEMA |
| c-myc | 49 | KKFELLP T PPL S PSRRSGLCSPSYV |
| c-jun | 230 | VPEMPGE T PPL S PIDMESQERIKAE |
| SREBP 1 | 449 | TEVEDTL T PPP S DAGSPFQSSPLSL |
| SV40 large T antigen | 694 | TCFKKPP T PPP E PET |
| Presenilin 1 | 109 | KDGQLIY T PFT E DTETVGQRALHSI |
| Consensus | | φxφφ T PPx S |
| DISC1 | 191 | CGPEVPP T PPG S HSAFTSSFSFIRL |

(B)

| | |
|---|---|
| Human | CGPEVPPTPPGSHSAFTSSFSFIRL |
| Chimp | CGPEAPPTPPDSHSAFTSSFSFIRL |
| Monkey | CGLEDPPTPPGSHSAFASSFSFIRL |
| Dog | SVPKAPPTPAGSQDAFTSSFSFIRL |
| Horse | SGLKFPSAPAGSQDDFTSSFSFIQL |
| Rat | DIP---SLP-GFQDTFTSNFSFIRL |
| Mouse | DIA---SLP-GFQDTFTSSFSFIQL |
| Pufferfish | --SQTAETPP-SQDPEPLIHKKGPN |
| Zebrafish | SDLMKHLTPPESSIVLMNQSETITI |
| Consensus | TPPxS |

Fig. 7

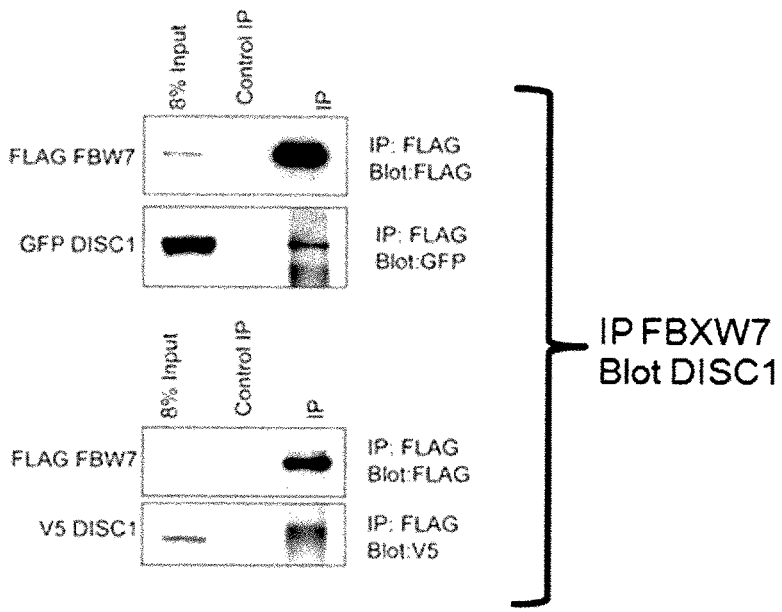

Fig. 8

```
SEQUENCE LISTING

<160> NUMBER OF SEQ ID NOS: 119

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (6)..(6)
<223> OTHER INFORMATION: D-Asp

<400> SEQUENCE: 1

Pro Glu Pro Pro Gly Asp His
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
```

```
<220> FEATURE:
<221> NAME/KEY: MOD_RES
<222> LOCATION: (2)..(2)
<223> OTHER INFORMATION: D-Glu
<220> FEATURE:
<221> NAME/KEY: MOD_RES
<222> LOCATION: (6)..(6)
<223> OTHER INFORMATION: Methylation

<400> SEQUENCE: 2

Pro Glu Pro Pro Gly Glu His
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (6)..(6)
<223> OTHER INFORMATION: Methylation

<400> SEQUENCE: 3

Pro Glu Pro Pro Gly Asp His
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: D-Glu
<220> FEATURE:
<221> NAME/KEY: MOD_RES
<222> LOCATION: (6)..(6)
<223> OTHER INFORMATION: Methylation

<400> SEQUENCE: 4

Pro Glu Pro Pro Gly Asp His
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: D-Asp
<220> FEATURE:
<221> NAME/KEY: MOD_RES
<222> LOCATION: (6)..(6)
<223> OTHER INFORMATION: Methylation

<400> SEQUENCE: 5
```

Pro Asp Pro Pro Gly Glu His
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: Methylation
<220> FEATURE:
<221> NAME/KEY: MOD_RES
<222> LOCATION: (6)..(6)
<223> OTHER INFORMATION: Methylation

<400> SEQUENCE: 6

Gly Glu Pro Pro Gly Glu His
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: Methylation
<220> FEATURE:
<221> NAME/KEY: MOD_RES
<222> LOCATION: (6)..(6)
<223> OTHER INFORMATION: Methylation

<400> SEQUENCE: 7

Gly Asp Pro Pro Gly Glu His
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: D-Glu
<220> FEATURE:
<221> NAME/KEY: MOD_RES
<222> LOCATION: (6)..(6)
<223> OTHER INFORMATION: Methylation

<400> SEQUENCE: 8

Gly Glu Pro Pro Gly Glu His
1               5

<210> SEQ ID NO 9
<211> LENGTH: 7
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: D-Asp
<220> FEATURE:
<221> NAME/KEY: MOD_RES
<222> LOCATION: (6)..(6)
<223> OTHER INFORMATION: Methylation

<400> SEQUENCE: 9

Gly Asp Pro Pro Gly Glu His
1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: Methylation
<220> FEATURE:
<221> NAME/KEY: MOD_RES
<222> LOCATION: (6)..(6)
<223> OTHER INFORMATION: Methylation

<400> SEQUENCE: 10

Gly Glu Pro Pro Gly Glu
1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (1)..(1)
<223> OTHER INFORMATION: Methylation
<220> FEATURE:
<221> NAME/KEY: MOD_RES
<222> LOCATION: (5)..(5)
<223> OTHER INFORMATION: Methylation

<400> SEQUENCE: 11

Glu Pro Pro Gly Glu His
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
```

```
<221> NAME/KEY: MOD_RES
<222> LOCATION: (1)..(1)
<223> OTHER INFORMATION: Methylation
<220> FEATURE:
<221> NAME/KEY: MOD_RES
<222> LOCATION: (5)..(5)
<223> OTHER INFORMATION: Methylation

<400> SEQUENCE: 12

Asp Pro Pro Gly Glu His
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: D-Asp
<220> FEATURE:
<221> NAME/KEY: MOD_RES
<222> LOCATION: (6)..(6)
<223> OTHER INFORMATION: Methylation

<400> SEQUENCE: 13

Gly Asp Pro Pro Gly Glu
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: D-Asp
<220> FEATURE:
<221> NAME/KEY: MOD_RES
<222> LOCATION: (6)..(6)
<223> OTHER INFORMATION: Methylation

<400> SEQUENCE: 14

Gly Asp Pro Pro Gln Glu His
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: D-Asp
<220> FEATURE:
<221> NAME/KEY: MOD_RES
<222> LOCATION: (5)..(5)
<223> OTHER INFORMATION: D-Gln
```

```
<220> FEATURE:
<221> NAME/KEY: MOD_RES
<222> LOCATION: (6)..(6)
<223> OTHER INFORMATION: Methylation

<400> SEQUENCE: 15

Gly Asp Pro Pro Gln Glu His
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: D-Asp
<220> FEATURE:
<221> NAME/KEY: MOD_RES
<222> LOCATION: (6)..(6)
<223> OTHER INFORMATION: Methylation

<400> SEQUENCE: 16

Leu Asp Pro Pro Gly Glu His
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (6)..(6)
<223> OTHER INFORMATION: Methylation

<400> SEQUENCE: 17

Gly Ala Pro Pro Gly Glu His
1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: D-Glu
<220> FEATURE:
<221> NAME/KEY: MOD_RES
<222> LOCATION: (6)..(6)
<223> OTHER INFORMATION: Methylation

<400> SEQUENCE: 18

Gly Glu Pro Pro Gly Glu
1               5
```

```
<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (1)..(1)
<223> OTHER INFORMATION: D-Glu
<220> FEATURE:
<221> NAME/KEY: MOD_RES
<222> LOCATION: (5)..(5)
<223> OTHER INFORMATION: Methylation

<400> SEQUENCE: 19

Glu Pro Pro Gly Glu His
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-Glu
<220> FEATURE:
<221> NAME/KEY: MOD_RES
<222> LOCATION: (6)..(6)
<223> OTHER INFORMATION: Methylation

<400> SEQUENCE: 20

Ala Glu Pro Pro Gly Glu His
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: Phosphorylation
<220> FEATURE:
<221> NAME/KEY: MOD_RES
<222> LOCATION: (6)..(6)
<223> OTHER INFORMATION: Phosphorylation

<400> SEQUENCE: 21

Pro Thr Pro Pro Gly Ser His
1               5

<210> SEQ ID NO 22
<211> LENGTH: 6
<212> TYPE: PRT
```

<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: Methylation
<220> FEATURE:
<221> NAME/KEY: MOD_RES
<222> LOCATION: (6)..(6)
<223> OTHER INFORMATION: Methylation

<400> SEQUENCE: 22

Gly Asp Pro Pro Gly Glu
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: Methylation
<220> FEATURE:
<221> NAME/KEY: MOD_RES
<222> LOCATION: (6)..(6)
<223> OTHER INFORMATION: Methylation

<400> SEQUENCE: 23

Ala Asp Pro Pro Gly Glu His
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: Methylation
<220> FEATURE:
<221> NAME/KEY: MOD_RES
<222> LOCATION: (6)..(6)
<223> OTHER INFORMATION: Methylation

<400> SEQUENCE: 24

Gly Asp Pro Pro Gln Glu His
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic -continued

```
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: Methylation
<220> FEATURE:
<221> NAME/KEY: MOD_RES
<222> LOCATION: (4)..(4)
<223> OTHER INFORMATION: D-Pro
<220> FEATURE:
<221> NAME/KEY: MOD_RES
<222> LOCATION: (6)..(6)
<223> OTHER INFORMATION: Methylation

<400> SEQUENCE: 25

Gly Asp Pro Pro Gly Glu His
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: Methylation
<220> FEATURE:
<221> NAME/KEY: MOD_RES
<222> LOCATION: (6)..(6)
<223> OTHER INFORMATION: Methylation

<400> SEQUENCE: 26

Leu Asp Pro Pro Gly Glu His
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: Methylation
<220> FEATURE:
<221> NAME/KEY: MOD_RES
<222> LOCATION: (6)..(6)
<223> OTHER INFORMATION: Methylation

<400> SEQUENCE: 27

Ala Glu Pro Pro Gly Glu His
1               5

<210> SEQ ID NO 28
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: Methylation
<220> FEATURE:
<221> NAME/KEY: MOD_RES
<222> LOCATION: (5)..(5)
<223> OTHER INFORMATION: D-Gln
<220> FEATURE:
<221> NAME/KEY: MOD_RES
<222> LOCATION: (6)..(6)
<223> OTHER INFORMATION: Methylation

<400> SEQUENCE: 28

Gly Glu Pro Pro Gln Glu His
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: Methylation
<220> FEATURE:
<221> NAME/KEY: MOD_RES
<222> LOCATION: (4)..(4)
<223> OTHER INFORMATION: D-Pro
<220> FEATURE:
<221> NAME/KEY: MOD_RES
<222> LOCATION: (6)..(6)
<223> OTHER INFORMATION: Methylation

<400> SEQUENCE: 29

Gly Glu Pro Pro Gly Glu His
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (1)..(1)
<223> OTHER INFORMATION: D-Leu
<220> FEATURE:
<221> NAME/KEY: MOD_RES
<222> LOCATION: (2)..(2)
<223> OTHER INFORMATION: Methylation
<220> FEATURE:
<221> NAME/KEY: MOD_RES
<222> LOCATION: (6)..(6)
<223> OTHER INFORMATION: Methylation

<400> SEQUENCE: 30

Leu Glu Pro Pro Gly Glu His
1               5
```

```
<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (6)..(6)
<223> OTHER INFORMATION: Methylation

<400> SEQUENCE: 31

Pro Ala Pro Pro Gly Glu His
1               5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: D-Asp
<220> FEATURE:
<221> NAME/KEY: MOD_RES
<222> LOCATION: (6)..(6)
<223> OTHER INFORMATION: Methylation

<400> SEQUENCE: 32

Pro Asp Pro Pro Gly Glu
1               5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (1)..(1)
<223> OTHER INFORMATION: D-Asp
<220> FEATURE:
<221> NAME/KEY: MOD_RES
<222> LOCATION: (5)..(5)
<223> OTHER INFORMATION: Methylation

<400> SEQUENCE: 33

Asp Pro Pro Gly Glu His
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
```

```
<222> LOCATION: (2)..(2)
<223> OTHER INFORMATION: D-Asp
<220> FEATURE:
<221> NAME/KEY: MOD_RES
<222> LOCATION: (3)..(3)
<223> OTHER INFORMATION: D-Pro
<220> FEATURE:
<221> NAME/KEY: MOD_RES
<222> LOCATION: (6)..(6)
<223> OTHER INFORMATION: Methylation

<400> SEQUENCE: 34

Pro Asp Pro Pro Gly Glu His
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: D-Asp
<220> FEATURE:
<221> NAME/KEY: MOD_RES
<222> LOCATION: (6)..(6)
<223> OTHER INFORMATION: Methylation

<400> SEQUENCE: 35

Leu Asp Pro Pro Gly Glu His
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (1)..(1)
<223> OTHER INFORMATION: D-Leu
<220> FEATURE:
<221> NAME/KEY: MOD_RES
<222> LOCATION: (2)..(2)
<223> OTHER INFORMATION: D-Asp
<220> FEATURE:
<221> NAME/KEY: MOD_RES
<222> LOCATION: (6)..(6)
<223> OTHER INFORMATION: Methylation

<400> SEQUENCE: 36

Leu Asp Pro Pro Gly Glu His
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
```

```
<221> NAME/KEY: MOD_RES
<222> LOCATION: (2)..(2)
<223> OTHER INFORMATION: D-Glu
<220> FEATURE:
<221> NAME/KEY: MOD_RES
<222> LOCATION: (6)..(6)
<223> OTHER INFORMATION: Methylation

<400> SEQUENCE: 37

Pro Glu Pro Pro Gly Asp His
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (6)..(6)
<223> OTHER INFORMATION: Methylation

<400> SEQUENCE: 38

Pro Ala Pro Pro Gly Asp His
1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: D-Glu
<220> FEATURE:
<221> NAME/KEY: MOD_RES
<222> LOCATION: (6)..(6)
<223> OTHER INFORMATION: Methylation

<400> SEQUENCE: 39

Pro Glu Pro Pro Gly Glu
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-Glu
<220> FEATURE:
<221> NAME/KEY: MOD_RES
<222> LOCATION: (6)..(6)
<223> OTHER INFORMATION: Methylation
```

```
<400> SEQUENCE: 40

Ala Glu Pro Pro Gly Glu His
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: D-Glu
<220> FEATURE:
<221> NAME/KEY: MOD_RES
<222> LOCATION: (6)..(6)
<223> OTHER INFORMATION: Methylation

<400> SEQUENCE: 41

Pro Glu Pro Pro Gln Glu His
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: D-Glu
<220> FEATURE:
<221> NAME/KEY: MOD_RES
<222> LOCATION: (5)..(5)
<223> OTHER INFORMATION: D-Gln
<220> FEATURE:
<221> NAME/KEY: MOD_RES
<222> LOCATION: (6)..(6)
<223> OTHER INFORMATION: Methylation

<400> SEQUENCE: 42

Pro Glu Pro Pro Gln Glu His
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: D-Glu
<220> FEATURE:
<221> NAME/KEY: MOD_RES
<222> LOCATION: (4)..(4)
<223> OTHER INFORMATION: D-Pro
<220> FEATURE:
<221> NAME/KEY: MOD_RES
<222> LOCATION: (6)..(6)
```

<223> OTHER INFORMATION: Methylation

<400> SEQUENCE: 43

Pro Glu Pro Pro Gly Glu His
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: D-Glu
<220> FEATURE:
<221> NAME/KEY: MOD_RES
<222> LOCATION: (3)..(3)
<223> OTHER INFORMATION: D-Pro
<220> FEATURE:
<221> NAME/KEY: MOD_RES
<222> LOCATION: (6)..(6)
<223> OTHER INFORMATION: Methylation

<400> SEQUENCE: 44

Pro Glu Pro Pro Gly Glu His
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: D-Glu
<220> FEATURE:
<221> NAME/KEY: MOD_RES
<222> LOCATION: (6)..(6)
<223> OTHER INFORMATION: Methylation

<400> SEQUENCE: 45

Leu Glu Pro Pro Gly Glu His
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (1)..(1)
<223> OTHER INFORMATION: D-Leu
<220> FEATURE:
<221> NAME/KEY: MOD_RES
<222> LOCATION: (2)..(2)
<223> OTHER INFORMATION: D-Glu
<220> FEATURE:
<221> NAME/KEY: MOD_RES

```
<222> LOCATION: (6)..(6)
<223> OTHER INFORMATION: Methylation

<400> SEQUENCE: 46

Leu Glu Pro Pro Gly Glu His
1               5

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (6)..(6)
<223> OTHER INFORMATION: Methylation

<400> SEQUENCE: 47

Pro Glu Pro Pro Gly Asp
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (6)..(6)
<223> OTHER INFORMATION: Methylation

<400> SEQUENCE: 48

Pro Glu Pro Pro Gln Asp His
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-Asp
<220> FEATURE:
<221> NAME/KEY: MOD_RES
<222> LOCATION: (4)..(4)
<223> OTHER INFORMATION: D-Pro
<220> FEATURE:
<221> NAME/KEY: MOD_RES
<222> LOCATION: (6)..(6)
<223> OTHER INFORMATION: Methylation

<400> SEQUENCE: 49

Ala Asp Pro Pro Gly Glu His
1               5
```

```
<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-Asp
<220> FEATURE:
<221> NAME/KEY: MOD_RES
<222> LOCATION: (3)..(3)
<223> OTHER INFORMATION: D-Pro
<220> FEATURE:
<221> NAME/KEY: MOD_RES
<222> LOCATION: (6)..(6)
<223> OTHER INFORMATION: Methylation

<400> SEQUENCE: 50

Ala Asp Pro Pro Gly Glu His
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-Asp
<220> FEATURE:
<221> NAME/KEY: MOD_RES
<222> LOCATION: (3)..(4)
<223> OTHER INFORMATION: D-Pro
<220> FEATURE:
<221> NAME/KEY: MOD_RES
<222> LOCATION: (6)..(6)
<223> OTHER INFORMATION: Methylation

<400> SEQUENCE: 51

Ala Asp Pro Pro Gly Glu His
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (1)..(1)
<223> OTHER INFORMATION: D-Ala
```

-continued

```
<220> FEATURE:
<221> NAME/KEY: MOD_RES
<222> LOCATION: (2)..(2)
<223> OTHER INFORMATION: D-Asp
<220> FEATURE:
<221> NAME/KEY: MOD_RES
<222> LOCATION: (6)..(6)
<223> OTHER INFORMATION: Methylation
<220> FEATURE:
<221> NAME/KEY: MOD_RES
<222> LOCATION: (7)..(7)
<223> OTHER INFORMATION: D-His

<400> SEQUENCE: 52

Ala Asp Pro Pro Gly Glu His
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-Asp
<220> FEATURE:
<221> NAME/KEY: MOD_RES
<222> LOCATION: (5)..(5)
<223> OTHER INFORMATION: D-Ala
<220> FEATURE:
<221> NAME/KEY: MOD_RES
<222> LOCATION: (6)..(6)
<223> OTHER INFORMATION: Methylation
<220> FEATURE:
<221> NAME/KEY: MOD_RES
<222> LOCATION: (7)..(7)
<223> OTHER INFORMATION: D-His

<400> SEQUENCE: 53

Ala Asp Pro Pro Ala Glu His
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-Asp
<220> FEATURE:
<221> NAME/KEY: MOD_RES
<222> LOCATION: (5)..(5)
<223> OTHER INFORMATION: D-Ala
<220> FEATURE:
<221> NAME/KEY: MOD_RES
<222> LOCATION: (6)..(6)
```

<223> OTHER INFORMATION: Methylation

<400> SEQUENCE: 54

Ala Asp Pro Pro Ala Glu His
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-Asp
<220> FEATURE:
<221> NAME/KEY: MOD_RES
<222> LOCATION: (4)..(4)
<223> OTHER INFORMATION: D-Pro
<220> FEATURE:
<221> NAME/KEY: MOD_RES
<222> LOCATION: (5)..(5)
<223> OTHER INFORMATION: D-Ala
<220> FEATURE:
<221> NAME/KEY: MOD_RES
<222> LOCATION: (6)..(6)
<223> OTHER INFORMATION: Methylation
<220> FEATURE:
<221> NAME/KEY: MOD_RES
<222> LOCATION: (7)..(7)
<223> OTHER INFORMATION: D-His

<400> SEQUENCE: 55

Ala Asp Pro Pro Ala Glu His
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-Asp
<220> FEATURE:
<221> NAME/KEY: MOD_RES
<222> LOCATION: (3)..(4)
<223> OTHER INFORMATION: D-Pro
<220> FEATURE:
<221> NAME/KEY: MOD_RES
<222> LOCATION: (5)..(5)
<223> OTHER INFORMATION: D-Ala
<220> FEATURE:
<221> NAME/KEY: MOD_RES
<222> LOCATION: (6)..(6)
<223> OTHER INFORMATION: Methylation
<220> FEATURE:
<221> NAME/KEY: MOD_RES

```
<222> LOCATION: (7)..(7)
<223> OTHER INFORMATION: D-His

<400> SEQUENCE: 56

Ala Asp Pro Pro Ala Glu His
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: D-Asp
<220> FEATURE:
<221> NAME/KEY: MOD_RES
<222> LOCATION: (4)..(4)
<223> OTHER INFORMATION: D-Pro
<220> FEATURE:
<221> NAME/KEY: MOD_RES
<222> LOCATION: (5)..(5)
<223> OTHER INFORMATION: D-Ala
<220> FEATURE:
<221> NAME/KEY: MOD_RES
<222> LOCATION: (6)..(6)
<223> OTHER INFORMATION: Methylation

<400> SEQUENCE: 57

Gly Asp Pro Pro Ala Glu His
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: D-Asp
<220> FEATURE:
<221> NAME/KEY: MOD_RES
<222> LOCATION: (4)..(4)
<223> OTHER INFORMATION: D-Pro
<220> FEATURE:
<221> NAME/KEY: MOD_RES
<222> LOCATION: (5)..(5)
<223> OTHER INFORMATION: D-Ala
<220> FEATURE:
<221> NAME/KEY: MOD_RES
<222> LOCATION: (6)..(6)
<223> OTHER INFORMATION: Methylation
<220> FEATURE:
<221> NAME/KEY: MOD_RES
<222> LOCATION: (7)..(7)
<223> OTHER INFORMATION: D-His

<400> SEQUENCE: 58

Gly Asp Pro Pro Ala Glu His
1               5

<210> SEQ ID NO 59
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: D-Asp
<220> FEATURE:
<221> NAME/KEY: MOD_RES
<222> LOCATION: (3)..(4)
<223> OTHER INFORMATION: D-Pro
<220> FEATURE:
<221> NAME/KEY: MOD_RES
<222> LOCATION: (6)..(6)
<223> OTHER INFORMATION: Methylation

<400> SEQUENCE: 59

Gly Asp Pro Pro Gly Glu His
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: D-Asp
<220> FEATURE:
<221> NAME/KEY: MOD_RES
<222> LOCATION: (3)..(4)
<223> OTHER INFORMATION: D-Pro
<220> FEATURE:
<221> NAME/KEY: MOD_RES
<222> LOCATION: (5)..(5)
<223> OTHER INFORMATION: D-Ala
<220> FEATURE:
<221> NAME/KEY: MOD_RES
<222> LOCATION: (6)..(6)
<223> OTHER INFORMATION: Methylation

<400> SEQUENCE: 60

Gly Asp Pro Pro Ala Glu His
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: D-Asp
<220> FEATURE:
<221> NAME/KEY: MOD_RES
<222> LOCATION: (3)..(4)
<223> OTHER INFORMATION: D-Pro
<220> FEATURE:
<221> NAME/KEY: MOD_RES
<222> LOCATION: (6)..(6)
<223> OTHER INFORMATION: Methylation
```

```
<220> FEATURE:
<221> NAME/KEY: MOD_RES
<222> LOCATION: (7)..(7)
<223> OTHER INFORMATION: D-His

<400> SEQUENCE: 61

Gly Asp Pro Pro Gly Glu His
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: D-Asp
<220> FEATURE:
<221> NAME/KEY: MOD_RES
<222> LOCATION: (3)..(4)
<223> OTHER INFORMATION: D-Pro
<220> FEATURE:
<221> NAME/KEY: MOD_RES
<222> LOCATION: (5)..(5)
<223> OTHER INFORMATION: D-Ala
<220> FEATURE:
<221> NAME/KEY: MOD_RES
<222> LOCATION: (6)..(6)
<223> OTHER INFORMATION: Methylation
<220> FEATURE:
<221> NAME/KEY: MOD_RES
<222> LOCATION: (7)..(7)
<223> OTHER INFORMATION: D-His

<400> SEQUENCE: 62

Gly Asp Pro Pro Ala Glu His
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: D-Asp
<220> FEATURE:
<221> NAME/KEY: MOD_RES
<222> LOCATION: (3)..(3)
<223> OTHER INFORMATION: D-Pro
<220> FEATURE:
<221> NAME/KEY: MOD_RES
<222> LOCATION: (6)..(6)
<223> OTHER INFORMATION: Methylation

<400> SEQUENCE: 63

Gly Asp Pro Pro Gly Glu His
1               5

<210> SEQ ID NO 64
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (1)..(1)
<223> OTHER INFORMATION: D-Pro
<220> FEATURE:
<221> NAME/KEY: MOD_RES
<222> LOCATION: (2)..(2)
<223> OTHER INFORMATION: D-Asp
<220> FEATURE:
<221> NAME/KEY: MOD_RES
<222> LOCATION: (6)..(6)
<223> OTHER INFORMATION: Methylation

<400> SEQUENCE: 64

Pro Asp Pro Pro Gly Glu His
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (1)..(1)
<223> OTHER INFORMATION: D-Pro
<220> FEATURE:
<221> NAME/KEY: MOD_RES
<222> LOCATION: (2)..(2)
<223> OTHER INFORMATION: D-Asp
<220> FEATURE:
<221> NAME/KEY: MOD_RES
<222> LOCATION: (6)..(6)
<223> OTHER INFORMATION: Methylation
<220> FEATURE:
<221> NAME/KEY: MOD_RES
<222> LOCATION: (7)..(7)
<223> OTHER INFORMATION: D-His

<400> SEQUENCE: 65

Pro Asp Pro Pro Gly Glu His
1               5

<210> SEQ ID NO 66
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: D-Asp
<220> FEATURE:
<221> NAME/KEY: MOD_RES
<222> LOCATION: (6)..(6)
<223> OTHER INFORMATION: Methylation

<400> SEQUENCE: 66

Gly Asp Pro Pro Gly Glu
1               5
```

```
<210> SEQ ID NO 67
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (1)..(1)
<223> OTHER INFORMATION: D-Asp
<220> FEATURE:
<221> NAME/KEY: MOD_RES
<222> LOCATION: (5)..(5)
<223> OTHER INFORMATION: Methylation

<400> SEQUENCE: 67

Asp Pro Pro Gly Glu His
1               5

<210> SEQ ID NO 68
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (4)..(4)
<223> OTHER INFORMATION: Methylation

<400> SEQUENCE: 68

Pro Pro Gly Glu His
1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: D-Asp
<220> FEATURE:
<221> NAME/KEY: MOD_RES
<222> LOCATION: (6)..(6)
<223> OTHER INFORMATION: Methylation

<400> SEQUENCE: 69

Gly Asp Pro Ala Gly Glu Lys
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
```

```
<221> NAME/KEY: MOD_RES
<222> LOCATION: (2)..(2)
<223> OTHER INFORMATION: D-Asp
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: Methylation
<220> FEATURE:
<221> NAME/KEY: MOD_RES
<222> LOCATION: (7)..(7)
<223> OTHER INFORMATION: D-Lys

<400> SEQUENCE: 70

Gly Asp Pro Ala Gly Glu Lys
1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: D-Asp
<220> FEATURE:
<221> NAME/KEY: MOD_RES
<222> LOCATION: (6)..(6)
<223> OTHER INFORMATION: Methylation

<400> SEQUENCE: 71

Pro Asp Pro Pro Gly Glu Lys
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: D-Asp
<220> FEATURE:
<221> NAME/KEY: MOD_RES
<222> LOCATION: (6)..(6)
<223> OTHER INFORMATION: Methylation
<220> FEATURE:
<221> NAME/KEY: MOD_RES
<222> LOCATION: (7)..(7)
<223> OTHER INFORMATION: D-Lys

<400> SEQUENCE: 72

Pro Asp Pro Pro Gly Glu Lys
1               5

<210> SEQ ID NO 73
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (2)..(2)
<223> OTHER INFORMATION: D-Asp
<220> FEATURE:
<221> NAME/KEY: MOD_RES
<222> LOCATION: (5)..(5)
<223> OTHER INFORMATION: D-Ala
<220> FEATURE:
<221> NAME/KEY: MOD_RES
<222> LOCATION: (6)..(6)
<223> OTHER INFORMATION: Methylation
<220> FEATURE:
<221> NAME/KEY: MOD_RES
<222> LOCATION: (7)..(7)
<223> OTHER INFORMATION: D-Lys

<400> SEQUENCE: 73

Gly Asp Pro Pro Ala Glu Lys
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Core sequence of FBXW7 - binding moiety
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-Asp
<220> FEATURE:
<221> NAME/KEY: MOD_RES
<222> LOCATION: (5)..(5)
<223> OTHER INFORMATION: D-Ala
<220> FEATURE:
<221> NAME/KEY: MOD_RES
<222> LOCATION: (6)..(6)
<223> OTHER INFORMATION: Methylation
<220> FEATURE:
<221> NAME/KEY: MOD_RES
<222> LOCATION: (7)..(7)
<223> OTHER INFORMATION: D-Lys

<400> SEQUENCE: 74

Ala Asp Pro Pro Ala Glu Lys
1               5

<210> SEQ ID NO 75
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Cell penetrating peptide: Penetratin

<400> SEQUENCE: 75

Arg Gln Ile Lys Ile Trp Phe Gln Asn Arg Arg Met Lys Trp Lys Lys
1               5                   10                  15
```

```
<210> SEQ ID NO 76
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Cell penetrating peptide: Amphipathic model
      peptide

<400> SEQUENCE: 76

Lys Leu Ala Leu Lys Leu Ala Leu Lys Ala Leu Lys Ala Ala Leu Lys
1               5                   10                  15

Leu Ala

<210> SEQ ID NO 77
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Cell penetrating peptide: Transportan

<400> SEQUENCE: 77

Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
            20                  25

<210> SEQ ID NO 78
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Cell penetrating peptide: SBP

<400> SEQUENCE: 78

Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25

<210> SEQ ID NO 79
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Cell penetrating peptide: FBP

<400> SEQUENCE: 79

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 80
<211> LENGTH: 13
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Cell penetrating peptide: HIV Tat peptide

<400> SEQUENCE: 80

Gly Arg Lys Lys Arg Arg Gln Arg Arg Pro Pro Gln
1               5                   10

<210> SEQ ID NO 81
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Cell penetrating peptide: Syn-B1

<400> SEQUENCE: 81

Arg Gly Gly Arg Leu Ser Tyr Ser Arg Arg Arg Phe Ser Thr Ser Thr
1               5                   10                  15

Gly Arg

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Cell penetrating peptide: Syn-B3

<400> SEQUENCE: 82

Arg Arg Leu Ser Tyr Ser Arg Arg Arg Phe
1               5                   10

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Cell penetrating peptide

<400> SEQUENCE: 83

Arg Arg Arg Arg Arg Arg Arg
1               5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Cell penetrating peptide

<400> SEQUENCE: 84

Arg Arg Arg Arg Arg Arg Arg Arg Arg
1               5
```

```
<210> SEQ ID NO 85
<211> LENGTH: 20
<212> TYPE: PRT
<213> ORGANISM: Homo sapiens

<400> SEQUENCE: 85

Leu Gln Glu Asp Ala Val Glu Asn Asp Asp Tyr Asp Lys Ala Glu Thr
1               5                   10                  15

Leu Gln Gln Arg
            20

<210> SEQ ID NO 86
<211> LENGTH: 12
<212> TYPE: PRT
<213> ORGANISM: Homo sapiens

<400> SEQUENCE: 86

Ser Leu Asn Leu Ser Leu Lys Glu Ile Thr Thr Lys
1               5                   10

<210> SEQ ID NO 87
<211> LENGTH: 10
<212> TYPE: PRT
<213> ORGANISM: Homo sapiens

<400> SEQUENCE: 87

Leu Gly Ser Val Lys Glu Asp Tyr Asn Arg
1               5                   10

<210> SEQ ID NO 88
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

His Gly Ala Pro Leu Gly Gly Thr Pro Thr Leu Ser Pro Pro Leu Cys
1               5                   10                  15

Ser Pro Asn Gly Tyr Leu Gly Ser Leu
            20                  25

<210> SEQ ID NO 89
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Pro Leu Pro Ser Gly Leu Leu Thr Pro Pro Gln Ser Gly Lys Lys Gln
1               5                   10                  15

Ser Ser Gly Pro Glu Met Ala
            20

<210> SEQ ID NO 90
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90
```

```
Lys Lys Phe Glu Leu Leu Pro Thr Pro Pro Leu Ser Pro Ser Arg Arg
1               5                   10                  15

Ser Gly Leu Cys Ser Pro Ser Tyr Val
            20                  25

<210> SEQ ID NO 91
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Val Pro Glu Met Pro Gly Glu Thr Pro Pro Leu Ser Pro Ile Asp Met
1               5                   10                  15

Glu Ser Gln Glu Arg Ile Lys Ala Glu
            20                  25

<210> SEQ ID NO 92
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Thr Glu Val Glu Asp Thr Leu Thr Pro Pro Ser Asp Ala Gly Ser
1               5                   10                  15

Pro Phe Gln Ser Ser Pro Leu Ser Leu
            20                  25

<210> SEQ ID NO 93
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Thr Cys Phe Lys Lys Pro Pro Thr Pro Pro Glu Pro Glu Thr
1               5                   10                  15

<210> SEQ ID NO 94
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Lys Asp Gly Gln Leu Ile Tyr Thr Pro Phe Thr Glu Asp Thr Glu Thr
1               5                   10                  15

Val Gly Gln Arg Ala Leu His Ser Ile
            20                  25

<210> SEQ ID NO 95
<211> LENGTH: 25
<212> TYPE: PRT
<213> ORGANISM: Homo sapiens

<400> SEQUENCE: 95
```

Cys Gly Pro Glu Val Pro Pro Thr Pro Pro Gly Ser His Ser Ala Phe
1               5                   10                  15

Thr Ser Ser Phe Ser Phe Ile Arg Leu
            20                  25

<210> SEQ ID NO 96
<211> LENGTH: 25
<212> TYPE: PRT
<213> ORGANISM: Pan troglodytes

<400> SEQUENCE: 96

Cys Gly Pro Glu Ala Pro Pro Thr Pro Pro Asp Ser His Ser Ala Phe
1               5                   10                  15

Thr Ser Ser Phe Ser Phe Ile Arg Leu
            20                  25

<210> SEQ ID NO 97
<211> LENGTH: 25
<212> TYPE: PRT
<213> ORGANISM: Macaca mulatta

<400> SEQUENCE: 97

Cys Gly Leu Glu Asp Pro Pro Thr Pro Pro Gly Ser His Ser Ala Phe
1               5                   10                  15

Ala Ser Ser Phe Ser Phe Ile Arg Leu
            20                  25

<210> SEQ ID NO 98
<211> LENGTH: 25
<212> TYPE: PRT
<213> ORGANISM: Canis familiaris

<400> SEQUENCE: 98

Ser Val Pro Lys Ala Pro Pro Thr Pro Ala Gly Ser Gln Asp Ala Phe
1               5                   10                  15

Thr Ser Ser Phe Ser Phe Ile Arg Leu
            20                  25

<210> SEQ ID NO 99
<211> LENGTH: 25
<212> TYPE: PRT
<213> ORGANISM: Equus caballus

<400> SEQUENCE: 99

Ser Gly Leu Lys Phe Pro Ser Ala Pro Ala Gly Ser Gln Asp Asp Phe
1               5                   10                  15

Thr Ser Ser Phe Ser Phe Ile Gln Leu
            20                  25

<210> SEQ ID NO 100
<211> LENGTH: 21
<212> TYPE: PRT
<213> ORGANISM: Rattus norvegicus

<400> SEQUENCE: 100

Asp Ile Pro Ser Leu Pro Gly Phe Gln Asp Thr Phe Thr Ser Asn Phe
1               5                   10                  15

Ser Phe Ile Arg Leu
            20

<210> SEQ ID NO 101

<211> LENGTH: 21
<212> TYPE: PRT
<213> ORGANISM: Mus musculus

<400> SEQUENCE: 101

Asp Ile Ala Ser Leu Pro Gly Phe Gln Asp Thr Phe Thr Ser Ser Phe
1               5                   10                  15

Ser Phe Ile Gln Leu
            20

<210> SEQ ID NO 102
<211> LENGTH: 22
<212> TYPE: PRT
<213> ORGANISM: Unknown
<220> FEATURE:
<223> OTHER INFORMATION: Description of Unknown:
      Pufferfish sequence

<400> SEQUENCE: 102

Ser Gln Thr Ala Glu Thr Pro Pro Ser Gln Asp Pro Glu Pro Leu Ile
1               5                   10                  15

His Lys Lys Gly Pro Asn
            20

<210> SEQ ID NO 103
<211> LENGTH: 25
<212> TYPE: PRT
<213> ORGANISM: Danio rerio

<400> SEQUENCE: 103

Ser Asp Leu Met Lys His Leu Thr Pro Pro Glu Ser Ser Ile Val Leu
1               5                   10                  15

Met Asn Gln Ser Glu Thr Ile Thr Ile
            20                  25

<210> SEQ ID NO 104
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Consensus motif
<220> FEATURE:
<221> NAME/KEY: MOD_RES
<222> LOCATION: (4)..(4)
<223> OTHER INFORMATION: Any amino acid

<400> SEQUENCE: 104

Thr Pro Pro Xaa Ser
1               5

<210> SEQ ID NO 105
<211> LENGTH: 854
<212> TYPE: PRT
<213> ORGANISM: Homo sapiens

<400> SEQUENCE: 105

Met Pro Gly Gly Gly Pro Gln Gly Ala Pro Ala Ala Ala Gly Gly
1               5                   10                  15

Gly Val Ser His Arg Ala Gly Ser Arg Asp Cys Leu Pro Pro Ala Ala
            20                  25                  30

Cys Phe Arg Arg Arg Arg Leu Ala Arg Arg Pro Gly Tyr Met Arg Ser
        35                  40                  45

```
Ser Thr Gly Pro Gly Ile Gly Phe Leu Ser Pro Ala Val Gly Thr Leu
     50                  55                  60

Phe Arg Phe Pro Gly Gly Val Ser Gly Glu Glu Ser His His Ser Glu
 65                  70                  75                  80

Ser Arg Ala Arg Gln Cys Gly Leu Asp Ser Arg Gly Leu Leu Val Arg
                 85                  90                  95

Ser Pro Val Ser Lys Ser Ala Ala Pro Thr Val Thr Ser Val Arg
                100                 105                 110

Gly Thr Ser Ala His Phe Gly Ile Gln Leu Arg Gly Gly Thr Arg Leu
             115                 120                 125

Pro Asp Arg Leu Ser Trp Pro Cys Gly Pro Gly Ser Ala Gly Trp Gln
    130                 135                 140

Gln Glu Phe Ala Ala Met Asp Ser Ser Glu Thr Leu Asp Ala Ser Trp
145                 150                 155                 160

Glu Ala Ala Cys Ser Asp Gly Ala Arg Arg Val Arg Ala Ala Gly Ser
                165                 170                 175

Leu Pro Ser Ala Glu Leu Ser Ser Asn Ser Cys Ser Pro Gly Cys Gly
                180                 185                 190

Pro Glu Val Pro Pro Thr Pro Pro Gly Ser His Ser Ala Phe Thr Ser
            195                 200                 205

Ser Phe Ser Phe Ile Arg Leu Ser Leu Gly Ser Ala Gly Glu Arg Gly
    210                 215                 220

Glu Ala Glu Gly Cys Pro Pro Ser Arg Glu Ala Glu Ser His Cys Gln
225                 230                 235                 240

Ser Pro Gln Glu Met Gly Ala Lys Ala Ala Ser Leu Asp Gly Pro His
                245                 250                 255

Glu Asp Pro Arg Cys Leu Ser Arg Pro Phe Ser Leu Leu Ala Thr Arg
            260                 265                 270

Val Ser Ala Asp Leu Ala Gln Ala Ala Arg Asn Ser Ser Arg Pro Glu
    275                 280                 285

Arg Asp Met His Ser Leu Pro Asp Met Asp Pro Gly Ser Ser Ser Ser
    290                 295                 300

Leu Asp Pro Ser Leu Ala Gly Cys Gly Gly Asp Gly Ser Ser Gly Ser
305                 310                 315                 320

Gly Asp Ala His Ser Trp Asp Thr Leu Leu Arg Lys Trp Glu Pro Val
                325                 330                 335

Leu Arg Asp Cys Leu Leu Arg Asn Arg Arg Gln Met Glu Val Ile Ser
                340                 345                 350

Leu Arg Leu Lys Leu Gln Lys Leu Gln Glu Asp Ala Val Glu Asn Asp
            355                 360                 365

Asp Tyr Asp Lys Ala Glu Thr Leu Gln Gln Arg Leu Glu Asp Leu Glu
    370                 375                 380

Gln Glu Lys Ile Ser Leu His Phe Gln Leu Pro Ser Arg Gln Pro Ala
385                 390                 395                 400

Leu Ser Ser Phe Leu Gly His Leu Ala Ala Gln Val Gln Ala Ala Leu
                405                 410                 415

Arg Arg Gly Ala Thr Gln Gln Ala Ser Gly Asp Asp Thr His Thr Pro
            420                 425                 430

Leu Arg Met Glu Pro Arg Leu Leu Glu Pro Thr Ala Gln Asp Ser Leu
    435                 440                 445

His Val Ser Ile Thr Arg Arg Asp Trp Leu Leu Gln Glu Lys Gln Gln
    450                 455                 460
```

```
Leu Gln Lys Glu Ile Glu Ala Leu Gln Ala Arg Met Phe Val Leu Glu
465                 470                 475                 480

Ala Lys Asp Gln Gln Leu Arg Arg Glu Ile Glu Glu Gln Glu Gln Gln
            485                 490                 495

Leu Gln Trp Gln Gly Cys Asp Leu Thr Pro Leu Val Gly Gln Leu Ser
        500                 505                 510

Leu Gly Gln Leu Gln Glu Val Ser Lys Ala Leu Gln Asp Thr Leu Ala
        515                 520                 525

Ser Ala Gly Gln Ile Pro Phe His Ala Glu Pro Glu Thr Ile Arg
        530                 535                 540

Ser Leu Gln Glu Arg Ile Lys Ser Leu Asn Leu Ser Leu Lys Glu Ile
545                 550                 555                 560

Thr Thr Lys Val Cys Met Ser Glu Lys Phe Cys Ser Thr Leu Arg Lys
                565                 570                 575

Lys Val Asn Asp Ile Glu Thr Gln Leu Pro Ala Leu Leu Glu Ala Lys
                580                 585                 590

Met His Ala Ile Ser Gly Asn His Phe Trp Thr Ala Lys Asp Leu Thr
            595                 600                 605

Glu Glu Ile Arg Ser Leu Thr Ser Glu Arg Glu Gly Leu Glu Gly Leu
        610                 615                 620

Leu Ser Lys Leu Leu Val Leu Ser Ser Arg Asn Val Lys Lys Leu Gly
625                 630                 635                 640

Ser Val Lys Glu Asp Tyr Asn Arg Leu Arg Arg Glu Val Glu His Gln
                645                 650                 655

Glu Thr Ala Tyr Glu Thr Ser Val Lys Glu Asn Thr Met Lys Tyr Met
            660                 665                 670

Glu Thr Leu Lys Asn Lys Leu Cys Ser Cys Lys Cys Pro Leu Leu Gly
        675                 680                 685

Lys Val Trp Glu Ala Asp Leu Glu Ala Cys Arg Leu Leu Ile Gln Ser
        690                 695                 700

Leu Gln Leu Gln Glu Ala Arg Gly Ser Leu Ser Val Glu Asp Glu Arg
705                 710                 715                 720

Gln Met Asp Asp Leu Glu Gly Ala Ala Pro Ile Pro Pro Arg Leu
                725                 730                 735

His Ser Glu Asp Lys Arg Lys Thr Pro Leu Lys Val Leu Glu Glu Trp
            740                 745                 750

Lys Thr His Leu Ile Pro Ser Leu His Cys Ala Gly Gly Glu Gln Lys
        755                 760                 765

Glu Glu Ser Tyr Ile Leu Ser Ala Glu Leu Gly Glu Lys Cys Glu Asp
770                 775                 780

Ile Gly Lys Lys Leu Leu Tyr Leu Glu Asp Gln Leu His Thr Ala Ile
785                 790                 795                 800

His Ser His Asp Glu Asp Leu Ile Gln Ser Leu Arg Arg Glu Leu Gln
                805                 810                 815

Met Val Lys Glu Thr Leu Gln Ala Met Ile Leu Gln Leu Gln Pro Ala
            820                 825                 830

Lys Glu Ala Gly Glu Arg Glu Ala Ala Ala Ser Cys Met Thr Ala Gly
        835                 840                 845

Val His Glu Ala Gln Ala
    850

<210> SEQ ID NO 106
<211> LENGTH: 858
<212> TYPE: PRT
```

-continued

<213> ORGANISM: Pan troglodytes

<400> SEQUENCE: 106

Met Pro Gly Gly Pro Gln Gly Ala Pro Ala Ala Gly Gly Gly
1               5                   10                  15

Gly Val Ser His Arg Ala Gly Ser Arg Asp Cys Leu Pro Pro Ala Ala
            20                  25                  30

Cys Phe Arg Arg Arg Leu Ala Arg Arg Pro Gly Tyr Met Arg Ser
        35                  40                  45

Ser Thr Gly Pro Gly Ile Gly Phe Leu Ser Pro Ala Val Gly Thr Leu
    50                  55                  60

Phe Arg Phe Pro Gly Gly Val Ser Gly Glu Ser His His Ser Glu
65                  70                  75                  80

Ser Arg Ala Arg Gln Cys Gly Leu Asp Ser Arg Gly Leu Leu Val Arg
            85                  90                  95

Asn Pro Val Ser Lys Ser Ala Ala Pro Ala Val Thr Ser Val Arg
            100                 105                 110

Gly Thr Ser Ala His Phe Gly Ile Gln Leu Arg Gly Thr Arg Leu
            115                 120                 125

Pro Asp Arg Leu Ser Trp Pro Cys Gly Pro Gly Asn Ala Gly Trp Gln
    130                 135                 140

Gln Glu Phe Ala Ala Met Asp Ser Ser Glu Ile Leu Asp Ala Ser Trp
145                 150                 155                 160

Glu Ala Ala Cys Ser Gly Gly Ala Arg Arg Val Arg Ala Ala Gly Ser
            165                 170                 175

Leu Pro Ser Ala Glu Leu Ser Ser Asn Ser Cys Ser Pro Gly Cys Gly
            180                 185                 190

Pro Glu Ala Pro Pro Thr Pro Pro Asp Ser His Ser Ala Phe Thr Ser
            195                 200                 205

Ser Phe Ser Phe Ile Arg Leu Ser Leu Gly Ser Ala Gly Glu Arg Gly
    210                 215                 220

Glu Ala Glu Gly Cys Leu Pro Ser Arg Glu Ala Glu Ser His Cys Gln
225                 230                 235                 240

Ser Pro Gln Glu Met Ala Ala Lys Ala Ala Ser Leu Asp Gly Pro His
            245                 250                 255

Glu Asp Pro Arg Cys Leu Ser Arg Pro Phe Ser Leu Leu Ala Thr Arg
            260                 265                 270

Val Ser Ala Asp Leu Ala Gln Ala Ala Arg Asn Ser Ser Arg Pro Glu
    275                 280                 285

Arg Asp Met His Pro Leu Pro Asp Met Asp Pro Gly Ser Ser Ser Ser
290                 295                 300

Leu Asp Pro Ser Leu Ala Gly Cys Gly Gly Asp Gly Ser Ser Ser Ser
305                 310                 315                 320

Gly Asp Ala His Ser Trp Asp Thr Leu Leu Arg Lys Trp Glu Pro Val
            325                 330                 335

Leu Arg Asp Cys Leu Leu Arg Asn Arg Gln Met Glu Val Ile Ser
            340                 345                 350

Leu Arg Leu Lys Leu Gln Lys Leu Gln Glu Asp Ala Val Glu Asn Asp
            355                 360                 365

Asp Tyr Asp Lys Ala Glu Thr Leu Gln Gln Arg Leu Glu Asp Leu Glu
    370                 375                 380

Gln Glu Lys Ile Ser Leu His Phe Gln Leu Pro Ser Arg Gln Pro Ala
385                 390                 395                 400

-continued

Leu Ser Ser Phe Leu Gly His Leu Ala Ala Gln Val Gln Ala Ala Leu
                405                 410                 415

Cys Arg Gly Ala Thr Gln Gln Ala Ser Arg Asp Asp Thr His Thr Ser
            420                 425                 430

Leu Arg Met Glu Pro Arg Leu Leu Glu Pro Thr Ala Gln Asp Ser Leu
        435                 440                 445

His Val Ser Ile Thr Arg Arg Asp Trp Leu Leu Gln Glu Lys Gln Gln
    450                 455                 460

Leu Gln Lys Glu Ile Glu Ala Leu Gln Ala Arg Met Phe Val Leu Glu
465                 470                 475                 480

Ala Lys Asp Gln Gln Leu Arg Arg Glu Ile Glu Glu Gln Glu Gln Gln
                485                 490                 495

Leu Gln Trp Gln Gly Cys Asp Leu Thr Pro Leu Val Gly Gln Leu Ser
            500                 505                 510

Leu Gly Gln Leu Gln Glu Val Ser Lys Ala Leu Gln Asp Thr Leu Ala
        515                 520                 525

Ser Ala Gly Gln Ile Pro Phe His Ala Glu Pro Glu Thr Ile Arg
    530                 535                 540

Ser Leu Gln Glu Arg Ile Lys Ser Leu Asn Leu Ser Leu Lys Glu Ile
545                 550                 555                 560

Thr Thr Lys Val Cys Met Ser Glu Lys Phe Cys Ser Thr Leu Arg Lys
                565                 570                 575

Lys Val Asn Asp Ile Glu Thr Gln Leu Pro Ala Leu Leu Glu Ala Lys
            580                 585                 590

Met His Ala Ile Ser Gly Asn His Phe Trp Thr Ala Lys Asp Leu Thr
        595                 600                 605

Glu Glu Ile Arg Ser Leu Thr Ser Glu Arg Glu Gly Leu Glu Gly Leu
    610                 615                 620

Leu Ser Lys Leu Leu Val Leu Ser Ser Arg Asn Val Lys Lys Leu Gly
625                 630                 635                 640

Ser Val Lys Glu Asp Tyr Asp Arg Leu Arg Arg Glu Val Glu His Gln
                645                 650                 655

Glu Thr Ala Tyr Glu Thr Ser Val Lys Glu Asn Thr Met Lys Tyr Met
            660                 665                 670

Glu Thr Leu Lys Asn Lys Leu Cys Ser Cys Lys Cys Pro Leu Leu Gly
        675                 680                 685

Lys Val Trp Glu Ala Asp Leu Glu Ala Cys Arg Leu Leu Ile Gln Ser
    690                 695                 700

Leu Gln Leu Gln Glu Ala Arg Gly Ser Leu Ser Val Glu Asp Glu Arg
705                 710                 715                 720

Gln Met Asp Asp Leu Glu Gly Ala Val Cys Ile Ala Ala Pro Pro Ile
                725                 730                 735

Pro Pro Arg Leu His Ser Glu Asp Lys Arg Lys Thr Pro Leu Gln Ala
            740                 745                 750

Leu Glu Glu Trp Lys Ala His Leu Ile Pro Ser Leu His Cys Ala Gly
        755                 760                 765

Gly Glu Gln Lys Glu Glu Ser Tyr Ile Leu Ser Ala Glu Leu Gly Glu
    770                 775                 780

Lys Cys Glu Asp Ile Gly Lys Lys Leu Leu Tyr Leu Glu Asp Gln Leu
785                 790                 795                 800

His Thr Ala Ile His Ser His Asp Glu Asp Leu Ile Gln Ser Leu Arg
                805                 810                 815

Arg Glu Leu Gln Met Val Lys Glu Thr Leu Gln Ala Met Ile Leu Gln

```
                  820                 825                 830
Leu Gln Pro Ala Lys Glu Ala Gly Glu Arg Glu Ala Ala Ser Cys
            835                 840                 845
Met Thr Ala Gly Val His Glu Ala Gln Ala
        850                 855

<210> SEQ ID NO 107
<211> LENGTH: 854
<212> TYPE: PRT
<213> ORGANISM: Macacca mulata

<400> SEQUENCE: 107

Met Pro Gly Gly Gly Pro Gln Gly Ala Pro Ala Ala Gly Gly Gly
1               5                   10                  15

Gly Val Gly His Arg Ala Gly Ser Arg Asp Cys Leu Pro Ala Ala
                20                  25                  30

Cys Phe Arg Arg Arg Leu Ala Arg Pro Gly Tyr Met Arg Ser
            35                  40                  45

Ser Thr Gly Pro Gly Ile Gly Phe Leu Ser Pro Ala Val Gly Thr Leu
    50                  55                  60

Phe Arg Val Pro Gly Gly Val Pro Gly Glu Glu Ser His His Ser Glu
65                  70                  75                  80

Ser Lys Thr Arg Glu Cys Gly Leu Asp Ser Arg Gly Leu Leu Val Gly
                85                  90                  95

Ser Pro Val Ser Lys Ser Ala Ala Pro Ala Val Thr Ser Val Arg
                100                 105                 110

Gly Thr Ser Ala His Phe Gly Ile Gln Leu Arg Gly Thr Arg Leu
            115                 120                 125

Pro Asp Arg Leu Ser Arg Leu Cys Gly Pro Gly Asn Ala Gly Trp Gln
130                 135                 140

Gln Glu Phe Ala Ala Met Asp Ser Ser Glu Thr Leu Asp Thr Ser Trp
145                 150                 155                 160

Glu Ala Ala Cys Ser Asp Gly Ala Arg Arg Val Gln Ala Ala Gly Ser
                165                 170                 175

Val Pro Ser Ala Glu Leu Ser Ser Asn Ser Cys Asn Pro Gly Cys Gly
            180                 185                 190

Leu Glu Asp Pro Pro Thr Pro Pro Gly Ser His Ser Ala Phe Ala Ser
        195                 200                 205

Ser Phe Ser Phe Ile Arg Leu Ser Leu Gly Ser Ala Gly Glu Arg Gly
    210                 215                 220

Glu Ala Glu Gly Cys Pro Pro Ser Arg Glu Ala Glu Ser Pro Cys Gln
225                 230                 235                 240

Ser Pro Gln Glu Met Gly Ala Lys Ala Ala Ser Leu Asp Gly Pro His
                245                 250                 255

Lys Asp Pro Arg Cys Leu Ser Arg Pro Phe Ser Leu Leu Ala Thr Gln
            260                 265                 270

Val Ser Glu Asp Leu Ala Gln Ala Ala Gly Asn Ser Ser Arg Pro Glu
        275                 280                 285

Cys Glu Met His Ser Leu Pro Asp Met Asp Ser Gly Ser Ser Ser Ser
    290                 295                 300

Leu Asp Pro Ser Leu Ala Gly Cys Gly Gly Asp Gly Ser Ser Gly Ser
305                 310                 315                 320

Gly Asp Ala His Ser Trp Asp Thr Leu Leu Arg Lys Trp Glu Pro Val
                325                 330                 335
```

```
Leu Arg Asp Cys Leu Leu Arg Asn Arg Arg Gln Met Glu Val Ile Ser
            340                 345                 350
Leu Arg Leu Lys Leu Gln Lys Leu Gln Glu Asp Ala Val Glu Asn Asp
        355                 360                 365
Asp Tyr Asp Lys Ala Glu Thr Leu Gln Gln Arg Leu Glu Asp Leu Glu
    370                 375                 380
Gln Glu Lys Ile Asn Leu His Phe Gln Leu Pro Ser Arg Gln Pro Ala
385                 390                 395                 400
Leu Ser Ser Phe Leu Gly His Leu Ala Ala Gln Val Gln Ala Ala Leu
                405                 410                 415
Arg Arg Gly Ala Thr Gln Gln Ala Ser Gly Asp Asp Thr His Ala Ser
            420                 425                 430
Leu Arg Thr Glu Pro Arg Leu Leu Glu Cys Thr Ala Gln Asp Ser Leu
        435                 440                 445
His Val Ser Ile Thr Arg Arg Asp Trp Leu Leu Gln Glu Lys Gln Gln
    450                 455                 460
Leu Gln Lys Glu Ile Glu Ala Leu Gln Ala Arg Met Ser Val Leu Glu
465                 470                 475                 480
Ala Lys Asp Gln Gln Leu Arg Arg Glu Ile Glu Glu Lys Glu Gln Gln
                485                 490                 495
Leu Arg Trp Gln Gly Cys Asp Leu Thr Pro Leu Val Gly Arg Leu Ser
            500                 505                 510
Leu Gly Gln Leu Arg Glu Val Ser Lys Ala Leu Gln Asp Thr Leu Ala
        515                 520                 525
Ser Ala Gly Gln Ile Pro Phe His Ala Glu Pro Pro Glu Thr Ile Arg
    530                 535                 540
Ser Leu Gln Glu Arg Ile Lys Ser Leu Asn Leu Ser Leu Lys Glu Ile
545                 550                 555                 560
Thr Thr Lys Val Cys Met Ser Glu Lys Phe Cys Ser Thr Leu Arg Lys
                565                 570                 575
Lys Val Asn Asp Ile Glu Thr Gln Leu Pro Ala Leu Leu Glu Ala Lys
            580                 585                 590
Met His Ala Ile Ser Gly Asn His Phe Cys Thr Ala Lys Asp Leu Thr
        595                 600                 605
Glu Glu Ile Arg Ser Leu Thr Ser Glu Arg Glu Gly Leu Glu Gly Leu
    610                 615                 620
Leu Ser Lys Leu Leu Val Leu Ser Ser Arg Asn Val Lys Lys Leu Gly
625                 630                 635                 640
Ser Val Lys Glu Asp Tyr Asp Arg Leu Arg Arg Glu Val Glu His Gln
                645                 650                 655
Glu Thr Ala Tyr Glu Thr Ser Met Lys Glu Asn Thr Met Lys Tyr Met
            660                 665                 670
Glu Thr Leu Lys Asp Lys Leu Cys Ser Cys Lys Cys Pro Leu Leu Gly
        675                 680                 685
Lys Val Trp Glu Ala Asp Leu Glu Ala Cys Arg Leu Leu Met Gln Ser
    690                 695                 700
Leu Gln Leu Gln Glu Ala Arg Gly Ser Leu Ser Val Glu Asp Glu Arg
705                 710                 715                 720
Gln Met Asp Ala Leu Glu Gly Ala Ala Pro Ile Thr Pro Arg Leu
                725                 730                 735
His Ser Glu Asp Lys Arg Lys Thr Pro Leu Gln Ala Leu Glu Glu Trp
            740                 745                 750
Lys Ala His Leu Ile Pro Ser Leu Tyr Cys Ala Gly Gly Glu Gln Lys
```

```
                755                 760                 765
Glu Glu Ser Tyr Ile Leu Ser Ala Glu Leu Gly Glu Lys Cys Glu Asp
    770                 775                 780

Ile Gly Lys Lys Leu Leu Tyr Leu Glu Asp Gln Leu His Thr Ala Ile
785                 790                 795                 800

His Ser His Asp Glu Asp Leu Ile Gln Ser Leu Lys Arg Glu Leu Gln
            805                 810                 815

Met Val Lys Glu Thr Leu Gln Ala Met Ile Leu Gln Leu Gln Pro Ala
        820                 825                 830

Lys Glu Ala Gly Glu Arg Glu Ala Ala Ala Ser Cys Met Thr Ala Gly
            835                 840                 845

Val His Glu Ala Gln Ala
        850

<210> SEQ ID NO 108
<211> LENGTH: 851
<212> TYPE: PRT
<213> ORGANISM: Mus musculus

<400> SEQUENCE: 108

Met Gln Gly Gly Gly Pro Arg Asp Ala Pro Ile His Ser Pro Ser His
1               5                   10                  15

Gly Ala Asp Ser Gly His Gly Leu Pro Pro Ala Val Ala Pro Gln Arg
            20                  25                  30

Arg Arg Leu Thr Arg Arg Pro Gly Tyr Met Arg Ser Thr Ala Gly Ser
        35                  40                  45

Gly Ile Gly Phe Leu Ser Pro Ala Val Gly Met Pro His Pro Ser Ser
    50                  55                  60

Ala Gly Leu Thr Gly Gln Gln Ser Gln His Ser Gln Ser Lys Ala Gly
65                  70                  75                  80

Gln Cys Gly Leu Asp Pro Gly Ser His Cys Gln Ala Ser Leu Val Gly
                85                  90                  95

Lys Pro Phe Leu Lys Ser Ser Leu Val Pro Ala Val Ala Ser Glu Gly
            100                 105                 110

His Leu His Pro Ala Gln Arg Ser Met Arg Lys Arg Pro Val His Phe
        115                 120                 125

Gly Val His Ser Lys Asn Asp Ser Arg Gln Ser Glu Lys Leu Thr Gly
    130                 135                 140

Ser Phe Lys Pro Gly Asp Ser Gly Cys Trp Gln Glu Leu Leu Ser Ser
145                 150                 155                 160

Asp Ser Phe Lys Ser Leu Ala Pro Ser Leu Asp Ala Pro Trp Asn Thr
                165                 170                 175

Gly Ser Arg Gly Leu Lys Thr Val Lys Pro Leu Ala Ser Ser Ala Leu
            180                 185                 190

Asn Gly Pro Ala Asp Ile Pro Ser Leu Pro Gly Phe Gln Asp Thr Phe
        195                 200                 205

Thr Ser Ser Phe Ser Phe Ile Gln Leu Ser Leu Gly Ala Ala Gly Glu
    210                 215                 220

Arg Gly Glu Ala Glu Gly Cys Leu Pro Ser Arg Glu Ala Glu Pro Leu
225                 230                 235                 240

His Gln Arg Pro Gln Glu Met Ala Ala Glu Ala Ser Ser Ser Asp Arg
                245                 250                 255

Pro His Gly Asp Pro Arg His Leu Trp Thr Phe Ser Leu His Ala Ala
            260                 265                 270
```

```
Pro Gly Leu Ala Asp Leu Ala Gln Val Thr Arg Ser Ser Arg Gln
            275                 280                 285

Pro Glu Cys Gly Thr Val Ser Ser Ser Asp Thr Val Phe Ser Ser
290                 295                 300

Gln Asp Ala Ser Ser Ala Gly Gly Arg Gly Asp Gln Gly Gly Gly Trp
305                 310                 315                 320

Ala Asp Ala His Gly Trp His Thr Leu Leu Arg Glu Trp Glu Pro Met
                325                 330                 335

Leu Gln Asp Tyr Leu Leu Ser Asn Arg Arg Gln Leu Glu Val Thr Ser
            340                 345                 350

Leu Ile Leu Lys Leu Gln Lys Cys Gln Glu Lys Ala Val Glu Asp Gly
            355                 360                 365

Asp Tyr Asp Thr Ala Glu Thr Leu Arg Gln Arg Leu Glu Glu Leu Glu
370                 375                 380

Gln Glu Lys Gly His Leu Ser Trp Ala Leu Pro Ser Gln Gln Pro Ala
385                 390                 395                 400

Leu Arg Ser Phe Leu Gly Tyr Leu Ala Ala Gln Ile Gln Val Ala Leu
                405                 410                 415

His Gly Ala Thr Gln Arg Ala Gly Ser Asp Asp Pro Glu Ala Pro Leu
            420                 425                 430

Glu Gly Gln Leu Arg Thr Thr Ala Gln Asp Ser Leu Pro Ala Ser Ile
            435                 440                 445

Thr Arg Arg Asp Trp Leu Ile Arg Glu Lys Gln Gln Leu Gln Lys Glu
450                 455                 460

Ile Glu Ala Leu Gln Ala Arg Met Ser Ala Leu Glu Ala Lys Glu Lys
465                 470                 475                 480

Arg Leu Ser Gln Glu Leu Glu Glu Gln Glu Val Leu Leu Arg Trp Pro
                485                 490                 495

Gly Cys Asp Leu Met Ala Leu Val Ala Gln Met Ser Pro Gly Gln Leu
            500                 505                 510

Gln Glu Val Ser Lys Ala Leu Gly Glu Thr Leu Thr Ser Ala Asn Gln
            515                 520                 525

Ala Pro Phe His Val Glu Pro Pro Glu Thr Leu Arg Ser Leu Arg Glu
530                 535                 540

Arg Thr Lys Ser Leu Asn Leu Ala Val Arg Glu Leu Thr Ala Gln Val
545                 550                 555                 560

Cys Ser Gly Glu Lys Leu Cys Ser Ser Leu Arg Arg Arg Leu Ser Asp
                565                 570                 575

Leu Asp Thr Arg Leu Pro Ala Leu Leu Glu Ala Lys Met Leu Ala Leu
            580                 585                 590

Ser Gly Ser Cys Phe Ser Thr Ala Lys Glu Leu Thr Glu Glu Ile Trp
            595                 600                 605

Ala Leu Ser Ser Glu Arg Glu Gly Leu Glu Met Phe Leu Gly Arg Leu
610                 615                 620

Leu Ala Leu Ser Ser Arg Asn Ser Arg Arg Leu Gly Ile Leu Lys Glu
625                 630                 635                 640

Asp Tyr Leu Arg Cys Arg Gln Asp Leu Ala Leu Gln Asp Ala Ala His
                645                 650                 655

Lys Thr Arg Met Lys Ala Asn Thr Val Lys Cys Met Glu Val Leu Glu
            660                 665                 670

Gly Gln Leu Ser Ser Cys Arg Cys Pro Leu Leu Gly Arg Val Trp Lys
            675                 680                 685

Ala Asp Leu Glu Thr Cys Gln Leu Leu Met Gln Ser Leu Gln Leu Gln
```

```
                    690                 695                 700
Glu Ala Gly Ser Ser Pro His Ala Glu Asp Glu Gln Val His Ser
705                 710                 715                 720

Thr Gly Glu Ala Ala Gln Thr Ala Ala Leu Ala Val Pro Arg Thr Pro
                    725                 730                 735

His Pro Glu Glu Glu Lys Ser Pro Leu Gln Val Leu Gln Glu Trp Asp
                740                 745                 750

Thr His Ser Ala Leu Ser Pro His Cys Ala Ala Gly Pro Trp Lys Glu
                755                 760                 765

Asp Ser His Ile Val Ser Ala Glu Val Gly Glu Lys Cys Glu Ala Ile
            770                 775                 780

Gly Val Arg Leu Leu His Leu Glu Asp Gln Leu Leu Gly Ala Met Tyr
785                 790                 795                 800

Ser His Asp Glu Ala Leu Phe Gln Ser Leu Gln Gly Glu Leu Gln Thr
                805                 810                 815

Val Lys Glu Thr Leu Gln Ala Met Ile Leu Gln Leu Gln Pro Thr Lys
                820                 825                 830

Glu Ala Gly Glu Ala Ser Ala Ser Tyr Pro Thr Ala Gly Ala Gln Glu
            835                 840                 845

Thr Glu Ala
    850

<210> SEQ ID NO 109
<211> LENGTH: 824
<212> TYPE: PRT
<213> ORGANISM: Rattus norvegicus

<400> SEQUENCE: 109

Met Gln Gly Ala Gly Ser Arg Gly Ala Trp Ile His Ser Pro Ser His
1               5                   10                  15

Cys Pro Gly Asn Gly His Gly Ser Pro Pro Ala Val Ala Pro Gln Arg
                20                  25                  30

Arg Arg Leu Thr Arg Arg Pro Gly Tyr Met Arg Ser Thr Ala Ser Pro
            35                  40                  45

Gly Ile Gly Phe Leu Ser Pro Ala Val Gly Met Pro Arg Pro Ile Ser
        50                  55                  60

Ala Gly Leu Thr Gly Gln Glu Phe Tyr Pro Ser Gln Ser Lys Ala Arg
65                  70                  75                  80

Gln Cys Ser Leu Asp Leu Arg Ser His Cys Gln Asp Ser Leu Val Gly
                85                  90                  95

Asn Pro Phe Leu Lys Gly Ser Leu Gly Pro Ala Val Thr Ser Val Gly
                100                 105                 110

His Leu His Pro Ala Gln Gly Ser Met Arg Glu Arg Met Val His Ser
            115                 120                 125

Gly Val His Ser Gly Asn Asp Arg Arg Gln Ser Glu Arg Leu Thr Gly
        130                 135                 140

Asp Ser Gly Cys Arg Gln Glu Phe Leu Ser Ser Asp Ser Ser Lys Ser
145                 150                 155                 160

Leu Ala Ser Ser Leu Asp Val Ala Trp Ser Lys Gly Ser Arg Gly Leu
                165                 170                 175

Lys Thr Val Arg Pro Leu Val Ser Pro Ala Ser Asn Gly Pro Val Asp
                180                 185                 190

Ile Pro Ser Leu Pro Gly Phe Gln Asp Thr Phe Thr Ser Asn Phe Ser
            195                 200                 205
```

-continued

```
Phe Ile Arg Leu Ser Leu Gly Ala Ala Gly Glu Arg Gly Glu Ala Glu
    210                 215                 220
Gly Cys Leu Pro Ser Arg Glu Ala Glu Pro Leu His Gln Ser Pro Gln
225                 230                 235                 240
Glu Met Ala Ala Glu Gly Ser Gly Ser Asp Arg Pro His Gly Glu Pro
                245                 250                 255
Arg His Leu Trp Thr Phe Ser Leu His Ala Ala Pro Gly Leu Val Asp
            260                 265                 270
Leu Ala Gln Gly Thr Arg Ser Asn Arg Gln Pro Glu Cys Gly Met Val
        275                 280                 285
Ser Ser Ser Asp Ala Gly Phe Ser Ser Gln Asp Ala Ser Pro Ala Gly
290                 295                 300
Gly Arg Ser Asp Gln Asp Gly Gly Trp Ala Asp Ala His Gly Trp His
305                 310                 315                 320
Ala Leu Leu Arg Glu Trp Glu Pro Met Leu Gln Asp Tyr Leu Leu Ser
                325                 330                 335
Asn Arg Arg Gln Leu Glu Val Thr Ser Leu Ile Leu Lys Leu Gln Lys
            340                 345                 350
Leu Gln Glu Lys Ala Val Glu Asp Gly Asp Tyr Asp Met Ala Glu Thr
        355                 360                 365
Leu Arg Gln Arg Leu Glu Asp Leu Glu Gln Glu Lys Gly Arg Leu Pro
370                 375                 380
Trp Ala Leu Pro Ser Gln Gln Pro Ala Leu Arg Ser Phe Leu Gly Tyr
385                 390                 395                 400
Leu Ala Thr Gln Thr His Ala Ala Leu His Gly Ala Pro Gln Arg Ala
                405                 410                 415
Gly Ser Asp Asp Pro Glu Ala Pro Leu Glu Gly Gln Arg Arg Thr Thr
            420                 425                 430
Ala Gln Asp Ser Leu Pro Gly Leu Ala Val Thr Arg Arg Asp Trp Leu
        435                 440                 445
Met Arg Glu Lys Glu Gln Leu Gln Lys Gly Ile Glu Ala Leu Arg Ala
450                 455                 460
Arg Val Ser Val Leu Glu Ala Lys Glu Gln Arg Leu Ser Gln Glu Leu
465                 470                 475                 480
Glu Asp Gln Glu Met Leu Leu Arg Trp Gln Gly Cys Asp Gln Met Ala
                485                 490                 495
Leu Val Ala Gln Leu Ser Pro Gly Gln Leu Gln Glu Val Ser Lys Ala
            500                 505                 510
Leu Gly Glu Thr Leu Thr Ser Ala Arg Trp Ala Pro Phe Arg Val Glu
        515                 520                 525
Pro Pro Glu Thr Leu Arg Ser Leu Arg Glu Arg Thr Lys Ser Leu Asp
530                 535                 540
Leu Ala Val Arg Glu Leu Thr Glu Gln Val Cys Ser Gly Glu Lys Leu
545                 550                 555                 560
Cys Ser Ser Leu Arg Lys Arg Leu Ala Asp Leu Asp Thr Arg Leu Pro
                565                 570                 575
Ala Leu Leu Glu Ala Lys Met Leu Ala Leu Ser Gly Ser Cys Phe Ser
            580                 585                 590
Thr Ala Lys Glu Leu Ala Glu Glu Ile Trp Ala Val Ser Ser Glu Arg
        595                 600                 605
Glu Gly Leu Glu Met Phe Leu Gly Arg Leu Leu Ala Leu Ser Ser Arg
610                 615                 620
Asn Thr Arg Arg Leu Gly Ser Val Lys Glu Asp Tyr Leu Arg Cys Arg
```

-continued

```
            625                 630                 635                 640
        Gln Asp Leu Ala Leu Gln Glu Ala Ala His Lys Thr Arg Val Lys Ala
                        645                 650                 655

Asn Thr Val Lys Cys Thr Glu Val Leu Glu Gly Gln Leu Ser Cys Cys
                        660                 665                 670

Arg Cys Pro Leu Leu Glu Arg Val Trp Lys Ala Asp Leu Glu Ala Cys
                        675                 680                 685

Gln Leu Leu Met Gln Ser Leu Glu Ile Gln Ala Gly Ser Ser Ser
                        690                 695                 700

His Val Glu Asp Glu Lys Gln Val His Ser Thr Gly Glu Ala Ala Gln
        705                 710                 715                 720

Thr Ala Ala Leu Ala Val Pro Arg Thr Pro His Pro Glu Glu Glu Lys
                        725                 730                 735

Ser Pro Leu Gln Glu Ser His Val Val Phe Ala Glu Val Gly Asp Lys
                        740                 745                 750

Cys Glu Ala Ile Gly Met Arg Leu Leu His Leu Glu Asp Gln Leu Leu
                        755                 760                 765

Gly Ala Met His Gly His Asp Glu Ala Leu Phe His Ser Leu Gln Gly
                        770                 775                 780

Glu Leu Gln Met Val Lys Glu Thr Leu Gln Thr Met Phe Leu Gln Leu
        785                 790                 795                 800

Gln Pro Ala Lys Glu Ala Gly Glu Ala Ser Ala Ser Tyr Ser Thr
                        805                 810                 815

Ala Gly Ala Gln Glu Ala Glu Asp
                        820

<210> SEQ ID NO 110
<211> LENGTH: 994
<212> TYPE: PRT
<213> ORGANISM: Danio rerio

<400> SEQUENCE: 110

Met Met Phe Ala Gly Met Val Arg Val Glu Asn Thr Ser Lys Thr Leu
1               5                   10                  15

Lys Thr Asp Ile Asp Ser Pro Cys His Arg Cys Ala Val Arg Thr Gly
                20                  25                  30

Gly Val Asn Pro Ser Gly Asn His Arg Arg Arg Ser Phe Arg Arg Pro
            35                  40                  45

Gly Tyr Met Arg Ser Glu Pro Ile Asn Gln Leu Asp Val Ala Glu Thr
        50                  55                  60

Ser Cys Asp Ser Glu His His Arg Ser Pro Ile Ser Lys Ser Pro Ala
65                  70                  75                  80

Val Glu Asn Thr Gln Lys Ser Ala Ser Glu Leu Leu Gly Glu Lys Trp
                85                  90                  95

Leu Thr Glu Gly Phe Glu Arg Asp Asn Ser Lys Ser Ser Asn Lys
                100                 105                 110

His His Leu His Asp Glu Glu Asp Asn Leu Pro Val Gln Ser Arg Asp
            115                 120                 125

Val Phe Asn Ser Ser Phe Ser Phe Ile Gln Gln Ser Leu Asp Thr Ser
        130                 135                 140

Asp Leu Leu Asp Val Asn Thr Cys Tyr Ser Pro Arg Thr Glu His Lys
145                 150                 155                 160

Gln Ser Glu Ser Ala Ser Gly His Gln Leu Lys Ser Lys Thr Ser Asn
                165                 170                 175
```

```
Ser Gly Phe Leu Lys Pro Pro Ser Asp Leu Met Asn His Leu Ser Gln
            180                 185                 190

Ser Glu Thr Ser Ile Val Gln Met Asn Gln Leu Glu Thr Arg Thr Val
        195                 200                 205

Pro Val Ser Gln Ser Lys Ser Ser Phe Leu Lys Pro Leu Ser Ala Leu
    210                 215                 220

Met Asn His Leu Ser Gln Ser Glu Thr Thr Ser Val Pro Ile Asn Gln
225                 230                 235                 240

Ser Glu Thr Ser Ser Ala Pro Lys Ser Gln Ser Asn Ser Gly Phe Leu
            245                 250                 255

Lys Pro Leu Ser Asp Leu Met Lys His Leu Thr Pro Pro Glu Ser Ser
        260                 265                 270

Ile Val Leu Met Asn Gln Ser Glu Thr Ile Thr Ile Pro Met Asn Gln
    275                 280                 285

Thr Lys Asn Ser Thr Ile Pro Val Ser Gln Ser Asn Ala Asp Phe Leu
290                 295                 300

Asn Pro Pro Ser Ala Leu Met Asn His Leu Asn Gln Ser Glu Thr Val
305                 310                 315                 320

Leu Ile Pro Met Asn Gln Ser Glu Thr Ser Ser Ile Pro Val Ser Gln
            325                 330                 335

Ser Asn Ser Gly Phe Leu Lys Pro Ser Ser Asn Leu Ile Asn His Leu
        340                 345                 350

Ser Gln Ser Glu Ser Val Thr Val Pro Met Asn Gln Ser Glu Thr Ser
    355                 360                 365

Thr Val Ser Leu Ser Gln Ser Glu Pro Asp Phe Phe Ser Leu Arg His
370                 375                 380

Leu Pro Cys Ser Ile Gly Gln Ser Ala Gln Gln Lys Gly Leu Leu Leu
385                 390                 395                 400

Asp Arg Glu Leu Trp Leu Val Asp Leu Asp Leu Gln Thr Ser Ser Ser
            405                 410                 415

Ile Met Ser Lys Tyr Thr Lys Glu Asn Ile Gln Asp Ser Asp Ser Gly
        420                 425                 430

Ser Leu Asp Ala Glu Ile Thr Ser Ser His Ser Ile Asp Ser Ser Asp
    435                 440                 445

Ser Thr Ser Ser Gly Tyr Glu Ser Thr Thr Pro Ser Ser Asp Gln Ser
450                 455                 460

Gln Asp Gly Leu Met Lys Lys Tyr Glu Asp Phe Leu Gln Asp Cys Leu
465                 470                 475                 480

Gln Asn Asn Arg Thr Asn Thr Lys Ile Glu Ser Ile Met Met Lys Leu
            485                 490                 495

Gln Arg Leu Gln His Lys Ala Ile Leu Asp Asp Asp Tyr Asp Thr Ala
        500                 505                 510

Glu Arg Phe Gly Lys Lys Leu Glu Glu Leu Arg Arg Glu Arg Ala Thr
    515                 520                 525

Leu Lys Pro Gly Leu Pro Ser Arg His Pro Glu Val Thr Gly Tyr Leu
530                 535                 540

Glu Arg Leu Arg Thr Ala Val Asn Ser Ala Ile His Arg Thr Asp Ser
545                 550                 555                 560

Asp Cys Ser Thr Gly Asp Pro Ser Glu Asp Gln Arg Ser Cys Ile Ser
            565                 570                 575

Gln Ser Arg Ala Gln Thr Arg Glu Thr Leu Leu Glu Glu Lys Gln Arg
        580                 585                 590

Ile Gln Lys Glu Met Cys Asp Val Gln Arg Arg Leu Arg Asp Leu Gln
```

```
                595                 600                 605
        Glu Arg Ser Arg Ala Leu Glu Leu Gln Leu Glu Leu Gln Glu Met Gln
        610                 615                 620
        Gly Pro Val Leu Arg Ala Ala Asp Ser Pro His Leu His Leu Thr Ala
    625                 630                 635                 640
        Arg Ala Leu Glu Asp Leu Leu Thr Ser Glu His Arg Gln Arg Ile Ser
                        645                 650                 655
        Val Ser Pro Pro Ala His Ile Arg Arg Leu Glu Glu Gln Glu Arg Val
                        660                 665                 670
        Leu Ser Leu Ser Ile Arg Glu Ala Glu Thr Lys Val Leu Leu Asn Gln
                        675                 680                 685
        Arg Leu Cys Phe Ser Leu Arg Gln Lys Val Ser Glu Ser Glu Thr Gln
                        690                 695                 700
        Leu Leu Ala Leu His Glu Ala Lys Leu Thr Ala Val Ser Gly Asn Asp
    705                 710                 715                 720
        Phe Ser Ser Ala Lys Glu Leu Lys Ala Glu Ile Arg Ser Val Tyr Arg
                        725                 730                 735
        Glu Arg Asp Arg Leu Glu Leu Leu His Arg Lys Leu Gln Thr Leu Ser
                        740                 745                 750
        Thr Gly Ser Gly Leu Asp Leu Ser Arg Met Lys Glu Lys His Lys His
                        755                 760                 765
        Ile Lys Leu Glu Leu Gln Asn Gly Glu Ala Gln Tyr Glu Arg Ser Leu
    770                 775                 780
        Lys Glu Asn Thr Val Lys Tyr Ile Glu Leu Leu Glu Asp Lys Leu His
    785                 790                 795                 800
        Ser Cys Gly Ser Ala Ala Leu Glu His Val Leu Glu Ala Asp Leu Glu
                        805                 810                 815
        Ala Cys His Leu Leu Lys Gly Leu Asp Gln Arg Asn Leu Ser Leu
                        820                 825                 830
        Ser Gln Thr Glu Asp Leu Pro Ser Gly Ser Ala Ser Ala Ser Asp Val
                        835                 840                 845
        Leu Gln Phe Thr Lys Asp Glu Glu Asp Cys Ala Met Leu Thr Ala Leu
    850                 855                 860
        Gly Gly Arg Trp Cys Pro Glu Ala Asp Leu Gln His Ser Gln Phe Thr
    865                 870                 875                 880
        Lys Lys Leu Glu Glu Phe Leu Phe Cys Leu Glu Asp Glu Ala Pro Glu
                        885                 890                 895
        Asn Leu Cys Gly Glu Thr Thr Glu Leu Thr Glu Arg Cys Glu Leu Ile
                        900                 905                 910
        Ser Tyr Arg Leu His Tyr Leu Glu Glu Gln Leu Gln Thr Ala Ile Asp
                        915                 920                 925
        Asn Asn Asp Lys Glu Leu Thr Leu Ser Leu Glu Arg Glu Val Leu Glu
                        930                 935                 940
        Leu Lys Ser Ala Leu Gln Ala Met Leu Ser Gln Leu Lys Glu Glu Asp
    945                 950                 955                 960
        Glu Asp Glu Glu Asp Glu Glu Lys Tyr Cys Asp Val Glu Glu Glu Gln
                        965                 970                 975
        Val Glu Asp Glu Asp Leu Glu Glu Glu His Tyr Phe Ser Asp Ser Trp
                        980                 985                 990
        Glu Ile

<210> SEQ ID NO 111
<211> LENGTH: 7
```

```
<212> TYPE: PRT
<213> ORGANISM: Homo sapiens

<400> SEQUENCE: 111

Pro Thr Pro Pro Gly Ser His
1               5

<210> SEQ ID NO 112
<211> LENGTH: 707
<212> TYPE: PRT
<213> ORGANISM: Homo sapiens

<400> SEQUENCE: 112

Met Asn Gln Glu Leu Leu Ser Val Gly Ser Lys Arg Arg Thr Gly
1               5                   10                  15

Gly Ser Leu Arg Gly Asn Pro Ser Ser Gln Val Asp Glu Glu Gln
                20                  25                  30

Met Asn Arg Val Val Glu Glu Gln Gln Gln Gln Leu Arg Gln Gln
                35                  40                  45

Glu Glu Glu His Thr Ala Arg Asn Gly Glu Val Val Gly Val Glu Pro
    50                  55                  60

Arg Pro Gly Gly Gln Asn Asp Ser Gln Gln Gly Gln Leu Glu Glu Asn
65                      70                  75                  80

Asn Asn Arg Phe Ile Ser Val Asp Glu Asp Ser Ser Gly Asn Gln Glu
                    85                  90                  95

Glu Gln Glu Glu Asp Glu Glu His Ala Gly Glu Gln Asp Glu Glu Asp
            100                 105                 110

Glu Glu Glu Glu Met Asp Gln Glu Ser Asp Asp Phe Asp Gln Ser
            115                 120                 125

Asp Asp Ser Ser Arg Glu Asp Glu His Thr His Thr Asn Ser Val Thr
130                     135                 140

Asn Ser Ser Ser Ile Val Asp Leu Pro Val His Gln Leu Ser Ser Pro
145                     150                 155                 160

Phe Tyr Thr Lys Thr Thr Lys Met Lys Arg Lys Leu Asp His Gly Ser
                    165                 170                 175

Glu Val Arg Ser Phe Ser Leu Gly Lys Lys Pro Cys Lys Val Ser Glu
                180                 185                 190

Tyr Thr Ser Thr Thr Gly Leu Val Pro Cys Ser Ala Thr Pro Thr Thr
            195                 200                 205

Phe Gly Asp Leu Arg Ala Ala Asn Gly Gln Gly Gln Gln Arg Arg Arg
    210                 215                 220

Ile Thr Ser Val Gln Pro Pro Thr Gly Leu Gln Glu Trp Leu Lys Met
225                 230                 235                 240

Phe Gln Ser Trp Ser Gly Pro Glu Lys Leu Leu Ala Leu Asp Glu Leu
                245                 250                 255

Ile Asp Ser Cys Glu Pro Thr Gln Val Lys His Met Met Gln Val Ile
            260                 265                 270

Glu Pro Gln Phe Gln Arg Asp Phe Ile Ser Leu Leu Pro Lys Glu Leu
            275                 280                 285

Ala Leu Tyr Val Leu Ser Phe Leu Glu Pro Lys Asp Leu Leu Gln Ala
    290                 295                 300

Ala Gln Thr Cys Arg Tyr Trp Arg Ile Leu Ala Glu Asp Asn Leu Leu
305                 310                 315                 320

Trp Arg Glu Lys Cys Lys Glu Glu Gly Ile Asp Glu Pro Leu His Ile
                325                 330                 335
```

Lys Arg Arg Lys Val Ile Lys Pro Gly Phe Ile His Ser Pro Trp Lys
                340                 345                 350

Ser Ala Tyr Ile Arg Gln His Arg Ile Asp Thr Asn Trp Arg Arg Gly
            355                 360                 365

Glu Leu Lys Ser Pro Lys Val Leu Lys Gly His Asp Asp His Val Ile
        370                 375                 380

Thr Cys Leu Gln Phe Cys Gly Asn Arg Ile Val Ser Gly Ser Asp Asp
385                 390                 395                 400

Asn Thr Leu Lys Val Trp Ser Ala Val Thr Gly Lys Cys Leu Arg Thr
                405                 410                 415

Leu Val Gly His Thr Gly Gly Val Trp Ser Ser Gln Met Arg Asp Asn
            420                 425                 430

Ile Ile Ile Ser Gly Ser Thr Asp Arg Thr Leu Lys Val Trp Asn Ala
        435                 440                 445

Glu Thr Gly Glu Cys Ile His Thr Leu Tyr Gly His Thr Ser Thr Val
        450                 455                 460

Arg Cys Met His Leu His Glu Lys Arg Val Val Ser Gly Ser Arg Asp
465                 470                 475                 480

Ala Thr Leu Arg Val Trp Asp Ile Glu Thr Gly Gln Cys Leu His Val
                485                 490                 495

Leu Met Gly His Val Ala Ala Val Arg Cys Val Gln Tyr Asp Gly Arg
            500                 505                 510

Arg Val Val Ser Gly Ala Tyr Asp Phe Met Val Lys Val Trp Asp Pro
        515                 520                 525

Glu Thr Glu Thr Cys Leu His Thr Leu Gln Gly His Thr Asn Arg Val
        530                 535                 540

Tyr Ser Leu Gln Phe Asp Gly Ile His Val Val Ser Gly Ser Leu Asp
545                 550                 555                 560

Thr Ser Ile Arg Val Trp Asp Val Glu Thr Gly Asn Cys Ile His Thr
                565                 570                 575

Leu Thr Gly His Gln Ser Leu Thr Ser Gly Met Glu Leu Lys Asp Asn
            580                 585                 590

Ile Leu Val Ser Gly Asn Ala Asp Ser Thr Val Lys Ile Trp Asp Ile
        595                 600                 605

Lys Thr Gly Gln Cys Leu Gln Thr Leu Gln Gly Pro Asn Lys His Gln
        610                 615                 620

Ser Ala Val Thr Cys Leu Gln Phe Asn Lys Asn Phe Val Ile Thr Ser
625                 630                 635                 640

Ser Asp Asp Gly Thr Val Lys Leu Trp Asp Leu Lys Thr Gly Glu Phe
                645                 650                 655

Ile Arg Asn Leu Val Thr Leu Glu Ser Gly Gly Ser Gly Gly Val Val
            660                 665                 670

Trp Arg Ile Arg Ala Ser Asn Thr Lys Leu Val Cys Ala Val Gly Ser
        675                 680                 685

Arg Asn Gly Thr Glu Glu Thr Lys Leu Leu Val Leu Asp Phe Asp Val
        690                 695                 700

Asp Met Lys
705

<210> SEQ ID NO 113
<211> LENGTH: 163
<212> TYPE: PRT
<213> ORGANISM: Homo sapiens

<400> SEQUENCE: 113

-continued

```
Met Pro Ser Ile Lys Leu Gln Ser Ser Asp Gly Glu Ile Phe Glu Val
1               5                   10                  15

Asp Val Glu Ile Ala Lys Gln Ser Val Thr Ile Lys Thr Met Leu Glu
            20                  25                  30

Asp Leu Gly Met Asp Asp Glu Gly Asp Asp Pro Val Pro Leu Pro
        35                  40                  45

Asn Val Asn Ala Ala Ile Leu Lys Lys Val Ile Gln Trp Cys Thr His
    50                  55                  60

His Lys Asp Asp Pro Pro Pro Glu Asp Asp Glu Asn Lys Glu Lys
65                  70                  75                  80

Arg Thr Asp Asp Ile Pro Val Trp Asp Gln Gly Phe Leu Lys Val Asp
                85                  90                  95

Gln Gly Thr Leu Phe Glu Leu Ile Leu Ala Ala Asn Tyr Leu Asp Ile
                100                 105                 110

Lys Gly Leu Leu Asp Val Thr Cys Lys Thr Val Ala Asn Met Ile Lys
            115                 120                 125

Gly Lys Thr Pro Glu Glu Ile Arg Lys Thr Phe Asn Ile Lys Asn Asp
        130                 135                 140

Phe Thr Glu Glu Glu Ala Gln Val Arg Lys Glu Asn Gln Trp Cys
145                 150                 155                 160

Glu Glu Lys

<210> SEQ ID NO 114
<211> LENGTH: 24
<212> TYPE: PRT
<213> ORGANISM: Homo sapiens

<400> SEQUENCE: 114

Gly Pro Glu Val Pro Pro Thr Pro Pro Gly Ser His Ser Ala Phe Thr
1               5                   10                  15

Ser Ser Phe Ser Phe Ile Arg Leu
            20

<210> SEQ ID NO 115
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Phosphorylation
<220> FEATURE:
<221> NAME/KEY: MOD_RES
<222> LOCATION: (6)..(6)
<223> OTHER INFORMATION: Phosphorylation

<400> SEQUENCE: 115

Pro Thr Pro Pro Gly Ser His Ser
1               5

<210> SEQ ID NO 116
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (3)..(3)
<223> OTHER INFORMATION: Phosphorylation
<220> FEATURE:
<221> NAME/KEY: MOD_RES
<222> LOCATION: (7)..(7)
<223> OTHER INFORMATION: Phosphorylation

<400> SEQUENCE: 116

Pro Pro Thr Pro Pro Gly Ser His
1               5

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Flu
<220> FEATURE:
<221> NAME/KEY: MOD_RES
<222> LOCATION: (4)..(4)
<223> OTHER INFORMATION: Phosphorylation in singly or doubly
      phosphorylated peptide
<220> FEATURE:
<221> NAME/KEY: MOD_RES
<222> LOCATION: (8)..(8)
<223> OTHER INFORMATION: Phosphorylation in doubly phosphorylated
      peptide
<220> FEATURE:
<223> OTHER INFORMATION: See specification as filed for detailed
      description of substitutions and preferred embodiments

<400> SEQUENCE: 117

Val Pro Pro Thr Pro Pro Gly Ser His
1               5

<210> SEQ ID NO 118
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 118

His His His His His His
1               5

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphorylation
<220> FEATURE:
<221> NAME/KEY: MOD_RES
<222> LOCATION: (8)..(8)
<223> OTHER INFORMATION: Phosphorylation

<400> SEQUENCE: 119

Val Pro Pro Thr Pro Pro Gly Ser His
1               5
```

METHODS FOR INCREASING DISC1 IN A SUBJECT WITH SCHIZOPHRENIA OR BIPOLAR DISORDER BY AN ANTAGONIST INHIBITING DISC1 BINDING TO FBXW7

RELATED APPLICATIONS

This application is a National Stage filing and claims the benefit under 35 U.S.C. § 120 to PCT Application PCT/GB2014/052927, filed 29 Sep. 2014, which claims the benefit under 35 U.S.C. § 119 to United Kingdom Patent Application Serial No. GB1317207.7, filed 27 Sep. 2013. The disclosures of the foregoing applications are herein incorporated by reference in their entireties.

SEQUENCE LISTING

The instant application contains a Sequence Listing which has been submitted electronically in ASCII format and is hereby incorporated by reference in its entirety. Said ASCII copy, created on Mar. 24, 2017, is named 20-04553_003US1_SL.txt and is 95,207 bytes in size.

FIELD OF THE INVENTION

The invention relates to the newly-discovered interaction between DISC1 and FBXW7 which regulates DISC1 turnover, and to antagonists that inhibit this interaction, methods of using these antagonists to decrease DISC1 turnover, treatment of neuropsychiatric disorders and other conditions with these antagonists, and methods of identifying new antagonists.

BACKGROUND TO THE INVENTION

Neuropsychiatric disorders have a net lifetime incidence of approximately 1-in-6 worldwide and the World Health Organisation ranks schizophrenia, bipolar disorder and depression $9^{th}$, $6^{th}$ and $1^{st}$ respectively in the global tables for Years Living with Disability. These disorders thus represent a very substantial unmet medical need and societal impact.

There is strong evidence for these related disorders having a substantial and overlapping genetic component. This evidence comes from multiple lines of enquiry. Genome-wide association studies indicate that at least 25% of the risk is polygenic—the sum effect of a large number of common, ancient variants each conferring a very modest incremental risk [1]. In addition to these modest effects, molecular cytogenetic, copy number variant and now sequence level analysis, has identified rare mutations of high impact in genes of biological plausibility. This second class of genes is well suited to mechanistic analysis.

The DISC1 (Disrupted in schizophrenia 1) gene is one of the best validated genes in this category, first identified as a putative risk factor because it is directly disrupted by a chromosomal t(1;11) translocation that co-segregates with major mental illness in a large family from Scotland [2].

DISC1 is a molecular scaffold protein which interacts with, and modulates, multiple proteins that play critical roles in, for example, cAMP, wnt, GABA and NMDA receptor signalling, in mitochondrial and synapse biology, in neurodevelopment, in cellular stress, in neural stem cell growth and differentiation, and in neuronal migration [3]. Thus, the DISC1 complex has the potential to regulate pathways that underpin mental illness.

Understanding the detailed cell biology of DISC1, how this is altered in mental illness and identifying corrective strategies, could transform current thinking about routes toward novel therapeutic targets or biological markers for major mental conditions. Additionally, a novel pharmacologic means of selectively manipulating the levels of DISC1 protein in vivo would allow the role of DISC1 to be evaluated in key aspects of brain development and function [4].

SUMMARY OF THE INVENTION

The inventors have found that turnover of DISC1 (Disrupted in schizophrenia 1) is mediated by the F-box-containing protein FBXW7 (F-box/WD repeat-containing protein 7), and have identified the sequence within DISC1 that binds to FBXW7 and targets DISC1 for turnover by the ubiquitin-proteasome system.

This finding has implications for the treatment of pathological conditions linked to level, function or turnover of DISC1. these may include intellectual disability and/or neuropsychiatric disorders, including schizophrenia, bipolar disorder, depression, recurrent major depressive disorder (rMDD), attention-deficit hyperactivity disorder (ADHD) and autism.

In a first aspect, the invention provides a method for decreasing DISC1 turnover in a biological system, comprising contacting the system with an antagonist capable of inhibiting binding between DISC1 and FBXW7. In particular, an antagonist that binds to FBXW7 and inhibits the interaction between FBXW7 and DISC1 is believed to reduce the rate of DISC1 turnover resulting in increased levels of DISC1. The terms "antagonist" and "inhibitor" are used interchangeably in this specification.

The antagonist may comprise an FBXW7-binding moiety capable of binding to FBXW7 and hence inhibiting DISC1 binding to FBXW7.

The FBXW7-binding moiety may comprise a fragment of a DISC1 protein, or an analogue thereof, which is capable of binding to FBXW7. Such molecules may be capable of binding to the same site on FBXW7 as full-length DISC1 and thus competitively inhibiting (e.g. preventing or disrupting) binding of DISC1 to FBXW7.

Residues 197 to 203 of wild type human DISC1 have the sequence $P_{197}$-$T_{198}$-$P_{199}$-$P_{200}$-$G_{201}$-$S_{202}$-$H_{203}$. This is believed to represent a "phospho-degron" sequence which, especially when phosphorylated at $T_{198}$ and/or $S_{202}$, is recognised by FBXW7 and targets DISC1 for degradation by the ubiquitin-proteasome system. Thus, in the native protein, $T_{198}$ and/or $S_{202}$ may independently be phosphorylated. Without wishing to be bound by theory, these residues are believed to be particularly significant in the interaction between DISC1 and FBXW7, in combination with the proline residue at position $X_{199}$. The FBXW7-binding moiety may thus comprise this sequence or a fragment or analogue thereof.

Thus, the FBXW7-binding moiety may comprise a "core" sequence having the formula:

$$X_{197}\text{-}X_{198}\text{-}P\text{-}X_{200}\text{-}X_{201}\text{-}X_{202}\text{-}X_{203} \qquad \text{(Formula I)}$$

wherein:
  $X_{197}$ is any amino acid or is absent;
  $X_{198}$ is any amino acid or is absent;
  $X_{200}$ is any amino acid;
  $X_{201}$ is any amino acid;
  $X_{202}$ is any amino acid;
  $X_{203}$ is any amino acid or is absent; wherein
  the core sequence comprises at least 4 amino acids;

one or both of $X_{198}$ and $X_{202}$ is a negatively charged amino acid;

$X_{198}$ is absent if $X_{197}$ is absent;

and said core sequence binds to FBXW7.

It may be desirable that the core sequence comprises at least 5 amino acids from Formula I.

Thus, the core sequence may comprise or consist of the formula:

P-$X_{200}$-$X_{201}$-$X_{202}$-$X_{203}$;
$X_{198}$-P-$X_{200}$-$X_{201}$-$X_{202}$;
$X_{198}$-P-$X_{200}$-$X_{201}$-$X_{202}$-$X_{203}$;
$X_{197}$-$X_{198}$-P-$X_{200}$-$X_{201}$-$X_{202}$; or
$X_{197}$-$X_{198}$-P-$X_{200}$-$X_{201}$-$X_{202}$-$X_{203}$.

In any of the above formulae, $X_{200}$ may be P or A; and/or $X_{201}$ may be G, Q, A or a negatively charged amino acid.

In particular, it may be desirable that $X_{200}$ is P and/or $X_{201}$ is G, D or E.

Thus the core sequence may comprise or consist of the amino acid sequence:

P-P-$X_{201}$-$X_{202}$;
P-$X_{200}$-G-$X_{202}$;
P-P-G-$X_{202}$;
P-$X_{200}$-D-$X_{202}$;
P-P-D-$X_{202}$;
P-$X_{200}$-E-$X_{202}$;
P-P-E-$X_{202}$;
$X_{198}$-P-P-$X_{201}$-$X_{202}$;
$X_{198}$-P-$X_{200}$-G-$X_{202}$;
$X_{198}$-P-P-G-$X_{202}$;
$X_{198}$-P-$X_{200}$-D-$X_{202}$;
$X_{198}$-P-P-D-$X_{202}$;
$X_{198}$-P-$X_{200}$-E-$X_{202}$;
$X_{198}$-P-P-E-$X_{202}$;
$X_{197}$-$X_{198}$-P-P-$X_{201}$-$X_{202}$-$X_{203}$
$X_{198}$-P-P-$X_{201}$-$X_{202}$-$X_{203}$;
$X_{197}$-$X_{198}$-P-P-$X_{201}$-$X_{202}$-$X_{203}$;
$X_{197}$-$X_{198}$-P-$X_{200}$-G-$X_{202}$
$X_{198}$-P-$X_{200}$-G-$X_{202}$-$X_{203}$;
$X_{197}$-$X_{198}$-P-$X_{200}$-DG-$X_{202}$-$X_{203}$;
$X_{197}$-$X_{198}$-P-$X_{200}$-D-$X_{202}$;
$X_{198}$-P-$X_{200}$-D-$X_{202}$-$X_{203}$;
$X_{197}$-$X_{198}$-P-$X_{200}$-D-$X_{202}$-$X_{203}$;
$X_{197}$-$X_{198}$-P-$X_{200}$-E-$X_{202}$;
$X_{198}$-P-$X_{200}$-E-$X_{202}$-$X_{203}$;
$X_{197}$-$X_{198}$-P-$X_{200}$-E-$X_{202}$-$X_{203}$;
$X_{197}$-$X_{198}$-P-P-G-$X_{202}$;
$X_{198}$-P-P-G-$X_{202}$-$X_{203}$;
$X_{197}$-$X_{198}$-P-P-G-$X_{202}$-$X_{203}$;
$X_{197}$-$X_{198}$-P-P-D-$X_{202}$;
$X_{198}$-P-P-D-$X_{202}$-$X_{203}$;
$X_{197}$-$X_{198}$-P-P-D-$X_{202}$-$X_{203}$;
$X_{197}$-$X_{198}$-P-P-E-$X_{202}$;
$X_{198}$-P-P-E-$X_{202}$-$X_{203}$; or
$X_{197}$-$X_{198}$-P-P-E-$X_{202}$-$X_{203}$

One or both of $X_{198}$ and $X_{202}$ is an amino acid with a negatively charged side chain. These may be naturally-occurring amino acids or post-translationally modified derivatives thereof which occur physiologically in mammalian proteins, such as aspartic acid (D), glutamic acid (E) and phosphorylated amino acids such as phospho-serine (pS), phospho-threonine (pT) and phospho-tyrosine (pY).

Alternatively they may be non-naturally occurring amino acids which possess negatively charged side chains.

Any of these residues may independently be present at each of $X_{198}$ and/or $X_{202}$, although D, E, pS and pT may be preferred to pY.

When not a negatively charged amino acid, $X_{198}$ and $X_{202}$ may be any amino acid, especially any of the 18 other naturally-occurring amino acids. Residues having a non-polar side chain may be preferred, such as Ala or Gly.

It may be desirable that both $X_{198}$ and $X_{202}$ have a negatively charged side chain. Thus, each of $X_{198}$ and $X_{202}$ may independently be selected amongst D, E, pS and pT. In some embodiments, both $X_{198}$ and $X_{202}$ are independently selected from D, E.

Thus, any of the formulae presented above may comprise the sequence:

D-P-$X_{200}$-$X_{201}$-E;
E-P-$X_{200}$-$X_{201}$-D;
D-P-$X_{200}$-$X_{201}$-D; or
E-P-$X_{200}$-$X_{201}$-E.

As already mentioned, in each of these sequences, $X_{200}$ may be P and/or $X_{201}$ may be G, D or E.

Without wishing to be bound by any particular theory, structural analysis of the DISC1-FBXW7 complex suggests that the phosphorylated side chain of $T_{198}$ may be capable of intramolecular electrostatic interaction (e.g. forming a hydrogen bond) with the hydrogen atom at its backbone nitrogen atom. This may weaken the potential interaction between the charged phosphate group and FBXW7. A similar intramolecular interaction may be possible at $S_{202}$. In order to maximise the strength of interaction between the FBXW7-binding moiety and FBXW7, it may therefore be desirable to incorporate modifications of the peptide backbone in order to minimise or eliminate such intramolecular interactions.

Thus, when $X_{198}$ is a residue with a negatively charged side chain, it may be desirable that the backbone nitrogen atom of $X_{198}$ does not carry a hydrogen atom capable of participating in a hydrogen bond with the side chain. Thus the backbone nitrogen is substituted with a group other than hydrogen, e.g. the backbone nitrogen forms part of a tertiary amide group.

Independently, when $X_{202}$ is a residue with a negatively charged side chain, it may be desirable that the backbone nitrogen atom of $X_{202}$ does not carry a hydrogen atom capable of participating in a hydrogen bond with the side chain. Thus the backbone nitrogen is substituted with a group other than hydrogen, e.g. the backbone nitrogen forms part of a tertiary amide group.

In either case, any suitable substituent may be present at the backbone nitrogen atom, as long as the FBXW7-binding moiety remains capable of binding to FBXW7. For example, the substituent may be a methyl group. A methylated nitrogen may be designated by a lower case "m" before the normal designation of the amino acid, e.g. "mD" represents methylated aspartic acid.

Thus, when they are negatively charged residues, each of $X_{198}$ and $X_{202}$ may independently be mD, mE, mpS, mpT, or any suitable analogue thereof.

As already set out above, it may be desirable that both $X_{198}$ and $X_{202}$ have a negatively charged side chain. Thus, each of $X_{198}$ and $X_{202}$ may independently be selected amongst D, E, pS, pT, mD, mE, mpS, mpT and suitable N-substituted glycine analogues thereof. In some embodiments, both $X_{198}$ and $X_{202}$ are independently selected from D, E, mD and mE. For example, $X_{198}$ and $X_{202}$ may both independently be mD or mE. In some embodiments, $X_{198}$ is mD and $X_{202}$ is mE, or both $X_{198}$ and $X_{202}$ are mE.

Thus, any of the formulae presented above may comprise the sequence:

mD-P-$X_{200}$-$X_{201}$-E;
D-P-$X_{200}$-$X_{201}$-mE;

mD-P-$X_{200}$-$X_{201}$-mE;
mE-P-$X_{200}$-$X_{201}$-D;
E-P-$X_{200}$-$X_{201}$-mD;
mE-P-$X_{200}$-$X_{201}$-mD;
mD-P-$X_{200}$-$X_{201}$-D;
D-P-$X_{200}$-$X_{201}$-mD;
mD-P-$X_{200}$-$X_{201}$-mD;
mE-P-$X_{200}$-$X_{201}$-E;
E-P-$X_{200}$-$X_{201}$-mE; or
mE-P-$X_{200}$-$X_{201}$-mE.

As already mentioned, in each of these sequences, $X_{200}$ may be P and/or $X_{201}$ may be G, D or E.

In any of the above formulae, $X_{197}$ (when present) may be P, G, A, I, L, D or E (e.g. P or G) or a suitable analogue of any of these residues.

$X_{203}$ (when present) may be a residue having a positively charged or basic side chain (e.g. H, R or K) or an aromatic residue (e.g. F, W or Y) or a suitable analogue of any of these residues. For example, H or K may be present at this position.

In each of these formulae, one or both of $X_{198}$ and $X_{202}$ is a negatively charged residue, which may be independently selected as defined above. It may be desirable that both $X_{198}$ and $X_{202}$ are negatively charged residues. mE and mD may be preferred, but any of the negatively charged residues discussed above may also be employed, as well as non-naturally occurring amino acids having negatively charged side chains.

Alternatively, one of both of $X_{198}$ and $X_{202}$ may be an N-substituted glycine residue, wherein the N-substituent is a charged moiety, such as the side chain of aspartic acid, glutamic acid, phospho-serine or phospho-threonine. Such N-substituted glycine residues are analogues of naturally-occurring (or other) amino acids in which the side chain is linked to the backbone nitrogen rather than to the alpha-carbon. Polymers of such N-substituted glycine residues are often referred to as "peptoid" polymers. (See also below.)

References to a negatively charged amino acid or side chain should be taken to mean that, in the absence of secondary structure, the side chain of the amino acid carries at least a partial negative charge at physiological pH (typically pH 7.4). Typically such side chains carry one negative charge under these conditions, although they may carry two or three negative charges, depending on the functional groups present. It may be desirable that any given side chain carries no more than one, no more than two, or no more than three negative charges. Likewise, reference to a positively charged amino acid or side chain should be taken to mean that, in the absence of secondary structure, the side chain of the amino acid carries at least a partial positive charge at physiological pH (typically pH 7.4). Typically such side chains carry nor more than one positive charge under these conditions.

Throughout the definitions above, each amino acid residue may independently be in the L or D form.

Thus, the core sequence may comprise one or more D-amino acids. Thus a core sequence of 5 amino acids may comprise 1, 2, 3, 4 or 5 D-amino acids. A core sequence of 6 amino acids may comprise 1, 2, 3, 4, 5 or 6 D-amino acids. A core sequence of 7 amino acids may comprise 1, 2, 3, 4, 5, 6 or 7 D-amino acids.

Those amino acids which are not D-amino acids are typically L-amino acids.

It may be desirable that $X_{198}$ and/or $X_{202}$ (when present) are D-amino acids. It may be desirable that only $X_{198}$ and/or $X_{202}$ (when present) are D-amino acids, with the remainder of the core being composed of L-amino acids.

In certain embodiments, the amino acid sequence may be in the all-D form, the retro form, or the retro all-D form (also known as "retro-inverso"). In the retro all-D form, the core amino acid sequences shown in the formulae above run from C-terminus to N-terminus, instead of the more conventional N-terminus to C-terminus.

Additionally or alternatively, the core sequence may comprise one or more N-substituted glycine analogue of an amino acid. In this context, an N-substituted glycine analogue of a given amino acid is an N-substituted glycine residue in which the N-linked substituent is the side chain of that amino acid which would normally be linked to the alpha-carbon. As alluded to above, it may be particularly desirable that such residues are present at $X_{198}$ and/or $X_{202}$, since such residues have no N-linked hydrogen to participate in a hydrogen bond with the respective side chain. However, any or all of the core residues may be an N-substituted glycine analogue of an amino acid. A stretch of two or more consecutive such analogues may be referred to as a peptoid.

Peptoids have a number of desirable properties. In addition to the implications for internal hydrogen bonding, they are typically resistant to proteolysis.

The entire core sequence, or the entire FBXW7-binding moiety, or the entire antagonist, may be a peptoid.

The core sequence may comprise or consist of a sequence selected from the group consisting of:
16: P-E-P-P-G-d-H (SEQ ID NO: 1);
35: P-E-P-P-G-d-H (SEQ ID NO: 1);
55: P-e-P-P-G-mE-H (SEQ ID NO: 2);
64: P-E-P-P-G-mD-H (SEQ ID NO: 3);
75: P-e-P-P-G-mE-H (SEQ ID NO: 2);
79: P-e-P-P-G-mD-H (SEQ ID NO: 4);
82: P-d-P-P-G-mE-H (SEQ ID NO: 5);
90: P-d-P-P-G-mE-H (SEQ ID NO: 5);
91: P-d-P-P-G-mE-H (SEQ ID NO: 5);
139: G-mE-P-P-G-mE-H (SEQ ID NO: 6);
142: G-mD-P-P-G-mE-H (SEQ ID NO: 7);
147: G-e-P-P-G-mE-H (SEQ ID NO: 8);
173: G-d-P-P-G-mE-H (SEQ ID NO: 9);
181: G-d-P-P-G-mE-H (SEQ ID NO: 9);
139': G-mE-P-P-G-mE (SEQ ID NO: 10);
139'': mE-P-P-G-mE-H (SEQ ID NO: 11);
142': mD-P-P-G-mE-H (SEQ ID NO: 12);
A5 G-d-P-P-G-mE (SEQ ID NO: 13);
A12 G-d-P-P-Q-mE-H (SEQ ID NO: 14);
A13 G-d-P-P-q-mE-H (SEQ ID NO: 15);
A18 L-d-P-P-G-mE-H (SEQ ID NO: 16);
A22 G-A-P-P-G-mE-H (SEQ ID NO: 17);
A25 G-e-P-P-G-mE (SEQ ID NO: 18);
A26 e-P-P-G-mE-H (SEQ ID NO: 19);
A31 a-e-P-P-G-mE-H (SEQ ID NO: 20);
A40 P-pT-P-P-G-pS-H (SEQ ID NO: 21);
A45 G-mD-P-P-G-mE (SEQ ID NO: 22);
A51 a-mD-P-P-G-mE-H (SEQ ID NO: 23);
A52 G-mD-P-P-Q-mE-H (SEQ ID NO: 24);
A56 G-mD-P-p-G-mE-H (SEQ ID NO: 25);
A58 L-mD-P-P-G-mE-H (SEQ ID NO: 26);
A71 a-mE-P-P-G-mE-H (SEQ ID NO: 27);
A73 G-mE-P-P-q-mE-H (SEQ ID NO: 28);
A76 G-mE-P-p-G-mE-H (SEQ ID NO: 29);
A79 l-mE-P-P-G-mE-H (SEQ ID NO: 30);
A80 P-pT-P-P-G-pS-H (SEQ ID NO: 21);
A82 P-A-P-P-G-mE-H (SEQ ID NO: 31);
A85 P-d-P-P-G-mE (SEQ ID NO: 32);
A86 d-P-P-G-mE-H (SEQ ID NO: 33);
A97 P-d-p-P-G-mE-H (SEQ ID NO: 34);
A98 L-d-P-P-G-mE-H (SEQ ID NO: 35);

A99 l-d-P-P-G-mE-H (SEQ ID NO: 36);
A100 P-pT-P-P-G-pS-H (SEQ ID NO: 21);
A101 P-e-P-P-G-mD-H (SEQ ID NO: 37);
A102 P-A-P-P-G-mD-H (SEQ ID NO: 38);
A119 P-pT-P-P-G-pS-H (SEQ ID NO: 21);
A124 P-e-P-P-G-mE (SEQ ID NO: 39);
A130 a-e-P-P-G-mE-H (SEQ ID NO: 40);
A131 P-e-P-P-Q-mE-H (SEQ ID NO: 41);
A132 P-e-P-P-q-mE-H (SEQ ID NO: 42);
A135 P-e-P-p-G-mE-H (SEQ ID NO: 43);
A136 P-e-p-P-G-mE-H (SEQ ID NO: 44);
A137 L-e-P-P-G-mE-H (SEQ ID NO: 45);
A138 l-e-P-P-G-mE-H (SEQ ID NO: 46);
A139 P-pT-P-P-G-pS-H (SEQ ID NO: 21);
A144 P-E-P-P-G-mD (SEQ ID NO: 47);
A151 P-E-P-P-Q-mD-H (SEQ ID NO: 48);
A160 G-d-P-P-G-mE-H (SEQ ID NO: 9);
A161 a-d-P-p-G-mE-H (SEQ ID NO: 49);
A162 a-d-p-P-G-mE-H (SEQ ID NO: 50);
A163 a-d-p-p-G-mE-H (SEQ ID NO: 51);
A164 a-d-P-P-G-mE-h (SEQ ID NO: 52);
A165 a-d-P-P-a-mE-h (SEQ ID NO: 53);
A166 a-d-P-P-a-mE-H (SEQ ID NO: 54);
A168 a-d-P-p-a-mE-h (SEQ ID NO: 55);
A169 a-d-p-p-a-mE-h (SEQ ID NO: 56);
A170 G-d-P-p-a-mE-H (SEQ ID NO: 57);
A171 G-d-P-p-a-mE-h (SEQ ID NO: 58);
A172 G-d-p-p-G-mE-H (SEQ ID NO: 59);
A173 G-d-p-p-a-mE-H (SEQ ID NO: 60);
A174 G-d-p-p-G-mE-h (SEQ ID NO: 61);
A175 G-d-p-p-a-mE-h (SEQ ID NO: 62);
A176 a-d-P-p-a-mE-h (SEQ ID NO: 55);
A177 G-d-P-p-a-mE-H (SEQ ID NO: 57);
A180 G-d-p-P-G-mE-H (SEQ ID NO: 63);
A181 p-d-P-P-G-mE-H (SEQ ID NO: 64);
A184 p-d-P-P-G-mE-h (SEQ ID NO: 65);
A185 P-pT-P-P-G-pS-H (SEQ ID NO: 21);
A186 G-d-P-P-G-mE (SEQ ID NO: 66);
A188 d-P-P-G-mE-H (SEQ ID NO: 67);
A189 P-P-G-mE-H (SEQ ID NO: 68);
A192 G-d-P-A-G-mE-K (SEQ ID NO: 69);
A193 G-d-P-a-G-mE-k (SEQ ID NO: 70);
A194 P-d-P-P-G-mE-K (SEQ ID NO: 71);
A195 P-d-P-P-G-mE-k (SEQ ID NO: 72);
A196 G-d-P-P-a-mE-k (SEQ ID NO: 73); and
A197 a-d-P-P-a-mE-k (SEQ ID NO: 74);

or a fragment of at least four amino acids of any one of these sequences which complies with the requirements of Formula I.

In the above sequences, lower case letters represent D-amino acids, and spaces have been introduced purely to assist alignment of residues in corresponding positions of Formula I.

The core sequence may also be a variant of any of the above sequences in which:
(i) one or more of the amino acids present is replaced by an N-substituted glycine analogue of that amino acid;
(ii) any D-amino acid is exchanged for the equivalent L amino acid; and/or
(iii) any L-amino acid is exchanged for the equivalent D amino acid.

It will be understood that, in the formulae provided above for the "core" sequence, the numbering used is intended simply to identify the corresponding residue in the full-length sequence of DISC1. It should not be taken to imply any particular length for the FBXW7-binding moiety itself.

The FBXW7 binding moiety may consist solely of the core sequence described above. Alternatively, it may comprise further protein sequence N-terminal and/or C-terminal of the core sequence, i.e. N- or C-terminal flanking sequence. For example, it may comprise further DISC1 sequence corresponding to sequences N-terminal or C-terminal of the phosphodegron motif in DISC1, e.g. from human DISC1 or from any other suitable species.

It may be desirable that the core sequence is at the N-terminus or at the C-terminus of the FBXW7 binding moiety, or within 5 or 10 amino acids of the N- or C-terminus.

The FBXW7-binding moiety may comprise or consist of at least 5, 6, 7, 8, 9, 10, 15, 20, 25, 30, 35, 40, 45, 50 or more amino acids.

Additionally or alternatively, the FBXW7-binding moiety may have a maximum length of 5, 6, 7, 8, 9, 10, 15, 20, 25, 30, 35, 40, or 50 amino acids.

The FBXW7-binding moiety may have at least 60% or at least 65%, 70%, 75%, 80%, 85%, 90%, 95%, 98% or 99% sequence identity with the corresponding sequence of DISC1. The FBXW7-binding moiety may be identical to the corresponding sequence of human DISC1. (For the purposes of determining sequence identity, both phosphorylated and unphosphorylated forms of threonine at position 198 and serine at position 202 should be considered identical to the corresponding residues of human DISC1. Where the FBXW7-binding moiety contains a core sequence which is different to a DISC1 phosphodegron motif, any flanking N- and/or C-terminal sequence may be identical to the corresponding sequence of human DISC1.

The FBXW7 binding moiety may comprise 2, 3, 4 or 5 or more consecutive amino acids of DISC1, e.g. 6, 7, 8, 9, 10, 12, 15, 20, 25, 30, 35, 40, 45, 50 or more consecutive amino acids of a DISC1, or an analogue thereof.

Where the terms "comprising", "comprises", "including", "includes" or the like are used herein with respect to the properties of a particular embodiment (for example, an antagonist, FBXW7-binding moiety or fragment etc. comprising a particular amino sequence) the disclosure should be understood as applying mutatis mutandis to embodiments which "consist" or "consist essentially" of those properties (e.g. that amino acid sequence).

The antagonist may be modified or derivatised at the N- and/or C-terminus, for example to improve stability (e.g. against proteolysis), to improve interaction with FBXW7, or for other purposes. For example, the C-terminus may be amidated or acylated. The N-terminus may be alkylated (e.g. with a C1-4 alkyl group, such as a methyl group) or acylated (e.g. with an acetyl, formyl, benozyl or trifluoroacetyl group). The N-terminus may be glycosylated or otherwise derivatised, e.g. by conjugation of polyethylene glycol to the antagonist (commonly referred to as PEGylation). The invention further provides that the N-terminus may comprise a capping group. For example, the N-terminus may comprise a capping group formed by a condensation reaction with any one of the following:

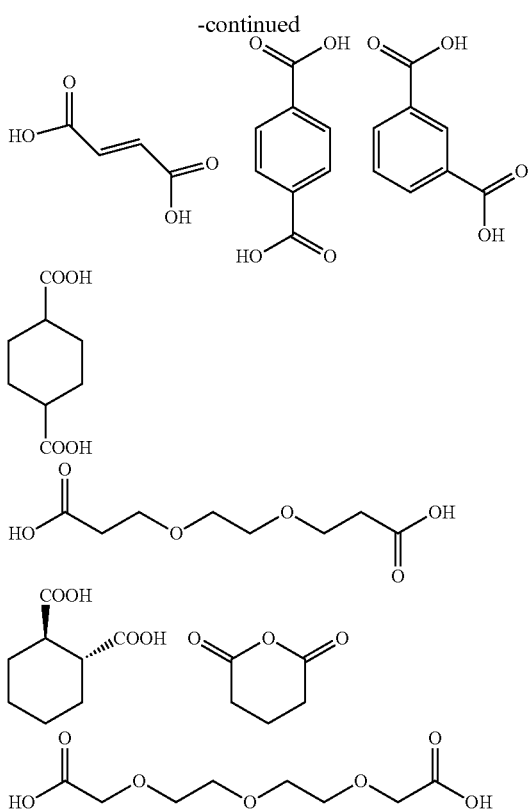

or with any other suitable capping moiety.

An antagonist as described herein may comprise one or more heterologous components. A heterologous component is typically a moiety with a function other than binding to FBXW7. Where the heterologous component is protein in nature, it typically is not derived from DISC1, e.g. it has a sequence which does not have more than 25% sequence identity with any stretch of DISC1 sequence of the same length.

The heterologous component may modulate a property of the antagonist such as stability, activity, immunogenicity, solubility, bioavailability, membrane permeability, ability to cross the blood brain barrier or localisation. For example, the heterologous component may be used to increase or reduce half-life in vitro or in vivo.

Thus the antagonist may be chemically derivatised with a heterologous component in order to modify its pharmacokinetic and/or activity properties. For example, the heterologous component may be a non-proteinaceaous molecule chemically linked to the antagonist. Examples include polyethylene glycol (PEG), poly-sialic acid and fatty or lipid moieties to increase membrane permeability.

The heterologous component may be linked to the free N- or C-terminus of the core sequence, or to a side chain of one of the residues of the core sequence. Alternatively, the FBXW7-binding moiety may comprise one or more additional amino acids N- or C-terminal of the core sequence and the heterologous component may be linked to the free N- or C-terminus provided by that additional amino acid, or to the side chain thereof. Thus an amino acid with a readily derivatisable functional group in the side chain may be preferred, such as Cys or Lys.

The heterologous component may be a protein or domain thereof. For example, it may be an immunoglobulin Fc region. Fusions between Fc regions and non-immunoglobulin components are often referred to as immunoadhesins. Alternatively it may be a protein such as albumin which can be used to extend half-life in vivo.

The heterologous component may be a moiety to increase membrane permeability, i.e. to increase or facilitate transit or transport of the antagonist across cell membranes.

This moiety may be a suitable lipid or other fatty moiety, including but not limited to cholesterol and stearoyl moieties.

Alternatively it may comprise or consist of a cell penetrating peptide (CPP) or peptide transduction domain (PTD). Cell penetrating peptides are often amphipathic or cationic sequences and include L-penetratin, D-penetratin, Tat protein and peptide fragments thereof, Syn-B vectors, FBB (fusion sequence-based peptide) and SBP (signal sequence-based peptide) transducing peptide sequence, also known as a cell penetrating peptide (CPP).

Examples include:

```
Penetratin (43-58)        RQIKIWFQNRRMKWKK

Amphipathic model peptide KLALKLALKALKAALKLA

Transportan              GWTLNSAGYLLKINLKALAALAKKIL

SBP                      MGLGLHLLVLAAALQGAWSQPKKKRKV

FBP                      GALFLGWLGAAGSTMGAWSQPKKKRKV

HIV Tat peptide (48-60)  GRKKRRQRRRPPQ

Syn-B1                   RGGRLSYSRRRFSTSTGR

Syn-B3                   RRLSYSRRRF

Homoarginine peptides    RRRRRRR(RR)
((Arg)7 and (Arg)9)
```

For more details and references, see Hervé, F et al., The AAPS Journal, 10(3), 2008, 455-472.

Additionally or alternatively, the heterologous moiety may assist in passage of the antagonist across the blood-brain barrier. This may be useful for antagonists administered peripherally but intended for treatment of conditions of the brain (e.g. schizophrenia) or other parts of the central nervous system (CNS).

Various ways have been proposed to increase transport of peptides and their analogues across the blood brain barrier. Examples include conjugation to polycationic polymers (e.g. hexamethylenediamine (HMD), putrescine, spermine or spermidine) and amino acid sequences (e.g. the Tat peptide, Syn-B1, Syn-B3 and homoarginine peptides described above). Admixture with such poly-cationic polymers or proteins (e.g. protamines) may also be effective. See Hervé et al., 2008, cited above.

However, modification of the molecule itself may not be required to achieve delivery to the CNS. A suitable choice of administration route may serve equally well. For example, intranasal administration has been proposed to allow proteins and peptides to bypass the blood brain barrier for CNS delivery. (Hanson & Frey, BMC Neuroscience 2008, 9(Suppl. 3):S5.)

The heterologous component may be cleavable from the antagonist. For example, the heterologous component may be cleaved before or after the antagonist enters a cell.

The heterologous component may prevent the antagonist from inhibiting DISC1 binding to FBXW7. An antagonist having such a heterologous component may be an inactive "pro-drug", which is activated when the heterologous component is modified, e.g. cleaved before or after the antagonist enters a cell. Thus the invention further provides a pro-drug form of an antagonist of the invention, wherein the pro-drug form is activated when a heterologous component is modified e.g. cleaved.

In other embodiments, though, the heterologous moiety does not interfere with the ability of the FBXW7-binding moiety to inhibit DISC1 from binding to FBXW7.

Where appropriate, the heterologous component may be expressed as a fusion protein with the FBXW7-binding moiety.

In the case of fusion proteins, a flexible peptide linker is typically included between the two components to allow the two components to interact freely with one another without steric hindrance. The skilled person is capable of designing a suitable linker. Such linkers may, for example, be between 12 and 20 amino acids in length, and have a high proportion of small and hydrophilic amino acid residues (e.g. glycine and serine) to provide the required flexibility without compromising aqueous solubility of the molecule. The linker sequence may comprise a cleavage signal sequence, e.g. a recognition/cleavage site for a protease, to allow removal of the heterologous component from the FBXW7-binding moiety.

In a further aspect, the invention further provides an antagonist of the interaction between DISC1 and FBXW7 comprising an FBXW7-binding moiety having a core sequence as described above.

In this aspect of the invention, the antagonist or FBXW7-binding moiety is not full length DISC1 protein. However, it may be a fragment of DISC1 protein having a maximum of 800, 700, 600, 500, 400, 300, 250, 200, 150, 100, 90, 80, 70, 60 or 50 consecutive residues of DISC1 sequence and containing the phosphodegron motif described herein. Alternatively, the antagonist or FBXW7-binding moiety may comprise DISC1 sequence apart from the residues corresponding to the phosphodegron motif, which may be another sequence falling within Formula I as described above.

The invention further provides a nucleic acid sequence encoding an FBXW7-binding moiety antagonist of the interaction between DISC1 and FBXW7, as described above. It will be understood that a nucleic acid is normally only capable of encoding a molecule which consists entirely of the 20 naturally occurring (proteinogenic) amino acids.

The invention further provides a vector (e.g. an expression vector) comprising a nucleic acid of the invention. An expression vector typically comprises the above-described nucleic acid sequence in combination with sequences to direct its transcription and translation to yield the FBXW7-binding moiety or antagonist.

The invention also provides a host cell comprising a nucleic acid or a vector of the invention. The host cell may be prokaryotic or eukaryotic.

The host cells may be capable of expressing and secreting the antagonist of the invention when cultured under suitable conditions.

The invention further provides a composition comprising an antagonist (or a salt or derivative thereof), a nucleic acid, vector or host cell of the invention and a carrier. In preferred embodiments, the composition is a pharmaceutically acceptable composition, the carrier is a pharmaceutically acceptable carrier, and any salt or derivative is a pharmaceutically acceptable salt or derivative.

References to a composition comprising an antagonist of the invention, or administration of an antagonist of the invention, should be construed to encompass nucleic acids, expression vectors or host cells of the invention except where the context demands otherwise.

The antagonists of the invention may be manufactured by standard peptide synthetic methods, by use of recombinant expression systems, by a combination of the two, or by any other suitable method. Thus, the compounds may be synthesized in a number of ways, including, e.g., methods comprising:

(a) synthesizing the antagonist by standard solid-phase or liquid-phase methodology, either stepwise or by fragment assembly, and isolating and purifying the antagonist;

(b) expressing a nucleic acid construct that encodes the antagonist or a fragment or precursor thereof in a host cell and recovering the expression product from the host cell culture; or (c) effecting cell-free in vitro expression of a nucleic acid construct encoding the antagonist or a fragment or precursor thereof, and recovering the expression product;

or by any combination of the methods of (a), (b) or (c) to obtain fragments of the peptide compound, subsequently joining (e.g., ligating) the fragments to obtain the peptide compound, and recovering the peptide compound.

The method of synthesis may comprise the step of chemically modifying one of more amino acid side chains in a precursor peptide to yield an antagonist of the invention. Such modification may, for example, introduce one or more non-naturally occurring amino acids, convert one or more amino acids into non-naturally occurring amino acids by chemical modification of the side chain, introduce a substituent (such as a methyl group) at a backbone nitrogen atom, or conjugate a heterologous component, such as a polycationic polymer, to a side chain or to a free N- or C-terminal group.

Accordingly, the present invention also provides methods for producing an antagonist of the invention according to above recited methods; a nucleic acid molecule encoding part or all of an antagonist of the invention or a precursor thereof, a vector comprising at least one nucleic acid of the invention, expression vectors comprising at least one nucleic acid of the invention capable of producing an antagonist of the invention when introduced into a host cell, and a host cell comprising a nucleic acid molecule, vector or expression vector of the invention.

It will be apparent to the skilled person that other types of antagonist may also be suitable for use in the methods of the invention. The inhibitor may be an antibody specific for FBXW7 or a functional fragment thereof, or a molecule comprising an antibody binding site specific for FBXW7.

Alternatively the inhibitor may comprise a nucleic acid, e.g. an aptamer, having affinity for FBXW7. Such moieties may bind to the same site as DISC1, or to a different site, and may (for example) inhibit binding of DISC1 competitively, by steric interference, or by inducing a conformational change in FBXW7 which inhibits DISC1 binding.

It is well known that fragments of a whole antibody can perform the function of binding antigens. Examples of functional binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (viii) bispecific single chain Fv dimers (PCT/US92/09965) and (ix) "diabodies", multivalent or multispecific fragments constructed by gene fusion (WO94/13804; P. Holliger et al Proc. Natl. Acad. Sci. USA 90 6444-6448, 1993).

As antibodies can be modified in a number of ways, the term "antibody" should therefore be construed as covering any specific binding substance having an binding domain with the required specificity. Thus, this term covers the antibody fragments described above, as well as derivatives, functional equivalents and homologues of antibodies, including any polypeptide comprising an immunoglobulin binding domain, whether natural or synthetic. Chimaeric molecules comprising an immunoglobulin binding domain, or equivalent, fused to another polypeptide are therefore included. Cloning and expression of chimaeric antibodies are described in EP-A-0120694 and EP-A-0125023.

Alternatives to antibodies are increasingly available. So-called "affinity proteins" or "engineered protein scaffolds" can routinely be tailored for affinity against a particular target. They are typically based on a non-immunoglobulin scaffold protein with a conformationally stable or rigid core, which has been modified to have affinity for the target. Such molecules are clearly envisaged for use as binding agents in the present invention.

Modification may include replacement of one or more surface residues, and/or insertion of one or more residues at the surface of the scaffold protein. For example, a peptide with affinity for the target may be inserted into a surface loop of the scaffold protein or may replace part or all of a surface loop of the scaffold protein. Suitable scaffolds and their engineered equivalents include:

BPTI, LAC-DI, ITI-D2 (Kunitz domain scaffolds);
ETI-II, AGRP (Knottin);
thioredoxin (peptide aptamer);
Fn3 (AdNectin);
lipocalin (BBP) (Anticalin);
ankyrin repeat (DARPin);
Z domain of protein A (Affibody);
gamma-B-crystallin/ubiquitin (Affilin);
LDLR-A-domain (Avimer).

See, for example, Gebauer, M and Skerra, A, Current Op. Chem. Biol. 2009, 13: 245-255, and Friedman, M and Stahl, S, Biotechnol. Appl. Biochem. (2009) 53: 1-29, and references cited therein.

Methods of the invention may be applied in any appropriate biological system, whether in vivo, ex vivo or in vitro. In general, the system will contain FBXW7. The system may also contain DISC1.

An in vitro or ex vivo biological system may comprise an isolated sample of tissue, blood, plasma or serum, or an isolated cell. A cell or tissue sample may be from any tissue in which DISC1 is expressed, including lung, digestive tract, placenta, lymph, liver, skin, heart, kidney and brain, although brain tissue may be preferred. The cell or tissue may be from any suitable species. Preferred subjects are primates (including humans), although cells and tissues from other animals including rodents (including mice and rats), and other common laboratory, domestic and agricultural animals (including but not limited to rabbits, dogs, cats, horses, cows, sheep, goats, pigs, etc.) may be used. Due to its transparent nature, cells and tissues from zebrafish may also be employed.

Alternatively, the system may be assembled in vitro from individual components such as isolated proteins (e.g. recombinant proteins), cells (which may be isolated from tissue, or grown in culture), etc.

The methods of the invention may also be applied in vivo in situations where decreased DISC1 turnover is desirable. Such situations include conditions in which DISC1 has a protective or therapeutic effect on the pathogenesis or symptoms of the condition, either directly or indirectly.

Conditions in which DISC1 dysregulation or dysfunction has been implicated in pathogenesis or symptoms include intellectual disability and/or neuropsychiatric disorders, including schizophrenia, bipolar disorder, depression, recurrent major depressive disorder (rMDD), attention-deficit hyperactivity disorder (ADHD) and autism.

Thus the invention provides a method of treating intellectual disability and/or a neuropsychiatric disorder in an individual, the method comprising administering an antagonist capable of inhibiting DISC1 binding to FBXW7. Alternatively, the method comprises administering a nucleic acid, vector or host cell as described herein.

The invention also provides an antagonist capable of inhibiting DISC1 binding to FBXW7, or a nucleic acid, vector or host cell as described herein, for use in a method of medical treatment, for example for treating intellectual disability and/or a neuropsychiatric disorder.

The invention also provides use of an antagonist capable of inhibiting DISC1 binding to FBXW7, or use of a nucleic acid, vector or host cell as described herein, in the preparation of a medicament for the treatment of intellectual disability and/or a neuropsychiatric disorder.

The treatment described above may be a method of prophylactic treatment.

The antagonist may be any antagonist capable of inhibiting DISC1 binding to FBXW7 described herein.

The invention also provides methods by which agents may be screened for an ability to inhibit the interaction between FBXW7 and DISC1. These methods may equally be considered to be methods for testing a candidate agent for an ability to increase expression level and/or decrease turnover of DISC1 protein.

Agents identified by such screening methods may have utility in the other aspects of the invention described here. For example, they may have therapeutic utility in the treatment or prophylaxis of pathological conditions, as described herein.

Broadly, then, the invention provides a method of screening for an agent capable of inhibiting binding between DISC1 and FBXW7, the method comprising providing a candidate agent; and testing the candidate agent for the ability to inhibit binding between (i) DISC1 or a fragment or analogue thereof, and (ii) FBXW7 or a fragment thereof.

Various methods will be apparent by which such testing can be performed.

In one embodiment the invention provides a method of testing a candidate agent for an ability to inhibit binding between DISC1 and FBXW7, comprising contacting the candidate agent with
 (i) a first binding member comprising
  (a) DISC1;
  (b) a fragment of DISC1 capable of binding to FBXW7; or
  (c) an analogue of (a) or (b) capable of binding to FBXW7 and inhibiting binding between FBXW7 and DISC1; and
 (ii) a second binding member comprising FBXW7 or a fragment thereof capable of binding to DISC1;
 and determining the binding between (i) and (ii).

Typically, the method will involve the steps of determining binding between the first and second binding members in the presence and the absence of the candidate agent. A decreased level of binding in the presence of the candidate agent, as compared to the level of binding seen in the absence of the candidate agent, indicates that the candidate agent is capable of inhibiting binding between DISC1 and FBXW7.

The first binding member may comprise or consist of an FBXW7-binding moiety or antagonist as described elsewhere in this specification.

A candidate agent may inhibit binding between DISC1 and FBXW7 by binding FBXW7, or by binding DISC1 or a fragment thereof. For example, a candidate agent may be a fragment of FBXW7 capable of binding DISC1. More typically, though, the candidate agent may be a fragment of DISC1 or an analogue thereof, such as an FBXW7-binding moiety or antagonist as described elsewhere in this specification. Thus, the method may be used to compare the FBXW7-binding properties of two such FBXW7-binding moieties or antagonists.

The method may comprise the step of testing the ability of the candidate agent to increase expression level and/or decrease turnover of DISC1 protein. This may comprise:
 (i) providing a system comprising DISC1, FBXW7 and a ubiquitin-proteasome system, in which DISC1 can be degraded via said ubiquitin-proteasome system;
 (ii) contacting said system with the candidate agent; and
 (iii) determining DISC1 level, degradation and/or turnover.

DISC1 expression, degradation or turnover may be determined in the presence and absence of the candidate agent and the results compared.

The method may comprise the steps of testing a plurality of candidate agents and optionally selecting one or more candidate agents having the ability to inhibit binding between DISC1 and FBXW7.

The invention further provides a method of optimising an FBXW7-binding moiety for the ability to inhibit binding between DISC1 and FBXW7, comprising
 (i) providing a parent FBXW7-binding moiety capable of inhibiting binding between DISC1 and FBXW7,
 (ii) preparing or providing a variant of the parent FBXW7-binding moiety,
 (iii) testing the variant FBXW7-binding moiety for the ability to inhibit binding between DISC1 and FBXW7; and optionally
 (iv) comparing the ability of the parent and variant FBXW7-binding moieties to inhibit binding between DISC1 and FBXW7.

The comparison may be direct. For example, the assay may be performed in a competitive format as set out above, in which both the parent and variant are contacted simultaneously with FBXW7.

Alternatively the ability of the parent and the variant may be tested separately and the results compared, or the ability of the variant may be compared to a pre-determined level of binding for the parent FBXW7-binding moiety. The ability of the parent and of the variant will typically have been determined under comparable or identical conditions.

The step of preparing or providing the variant FBXW7-binding moiety may comprise modifying the parent FBXW7-binding moiety in order to prepare the variant FBXW7-binding moiety. Where the parent FBXW7-binding moiety comprises a peptide, peptoid or protein, the variant may be produced by modification (e.g. substitution, deletion or addition) of one or more amino acids or analogues thereof compared to the parent sequence.

The method may comprise the steps of preparing or providing a plurality of variant FBXW7-binding moieties and optionally selecting one or more variant FBXW7-binding moieties having the ability to inhibit binding between DISC1 and FBXW7, e.g. having superior such activity as compared to the parent FBXW7-binding moiety.

In any of the screening methods described herein, the candidate agent or FBXW7-binding moiety may be a small molecule (i.e. a compound having a molecular mass of 900 Da or less), a peptide, polypeptide or peptidomimetic (such as a peptoid), or may be any other suitable compound, and may be an antagonist or FBXW7-binding moiety as described herein.

For the purposes of the testing or screening methods described herein, FBXW7 and DISC1 (or the fragment of analogue thereof) form a specific binding pair which interact specifically with one another.

Either member of the binding pair may be immobilised on a solid phase (e.g. a solid support) and contacted with a sample containing the other member of the binding pair. The candidate agent may then be introduced before, concurrently with, or after the sample containing the member of the binding pair which is not immobilised on a solid phase.

Whether or not a member of the binding pair is immobilised, one or both members, or another component of the assay, may be labelled in order to facilitate detection of binding.

Any suitable format may be used for the assay, including high-throughput formats. The skilled person is aware of numerous suitable formats for such screening assays, and can select an appropriate format depending on their requirements. Suitable formats include fluorescence polarisation (FP) and isothermal titration calorimetry (ITC) assays. Sample protocols are provided in the Examples.

In a further aspect, the invention provides a method of determining whether a patient will respond to treatment with an antagonist of the interaction between DISC1 and FBXW7, comprising the steps of
 (i) isolating a sample from a patient,
 (ii) contacting the sample with an antagonist capable of inhibiting the interaction between DISC1 and FBXW7, and
 (iii) comparing expression level, degradation and/or turnover of DISC1 protein in the presence and absence of the antagonist, where an increase in expression level, or decrease in degradation and/or turnover of DISC1 is a positive indicator that the patient will respond to treatment with the antagonist.

The invention will now be described in more detail, by way of example and not limitation, by reference to the accompanying drawings. Many equivalent modifications and variations will be apparent to those skilled in the art when given this disclosure. Accordingly, the exemplary embodiments of the invention set forth are considered to be illustrative and not limiting. Various changes to the described embodiments may be made without departing from the scope of the invention. All documents cited herein are expressly incorporated by reference.

The present invention includes the combination of the aspects and preferred features described except where such a combination is clearly impermissible or is stated to be expressly avoided.

Section headings are used herein are for convenience only and are not to be construed as limiting in any way.

DESCRIPTION OF THE FIGURES

FIG. 4: Mass spectroscopic analysis of DISC1 immunoprecipitation identifies ubiquitination sites. Figure discloses SEQ ID NOS 85-87, respectively, in order of appearance.

FIG. 7: (A) Comparison of DISC1 sequence with phospho-degron motifs in known targets of FBXW7 (SEQ ID NOS 88-94, 104, and 95, respectively, in order of appearance); (B) cross-species alignment of DISC1 sequence illustrating conservation of the phospho-degron motif (SEQ ID NOS 95-104, respectively, in order of appearance).

FIG. 8: DISC1 and FBXW7 co-immunoprecipitate in cells.

DETAILED DESCRIPTION OF THE INVENTION

Figure 1:
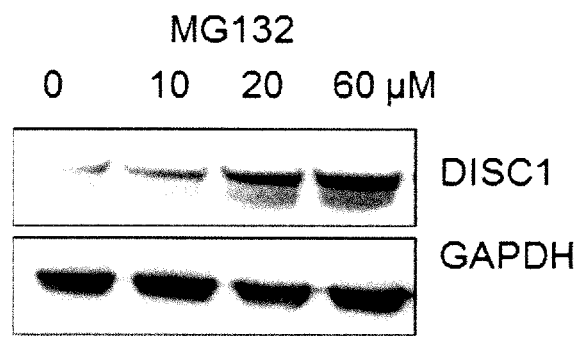
FIG. 1: The proteosome inhibitor MG132 up-regulates DISC1 levels in HEK293 cells.

The DISC1 gene has been discovered at one breakpoint of a t(1;11) chromosomal translocation that segregates with schizophrenia (SZ), bipolar disorder (BP) and recurrent major depressive disorder (rMDD) in a Scottish family [5]. Since then, DISC1 has become widely recognised as one of the most convincing genetic risk factors for major mental illness. Moreover, the DISC1 interactome [6] includes several self-standing risk factors, including PDE4B and D, NDE1, PCM1, and GSK3b. Thus, DISC1 and its core partner proteins impact directly on disease relevant biological pathways [2]. The t(1;11) translocation remains one of the very few unequivocally causal genetic events identified for major mental illness to date.

Using lymphoblastoid cell lines derived from t(1;11) family members it has been demonstrated that the translocation reduces DISC1 expression at both the transcript and protein level [7]. DISC1 haploinsufficiency is consequently likely to be a major component of the disease mechanism. Moreover, it has been shown that aberrant chimeric DISC1 transcripts are also present [8]. These rare transcripts encode aberrant chimeric DISC1 protein species, although the existence of such species remains to be demonstrated. Nonetheless, if present even at very low levels, it is possible that aberrant DISC1 protein species are another component of the disease mechanism.

In addition to the t(1;11) translocation, an inherited deletion targeting DISC1 has been identified in an autistic child [9], a duplication targeting DISC1 has been reported in two autistic brothers, one additionally diagnosed with attention-deficit hyperactivity disorder (ADHD) [10], and additional duplications/deletions affecting DISC1 may be present in patients diagnosed with schizophrenia or intellectual disability. These copy number variants are all predicted to alter expression levels of wild-type DISC1. Modulating wild-type DISC1 expression levels may therefore represent a possible route to successful intervention.

The importance of the DISC1 signalling "node" to brain development, brain function and behaviour has been highlighted in studies that achieved transient silencing of DISC1. Additionally, it has been recognized that DISC1 protein levels fluctuate during neurodevelopment, with "peaks" at critical stages such as the neurogenesis period and postnatally [14]. In light of this, it is surprising that nothing is known about how cells regulate DISC1 turnover. Understanding how the DISC1 protein is regulated and degraded could provide important insights into the disease process and assist with modulation of the protein's expression level.

Protein degradation by the proteosome and lysosome is a dynamic process that has been shown to be crucial for neurodevelopment, synaptic plasticity and neuron self-renewal. Indeed, the balance between protein synthesis and degradation in neurons is now regarded as a control point for regulation of synaptic functions that underpin learning and memory [15]. Recent evidence suggests that the half-life of specific neuronal proteins can be profoundly influenced by synaptic activity [16], hence the stoichiometry of these proteins can be uniquely tailored in a manner that promotes memory formation. Crucial to this process, is the compartmentalization of protein turnover at the synapse, which maintains optimal levels of the evolutionary conserved macromolecular signalling complexes, which are required for neural development or synaptic transmission.

The inventors have now found that DISC1 levels are tightly regulated by the ubiquitin proteosome system (UPS) via interactions with the F-box-containing protein FBXW7. Modulating the interaction between DISC1 and FBXW7 may therefore provide means to modulate expression levels of DISC1 and thereby ameliorate the symptoms or pathogenesis of intellectual disability and/or neuropsychiatric disorders, including schizophrenia, bipolar disorder, depression, recurrent major depressive disorder (rMDD), attention-deficit hyperactivity disorder (ADHD) and autism DISC1
Human DISC1 protein has the sequence:

```
  1 MPGGGPQGAP AAAGGGGVSH RAGSRDCLPP AACFRRRRLA RRPGYMRSST GPGIGFLSPA

61 VGTLFRFPGG VSGEESHHSE SRARQCGLDS RGLLVRSPVS KSAAAPTVTS VRGTSAHFGI

121 QLRGGTRLPD RLSWPCGPGS AGWQQEFAAM DSSETLDASW EAACSDGARR VRAAGSLPSA

181 ELSSNSCSPG CGPEVPPTPP GSHSAFTSSE SFIRLSLGSA GERGEAEGCP PSREAESHCQ

241 SPQEMGAKAA SLDGPHEDPR CLSRPFSLLA TRVSADLAQA ARNSSRPERD MHSLPDMDPG

301 SSSSLDPSLA GCGGDGSSSS GDAHSWDTLL RKWEPVLRDC LLRNRRQMEV ISLRLKLQKL

361 QEDAVENDDY DKAETLQQRL EDLEQEKISL HFQLPSRQPA LSSFLGHLAA QVQAALRRGA

421 TQQASGDDTH TPLRMEPRLL EPTAQDSLHV SITRRDWLLQ EKQQLQKEIE ALQARMFVLE

481 AKDQQLRREI EEQEQQLQWQ GCDLTPLVGQ LSLGQLQEVS KALQDTLASA GQIPFHAEPP

541 ETIRSLQERI KSLNLSLKEI TTKVCMSEKF CSTLRKKVND IETQLPALLE AKMHAISGNH

601 FWTAKDLTEE IRSLTSEREG LEGLLSKLLV LSSRNVKKLG SVKEDYNRLR REVEHQETAY

661 ETSVKENTMK YMETLKNKLC SCKCPLLGKV WEADLEACRL LIQSLQLQEA RGSLSVEDER

721 QMDDLEGAAP PIPPRLHSED KRKTPLKVLE EWKTHLIPSL HCAGGEQKEE SYILSAELGE

781 KCEDIGKKLL YLEDQLHTAI HSHDEDLIQS LRRELQMVKE TLQAMILQLQ PAKEAGEREA

841 AASCMTAGVH EAQA (SEQ ID NO: 105)
```

(Accession no. Q9NRI5.3; GI: 160332362; created: Nov. 16, 2001;
sequence updated: Nov 13, 2007)

Chimpanzee (*Pan troglodytes*) DISC1 protein has the sequence:

```
  1 MPGGGPQGAP AAAGGGGVSH RAGSRDCLPP AACFRRRRLA RRPGYMRSST GPGIGFLSPA

61 VGTLFRFPGG VSGEESHHSE SRARQCGLDS RGLLVRNPVS KSAAAPAVTS VRGTSAHFGI

121 QLRGGTRLPD RLSWPCGPGN AGWQQEFAAM DSSEILDASW EAACSGGARR VRAAGSLPSA

181 ELSSNSCSPG CGPEAPPTPP DSHSAFTSSF SFIRLSLGSA GERGEAEGCL PSREAESHCQ

241 SPQEMAAKAA SLDGPHEDPR CLSRPFSLLA TRVSADLAQA ARNSSRPERD MHPLPDMDPG

301 SSSSLDPSLA GCGGDGSSSS GDAHSWDTLL RKWEPVLRDC LLRNRRQMEV ISLRLKLQKL

361 QEDAVENDDY DKAETLQQRL EDLEQEKISL HFQLPSRQPA LSSFLGHLAA QVQAALCRGA

421 TQQASRDDTH TSLRMEPRLL EPTAQDSLHV SITRRDWLLQ EKQQLQKEIE ALQARMFVLE

481 AKDQQLRREI EEQEQQLQWQ GCDLTPLVGQ LSLGQLQEVS KALQDTLASA GQIPFHAEPP

541 ETIRSLQERI KSLNLSLKEI TTKVCMSEKF CSTLRKKVND IETQLPALLE AKMHAISGNH

601 FWTAKDLTEE IRSLTSEREG LEGLLSKLLV LSSRNVKKLG SVKEDYDRLR REVEHQETAY

661 ETSVKENTMK YMETLKNKLC SCKCPLLGKV WEADLEACRL LIQSLQLQEA RGSLSVEDER

721 QMDDLEGAVC IAAPPIPPRL HSEDKRKTPL QALEEWKAHL IPSLHCAGGE QKEESYILSA

781 ELGEKCEDIG KKLLYLEDQL HTAIHSHDED LIQSLRRELQ MVKETLQAMI LQLQPAKEAG

841 EREAAASCMT AGVHEAQA (SEQ ID NO: 106)
```

(Accession no. JAA04775.1 GI: 410215112)

Macaque (*Macacca mulata*) DISC1 protein has the sequence:

```
  1 MPGGGPQGAP AAAGGGGVGH RAGSRDCLPP AACFRRRRLA RRPGYMRSST GPGIGFLSPA

61 VGTLFRVPGG VPGEESHHSE SKTRECGLDS RGLLVGSPVS KSAAAPAVTS VRGTSAHFGI

121 QLRGGTRLPD RLSRLCGPGN AGWQQEFAAM DSSETLDTSW EAACSDGARR VQAAGSVPSA

181 ELSSNSCNPG CGLEDPPTPP GSHSAFASSF SFIRLSLGSA GERGEAEGCP PSREAESPCQ

241 SPQEMGAKAA SLDGPHKDPR CLSRPFSLLA TQVSEDLAQA AGNSSRPECE MHSLPDMDSG

301 SSSSLDPSLA GCGGDGSSGS GDAHSWDTLL RKWEPVLRDC LLRNRRQMEV ISLRLKLQKL

361 QEDAVENDDY DKAETLQQRL EDLEQEKINL HFQLPSRQRA LSSFLGHLAA QVQAALRRGA
```

-continued

```
421 TQQASGDDTH ASLRTEPRLL ECTAQDSLHV SITRRDWLLQ EKQQLQKEIE ALQARMSVLE

481 AKDQQLRREI EEKEQQLRWQ GCDLTPLVGR LSLGQLREVS KALQDTLASA GQIPFHAEPP

541 ETIRSLQERI KSLNLSLKEI TTKVCMSEKF CSTLRKKVND IETQLPALLE AKMHAISGNH

601 FCTAKDLTEE IRSLTSEREG LEGLLSKLLV LSSRNVKKLG SVKEDYDRLR REVEHQETAY

661 ETSMKENTMK YMETLKDKLC SCKCPLLGKV WEADLEACRL LMQSLQLQEA RGSLSVEDER

721 QMDALEGAAP PITPRLHSED KRKTPLQALE EWKAHLIPSL YCAGGEQKEE SYILSAELGE

781 KCEDIGKKLL YLEDQLHTAI HSHDEDLIQS LKRELQMVKE TLQAMILQLQ PAKEAGEREA

841 AASCMTAGVH EAQA (SEQ ID NO: 107)
```

(Accession no. AAV87214.1 GI: 56405456)
Mouse (*Mus musculus*) DISC1 has the sequence:
```
  1 MQGGGPRDAP IHSPSHGADS GHGLPPAVAP QRRRLTRRPG YMRSTAGSGI GFLSPAVGMP

61 HPSSAGLTGQ QSQHSQSKAG QCGLDPGSHC QASLVGKPFL KSSLVPAVAS EGHLHPAQRS

121 MRKRPVHFGV HSKNDSRQSE KLTGSFKPGD SGCWQELLSS DSFKSLAPSL DAPWNTGSRG

181 LKTVKPLASS ALNGPADIPS LPGFQDTFTS SFSFIQLSLG AAGERGEAEG CLPSREAEPL

241 HQRPQEMAAE ASSSDRPHGD PRHLWTFSLH AAPGLADLAQ VTRSSSRQPE CGTVSSSSDT

301 VFSSQDASSA GGRGDQGGGW ADAHGWHTLL REWEPMLQDY LLSNRRQLEV TSLILKLQKC

361 QEKAVEDGDY DTAETLRQRL EELEQEKGHL SWALPSQQPA LRSFLGYLAA QIQVALHGAT

421 QRAGSDDPEA PLEGQLRTTA QDSLPASITR RDWLIREKQQ LQKEIEALQA RMSALEAKEN

481 RLSQELEEQE VLLRWPGCDL MALVAQMSPG QLQEVSKALG ETLTSANQAP FHVEPPETLR

541 SLRERTKSLN LAVRELTAQV CSGEKLCSSL RRRLSDLDTR LPALLEAKML ALSGSCFSTA

601 KELTEEIWAL SSEREGLEMF LGRLLALSSR NSRRLGILKE DYLRCRQDLA LQDAAHKTRM

661 KANTVKCMEV LEGQLSSCRC PLLGRVWKAD LETCQLLMQS LQLQEAGSSP HAEDEEQVHS

721 TGEAAQTAAL AVPRTPHPEE EKSPLQVLQE WDTHSALSPH CAAGPWKEDS HIVSAEVGEK

781 CEAIGVRLLH LEDQLLGAMY SHDEALFQSL QGELQTVKET LQAMILQLQP TKEAGEASAS

841 YPTAGAQETE A (SEQ ID NO: 108)
```

(Accession no. AAN77091.1 GI: 25992176)
Rat (*Rattus norvegicus*) DISC1 has the sequence:
```
  1 MQGAGSRGAW IHSPSHCPGN GHGSPPAVAP QRRRLTRRPG YMRSTASPGI GFLSPAVGMP

61 RPISAGLTGQ EFYPSQSKAR QCSLDLRSHC QDSLVGNPFL KGSLGPAVTS VGHLHPAQGS

121 MRERMVHSGV HSGNDRRQSE RLTGDSGCRQ EFLSSDSSKS LASSLDVAWS KGSRGLKTVR

181 PLVSPASNGP VDIPSLPGFQ DTFTSNFSFI RLSLGAAGER GEAEGCLPSR EAEPLHQSPQ

241 EMAAEGSGSD RPHGEPRHLW TFSLHAAPGL VDLAQGTRSN RQPECGMVSS SDAGFSSQDA

301 SPAGGRSDQD GGWADAHGWH ALLREWEPML QDYLLSNRRQ LEVTSLILKL QKLQEKAVED

361 GDYDMAETLR QRLEDLEQEK GRLPWALPSQ QPALRSFLGY LATQTHAALH GAPQRAGSDD

421 PEAPLEGQRR TTAQDSLPGL AVTRRDWLMR EKEQLQKEIE ALRARVSVLE AKEQRLSQEL

481 EDQEMLLRWQ GCDQMALVAQ LSPGQLQEVS KALGETLTSA RWAPFRVEPP ETLRSLRERT

541 KSLDLAVREL TEQVCSGEKL CSSLRKRLAD LDTRLPALLE AKMLALSGSC FSTAKELAEE

601 IWAVSSEREG LEMFLGRLLA LSSRNTRRLG SVKEDYLRCR QDLALQEAAH KTRVKANTVK

661 CTEVLEGQLS CCRCPLLERV WKADLEACQL LMQSLEIQEA GSSSHVEDEK QVHSTGEAAQ

721 TAALAVPRTP HPEEEKSPLQ ESHVVFAEVG DKCEAIGMRL LHLEDQLLGA MHGHDEALFH

781 SLQGELQMVK ETLQTMFLQL QPAKEAGGEA SASYSTAGAQ EAED (SEQ ID NO: 109)
```

-continued (Accession no. EDL96753.1 GI: 149043221)
Zebrafish (*Danio rerio*) DISC1 has the sequence:

```
  1 MMFAGMVRVE NTSKTLKTDI DSPCHRCAVR TGGVNPSGNH RRRSFRRPGY MRSEPINQLD

61 VAETSCDSEH HRSPISKSPA VENTQKSASE LLGEKWLTEG FERDNSSKSS NKHHLHDEED

121 NLPVQSRDVF NSSFSFIQQS LDTSDLLDVN TCYSPRTEHK QSESASGHQL KSKTSNSGEL

181 NPPSDLMNHL SQSETSIVQM NQLETRTVPV SQSKSSFLKP LSALMNHLSQ SETTSVPINQ

241 SETSSAPKSQ SNSGFLKPLS DLMKHLTPPE SSIVLMNQSE TITIPMNQTK NSTIPVSQSN

301 ADFLNPPSAL MNHLNQSETV LIPMNQSETS SIPVSQSNSG FLKPSSNLIN HLSQSESVTV

361 PMNQSETSTV SLSQSEPDFF SLRHLPCSIG QSAQQKGLLL DRELWLVDLD LQTSSSIMSK

421 YTKENIQDSD SGSLDAEITS SHSIDSSDST SSGYESTTPS SDQSQDGLMK KYEDFLQDCL

481 QNNRTNTKIE SIMMKLQRLQ HKAILDDDYD TAERFGKKLE ELRRERATLK PGLPSRHPEV

541 TGYLERLRTA VNSAIHRTDS DCSTGDPSED QRSCISQSRA QTRETLLEEK QRIQKEMCDV

601 QRRLRDLQER SRALELQLEL QEMQGPVLRA ADSPHLHLTA RALEDLLTSE HRQRISVSPP

661 AHIRRLEEQE RVLSLSIREA ETKVLLNQRL CFSLRQKVSE SETQLLALHE AKLTAVSGND

721 FSSAKELKAE IRSVYRERDR LELLHRKLQT LSTGSGLDLS RMKEKHKHIK LELQNGEAQY

781 ERSLKENTVK YIELLEDKLH SCGSAALEHV LEADLEACHL LLKGLDQRNL SLSQTEDLPS

841 GSASASDVLQ FTKDEEDCAM LTALGGRWCP EADLQHSQFT KNLEEFLFCL EDEAPENLCG

901 ETTELTERCE LISYRLHYLE EQLQTAIDNN DKELTLSLER EVLELKSALQ AMLSQLKEED

961 EDEEDEEKYC DVEEEQVEDE DLEEEHYFSD SWEI (SEQ ID NO: 110)
```
(Accession no. NP_001135735.1 GI: 214010133)

As well as FBXW7, DISC1 is known to bind to a number of targets including PDE48 and Nude11

As used in this specification, the term DISC1 is intended to embrace the human protein and those from chimpanzee, monkey, mouse, rat and zebrafish shown above, as well as their homologues (especially orthologues) in other species, and variants (e.g. splice variants) and derivatives thereof which retain the capacity to bind FBXW7.

Such variants and derivatives preferably have at least about 75%, 80%, 85%, 90% or 95% sequence identity to one of the reference sequences shown above, e.g. to the human, chimpanzee or monkey protein sequence.

In particular, conservative substitutions in the DISC1 sequence may be particularly well tolerated, without substantial effect on function.

Fragments of DISC1 (or of its variants and derivatives as described above) which are capable of binding to FBXW7 may also find use in the present invention.

The DISC1 fragment itself may comprise at least 5, 6, 7, 8, 9, 10, 12, 15, 20, 25, 30, 35, 40, 45, 50 or more consecutive amino acids of DISC1. It may comprise up to 100, 200, 300, 400, 500, 600, 700 or 800 amino acids of DISC1.

Additionally or alternatively, the DISC1 fragment may have a maximum length of 5, 6, 7, 8, 9, 10, 15, 20, 25, 30, 35, 40, or 50 amino acids, although it may be longer.

DISC1 molecules, and variants, derivatives and fragments thereof which find use in the present invention retain the ability to bind FBXW7. They comprise a phospho-degron motif, which may be the human motif $P_{197}$-$T_{198}$-$P_{199}$-$P_{200}$-$G_{201}$-$S_{202}$-$H_{203}$ (SEQ ID NO: 111) or the corresponding sequence from a DISC1 molecule from another species (e.g. one of the corresponding sequences shown in FIG. 7B, especially those from chimpanzee, monkey, dog, horse, mouse, rat or zebrafish) or a fragment thereof capable of binding to FBXW7. Such phospho-degron motifs and fragments thereof may conform to Formula I as shown above.

FBXW7
Human FBXW7 protein has the sequence:

```
  1 MNQELLSVGS KRRRTGGSLR GNPSSSQVDE EQMNRVVEEE QQQQLRQQEE EHTARNGEVV

61 GVEPRPGGQN DSQQGQLEEN NNRFISVDED SSGNQEEQEE DEEHAGEQDE EDEEEEEMDQ

121 ESDDFDQSDD SSREDEHTHT NSVTNSSSIV DLPVHQLSSP FYTKTTKMKR KLDHGSEVRS

181 FSLGKKPCKV SEYTSTTGLV PCSATPTTFG DLRAANGQGQ QRRRITSVQP PTGLQEWLKM

241 FQSWSGPEKL LALDELIDSC EPTQVKHMMQ VIEPQFQRDF ISLLPKELAL YVLSFLEPKD

301 LLQAAQTCRY WRILAEDNLL WREKCKEEGI DEPLHIKRRK VIKPGFIHSP WKSAYIRQHR

361 IDTNWRRGEL KSPKVLKGHD DHVITCLQFC GNRIVSGSDD NTLKVWSAVT GKCLRTLVGH

421 TGGVWSSQMR DNIIISGSTD RTLKVWNAET GECIHTLYGH TSTVRCMHLH EKRVVSGSRD
```

```
481 ATLRVWDIET GQCLHVLMGH VAAVRCVQYD GRRVVSGAYD FMVKVWDPET ETCLHTLQGH

541 TNRVYSLQFD GIHVVSGSLD TSIRVWDVET GNCIHTLTGH QSLTSGMELK DNILVSGNAD

601 STVKIWDIKT GQCLQTLQGP NKHQSAVTCL QFNKNFVITS SDDGTVKLWD LKTGEFIRNL

661 VTLESGGSGG VVWRIRASNT KLVCAVGSRN GTEETKLLVL DFDVDMK
    (SEQ ID NO: 112)
(Accession no. AAI43945.1 GI: 219518973)
```

As used in this specification, the term FBXW7 is intended to embrace this human protein as well as its homologues (especially orthologues) in other species, and variants, derivatives and fragments thereof which retain the capacity to bind DISC1. Such molecules may also retain the ability to bind other known binding partners of FBXW7 such as cyclin E, Notch, c-Myc, etc.

Such variants and derivatives preferably have at least about 80%, 85%, 90% or 95% sequence identity to the human protein sequence.

In particular, conservative substitutions in the FBXW7 sequence may be particularly well tolerated, without substantial effect on function.

Fragments of FBXW7 (or of its variants and derivatives) which are capable of binding to DISC1 may also find use in the present invention.

The FBXW7 fragment itself may comprise at least 5, 6, 7, 8, 9, 10, 12, 15, 20, 25, 30, 35, 40, 45, 50, 100, 150, 200, 250, 300, 350, 400, 450, 500, 550, 600, 650 or more consecutive amino acids of FBXW7.

Additionally or alternatively, the FBXW7 fragment may have a maximum length of 5, 6, 7, 8, 9, 10, 15, 20, 25, 30, 35, 40, 50, 100, 150, 200, 250, 300, 350, 400, 450, 500, 550, 600 or 650 amino acids, although it may be longer.

In assays making use of an FBXW7 molecule and a DISC1 molecule, it may be desirable that they are derived from the same species.

FBXW7 may be purified from any suitable source, or may be expressed recombinantly.

FBXW7 may be expressed and/or used in conjunction with SKP1 or a functional fragment thereof. SKP1 may, for example, have the sequence of human SKP1:

```
  1 MPSIKLQSSD GEIFEVDVEI AKQSVTIKTM LEDLGMDDEG DDDPVPLPNV NAAILKKVIQ

61 WCTHHKDDPP PPEDDENKEK RTDDIPVWDQ EFLKVDQGTL FELILAANYL DIKGLLDVTC

121 KTVANMIKGK TPEEIRKTFN IKNDFTEEEE AQVRKENQWC EEK (SEQ ID NO: 113)
(Accession no. AAH20798.1 GI: 18089150)
``` or may have at least 80%, 85%, 90% or 95% sequence identity therewith. By a functional fragment is meant a fragment of SKP1 which retains the ability to induce correct folding of FBXW7 such that FBXW7 is capable of binding to DISC1.

Thus, FBXW7 may be co-expressed with SKP1 or a functional fragment thereof, e.g. as a fusion protein with SKP1 or a functional fragment thereof.

SKP1 may be present with FBXW7 (e.g. as a fusion protein with FBXW7) in assays and methods of the present invention if desired.

It may be useful in ensuring appropriate interaction between FBXW7 and DISC1. Ideally, the SKP1 molecule or fragment thereof is derived from the same species as the FBXW7.

Antagonists of the Interaction Between DISC1 and FBXW7

The antagonists described in this specification comprise an FBXW7-binding moiety.

The FBXW7-binding moiety may be a protein moiety. The term "protein" does not here imply any particular maximum or minimum size for the FBXW7-binding moiety. It merely signifies that the FBXW7-binding moiety is proteinaceous in nature, i.e. composed of amino acids linked by peptide bonds. It is not restricted to the 20 amino acids encoded by the mammalian genetic code) which will be referred to here as "naturally occurring" or "proteinogenic" amino acids but encompasses post-translationally modified (e.g. phosphorylated) derivatives of the naturally-occurring amino acids as well as non-naturally occurring amino acids including D-amino acids, N-methylated residues, and N-substituted glycine residues. It will also be understood that the term is intended to encompass protein derivatives such as glycoprotein and lipoprotein moieties, although the carbohydrate and lipid moieties of such molecules may be regarded as "heterologous components".

The FBXW7-binding moiety may comprise or consist of a DISC1 molecule or a variant, derivative or fragment thereof as described above which retains the ability to bind FBXW7.

Additionally or alternatively, the FBXW7-binding moiety may comprise or consist of a core sequence of 4 to 7 amino acids which conforms to Formula I as described above. It will be recognised that this includes a number of the wild-type phospho-degron sequences shown in FIG. 7B and fragments thereof.

In addition to the core sequence of Formula I, the FBXW7-binding moiety may comprise further flanking protein sequence N- and/or C-terminal of the core sequence. The flanking sequence may be derived from a DISC1 molecule.

Depending on the activity for which they are to be used, the antagonist may comprise one or more heterologous components. Heterologous components are components of the molecule which perform a function other than binding to FBXW7 or other generally-recognised functions of DISC1. Thus, any portion of protein sequence which is not core sequence and does not have recognisable identity to a corresponding sequence of a DISC1 molecule (e.g. has no more than 50%, e.g. no more than 25% sequence identity with any stretch of DISC1 sequence of the same length) may be regarded as a heterologous component, especially if it has an identifiable function unrelated to FBXW7 binding or other normal cellular functions of DISC1.

For example, the heterologous component may modulate a property of the antagonist such as stability, activity, immunogenicity, solubility, bioavailability, membrane permeability, ability to cross the blood brain barrier or localisation. For example, the heterologous component may be used to increase or reduce half-life in vitro or in vivo. The heterologous component may be protein, lipid, carbohydrate etc.

For antagonists which are to be used in cell-free systems, such as cell-free assays for FBXW7 binding, the size of the molecule may be relatively unimportant. Thus the FBXW7-binding moiety may be an entire DISC1 molecule, antibody specific for FBXW7, etc.

The FBXW7-binding moiety may comprise or consist of at least 5, 6, 7, 8, 9, 10, 15, 20, 25, 30, 35, 40, 45, 50 or more amino acids.

However, FBXW7 is an intracellular molecule, so it may be desirable that antagonists for use in vivo, or in cellular assays in vitro, are smaller than an entire DISC1 molecule. Smaller molecules may be more likely to pass across cell membranes or the blood brain barrier.

Thus it may be desirable that the FBXW7-binding moiety has a maximum length of 5, 6, 7, 8, 9, 10, 15, 20, 25, 30, 35, 40, or 50 amino acids.

Indeed, it may be desirable that the protein component of the antagonist molecule (i.e. FBXW7-binding moiety plus any protein heterologous components) may have a maximum length of 5, 6, 7, 8, 9, 10, 15, 20, 25, 30, 35, 40, or 50 amino acids.

It may also be desirable that any non-protein heterologous component (e.g. lipid, carbohydrate, etc.) has a maximum molecular weight of 1000 Da, 750 Da, 500 Da, 400 Da or even less. For example, cholesterol has a molecular weight of approximately 387, while a stearoyl group has a molecular weight of approx. 268.

Substitutions and Sequence Identity

A conservative substitution may be defined as a substitution within an amino acid class and/or a substitution that scores positive in the BLOSUM62 matrix.

According to one classification, the amino acid classes are acidic, basic, uncharged polar and nonpolar, wherein acidic amino acids are Asp (D) and Glu (E); basic amino acids are Arg (R), Lys (K) and His (H); uncharged polar amino acids are Asn (N), Gln (Q), Ser (S), Thr (T) and Tyr (Y); and non-polar amino acids are Ala (A), Gly (G), Val (V), Leu (L), Ile (I), Pro (P), Phe (F), Met (M), Trp (W) and Cys (C). The conventional one letter and three letter amino acid codes are used interchangeably in this specification.

According to another classification, the amino acid classes are small hydrophilic, acid/acid amide/hydrophilic, basic, small hydrophobic and aromatic, wherein small hydrophilic amino acids are Ser, Thr, Pro, Ala and Gly; acid/acidamide/hydrophilic amino acids are Asn, Asp, Glu and Gln; basic amino acids are His, Arg and Lys; small hydrophobic amino acids are Met, Ile, Leu and Val; and aromatic amino acids are Phe, Tyr and Trp Substitutions which score positive in the BLOSUM62 matrix are as follows:

Percent (%) amino acid sequence identity with respect to a reference sequence is defined as the percentage of amino acid residues in a candidate sequence that are identical with the amino acid residues in the reference sequence, after aligning the sequences and introducing gaps, if necessary, to achieve the maximum percent sequence identity, and not considering any conservative substitutions as part of the sequence identity. % identity values may be determined by WU-BLAST-2 (Altschul et al., Methods in Enzymology, 266:460-480 (1996)). WU-BLAST-2 uses several search parameters, most of which are set to the default values. The adjustable parameters are set with the following values: overlap span=1, overlap fraction=0.125, word threshold (T)=11. A % amino acid sequence identity value is determined by the number of matching identical residues as determined by WU-BLAST-2, divided by the total number of residues of the reference sequence (gaps introduced by WU-BLAST-2 into the reference sequence to maximize the alignment score being ignored), multiplied by 100.

Subjects for Treatment

Preferred subjects for treatment by the methods of the invention are mammals. Preferred subjects are primates (including humans), although the invention may extend to other animals including rodents (including mice and rats), and other common laboratory, domestic and agricultural animals (including but not limited to rabbits, dogs, cats, horses, cows, sheep, goats, etc.) especially when they represent models of human neuropsychiatric disorders.

Pharmaceutical Compositions and Methods of Treatment

The molecules described herein can be formulated in pharmaceutical compositions. These compositions may comprise, in addition to one of the above substances, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular and intraperitoneal routes. Examples of suitable compositions and methods of administration are provided in Esseku and Adeyeye (2011) and Van den Mooter G. (2006). Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Whatever the nature of the active agent that is to be given to an individual (e.g. a cell, polypeptide, nucleic acid

| Original Residue | C | S | T | P | A | G | N | D | E | Q | H | R | K | M | I | L | V | F | Y | W |
|---|---|---|---|---|---|---|---|---|---|---|---|---|---|---|---|---|---|---|---|---|
| Substitution | — | T A N | S | — | S | — | S D H | N E Q K | D Q K | N R Y K | Q K | E Y | I L R V | M L I V | M L I V V | M I V L | Y W | H F W | F Y | molecule, other pharmaceutically useful agent according to the present invention), administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

EXAMPLES

The Proteasome is Implicated in Turn-Over of DISC1

The proteasome inhibitor MG132 (N-carbobenzoxyl-Leu-Leu-Leucinal) (Sigma) was dissolved in DMSO to make a stock of 10 mM and stored at −20° C. HEK293 cells were treated with MG132 at various concentrations for 3 hours. The cells were then lysed in 3T3 lysis buffer (20 mM Hepes (pH 7.4), 50 mM NaCl, 50 mM NaF, 10% (v/v) glycerol, 1% (w/v) Triton X-100, 10 mM EGTA, 30 mM sodium pyrophosphate supplemented with protease and phosphatase inhibitor cocktail (Roche)). Proteins were quantified and normalised for protein concentration followed by Western blot analysis for DISC1 and GAPDH. Results are shown in FIG. 1.

Figure 2:
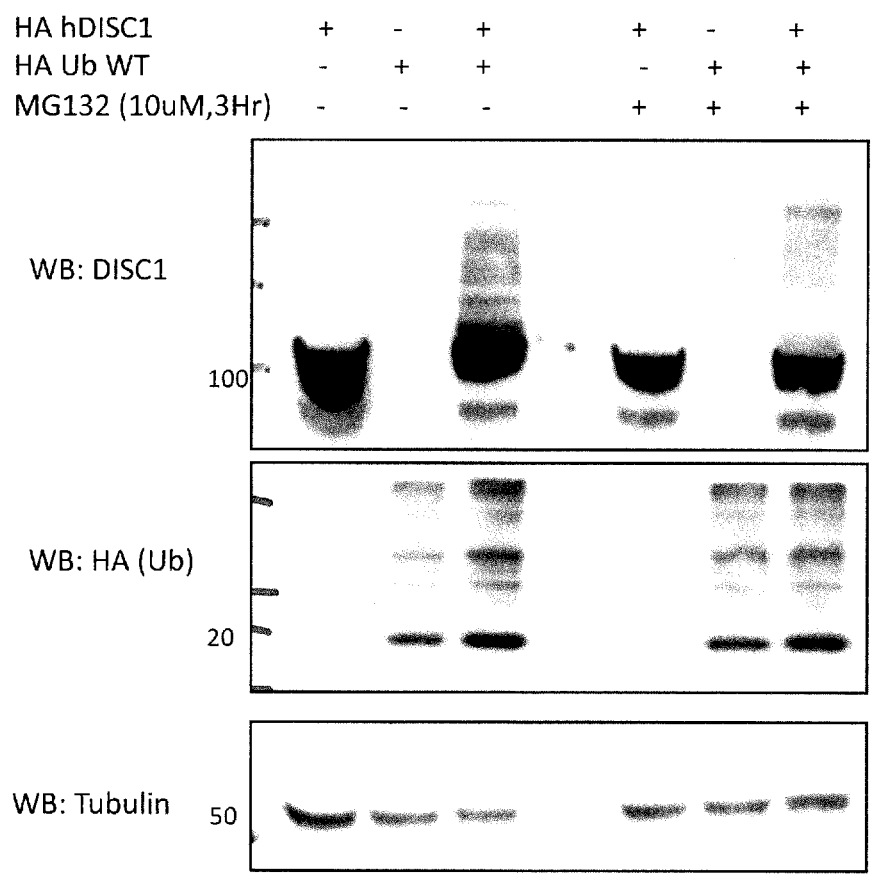
FIG. 2: HA-tagged DISC1 is ubiquitinated if overexpressed with ubiquitin.

DISC1 tagged with amino acids 98-106 of haemagglutinin (HA-DISC1) was overexpressed in HEK293 cells with an empty vector or HA-Ubiquitin. Samples were treated with DMSO or MG132 at a final concentration of 10 µM for 3 hr. Cells were lysed under denaturing conditions (described in materials and methods) and analysed for the presence of DISC1-Ubiquitin conjugates by Western blotting. Anti-DISC1 antibody was used to probe for DISC1 (native and Ub conjugate) Anti-tubulin was used as a loading control. Results are shown in FIG. 2.

Figure 3:
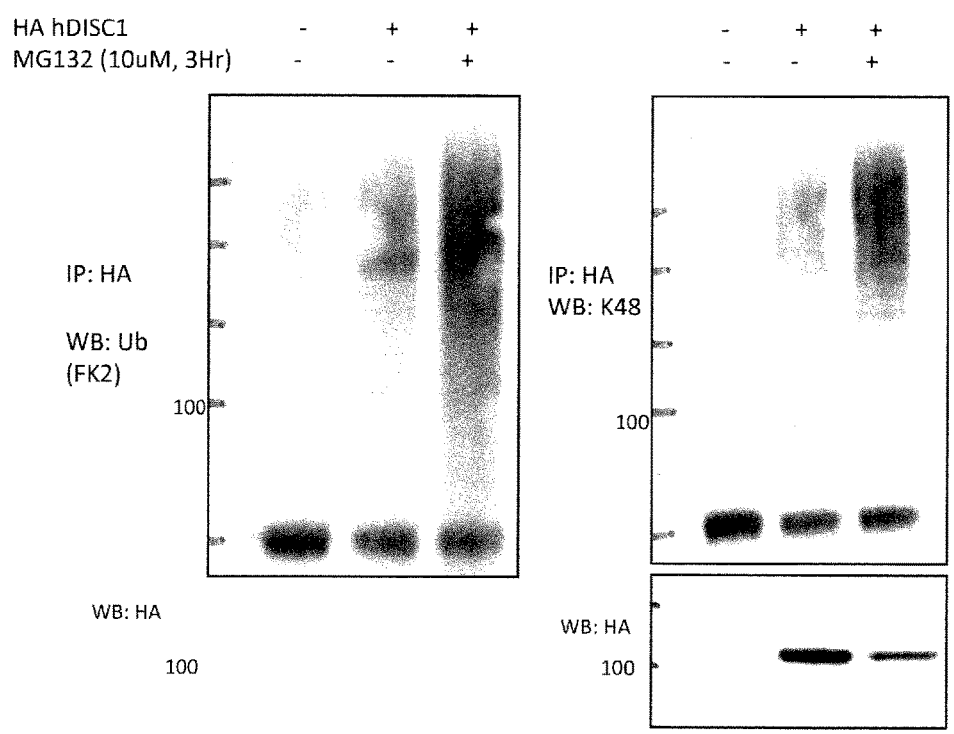
FIG. 3: HA-tagged DISC1 is modified by addition of K48-linked ubiquitin chains.

HA-DISC1 was overexpressed in HEK293 cells and treated with DMSO or MG132 at 10 µM (final concentration) for 3 hr. Cells were lysed under denaturing conditions and immunoprecipitation was performed using anti-HA-agarose beads or anti-mouse IgG-agarose beads (negative control). Captured immunoprecipitate complexes were analysed by Western blot. Results are shown in FIG. 3, in which the left panel shows blotting with anti-Ubiquitin and anti-DISC1; the right panel shows blotting with ubiquitin chain-specific antibody.

Samples were prepared to detect DISC1 ubiquitination in HEK293 cells by mass spectroscopy. Flag-DISC1-HA Ubiquitin complexes overexpressed in HEK293 cells were immunoprecipitated using anti-FLAG-agarose beads. Untransfected HEK293 cell lysate was used as a negative control. Samples were prepared, analysed and stained as described in Materials and Methods. Bands were excised and analysed by mass spectroscopy. See FIG. 4.

Ubiquitination of DISC1 is Mediated by FBXW7

Figure 5:
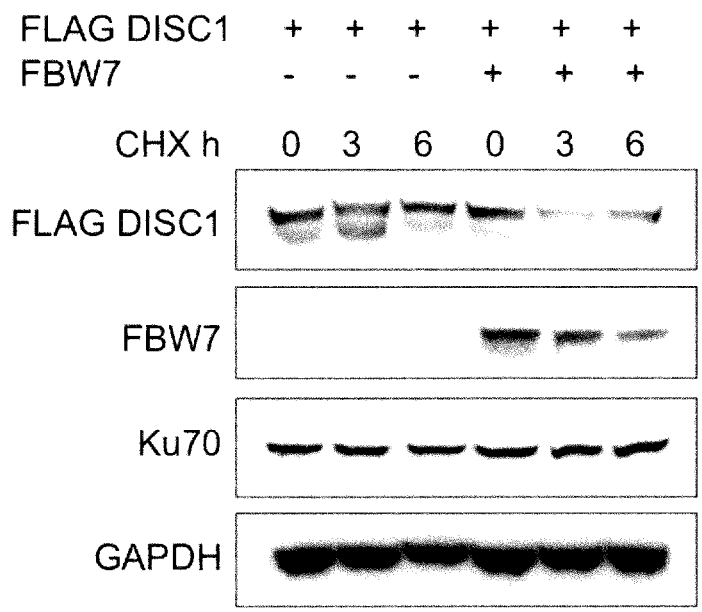
FIG. 5: Overexpression of FBXW7 increases degradation of DISC1.

FIG. 5 shows the effect of FBXW7 over-expression on the stability of FLAG-DISC1. FLAG-DISC1 was co transfected into HEK293 cells with untagged FBXW7 or an empty vector (negative control). Cells were treated with cycloheximide (CHX) at indicated concentrations and times (hours). Cell lysates were analysed by Western blotting using anti-DISC1 and anti-FBXW7 antibodies. Ku70 and GAPDH protein expression levels serve as loading controls as they are stable under CHX treatment. Results are shown in FIG. 5.

Figure 6:
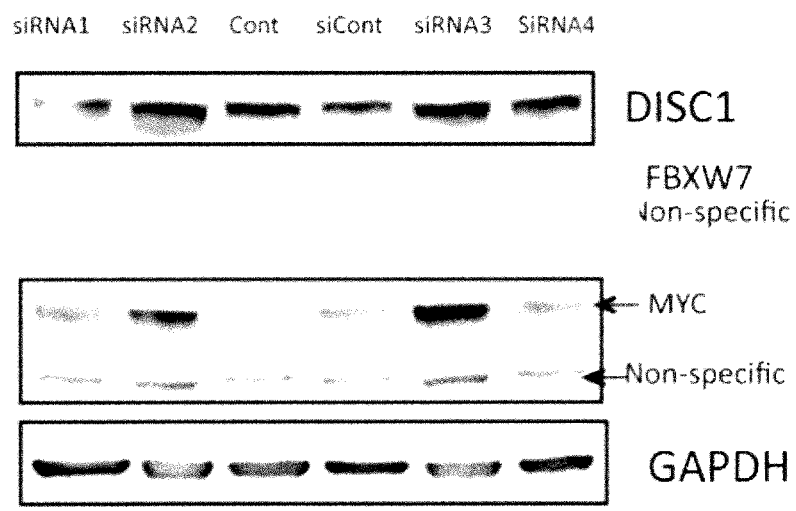
FIG. 6: Silencing of FBXW7 increases DISC1 expression (and other FBXW7 substrates).

FIG. 6 illustrates the effect of siRNA-mediated knockdown of FBXW7 on DISC1 protein levels. HEK293 cell cultures were individually transfected with 4 different siRNA (which constitute the SMART Pool used in the FBOX library screen) targeting different regions of the FBXW7 transcript. DISC1 (protein of interest), FBXW7 and c-Myc (known FBXW7 substrate) and GAPDH (loading control) expression levels were evaluated using anti DISC1, anti FBXW7, anti C-Myc and anti GAPDH antibodies respectively.

Analysis of the sequence of DISC1 reveals the presence of a likely phospho-degron motif. FIG. 7(A) shows an alignment of that motif with those from other proteins known to interact with FBXW7. FIG. 7(B) illustrates the conservation of that phospho-degron motif in DISC1 proteins from various different species.

FBXW7 and DISC1 Co-Immunoprecipitate in Cells

HEK293 cells were transiently co transfected with transfected with FLAG-tagged FBXW7 and GFP- or V5-tagged DISC1 using Polyfect transfection reagent (QIAGEN) according to manufacturer's protocol. After 48 hr of transfection, cells were lysed using ice cold 3T3 lysis buffer (20 mM Hepes (pH 7.4), 50 mM NaCl, 50 mM NaF, 10% (v/v) glycerol, 1% (w/v) Triton X-100, 10 mMEGTA, 30 mM sodium pyrophosphate and protease and phosphatase inhibitor cocktail (Roche)). Cell lysate concentration was normalised to 1 µg/µl followed by pre-clearing with protein A beads. Agarose beads carrying anti-FLAG antibodies (Sigma) were used to immunoprecipitate FLAG tagged FBXW7 protein. Negative control IP was performed by incubating equal amount of cell lysate with agarose beads carrying anti-VSV antibodies (Sigma). Cell lysates were incubated with agarose beads carrying anti-FLAG antibodies for 2 h at 4° C. Followed by centrifugation at 10,000 g for 1 min, beads were washed thrice with the lysis buffer. Immunoprecipitate complexes were then eluted in SDS PAGE sample buffer and subjected to SDS-PAGE and Western immuno-blotting with antibodies specific for FLAG, GFP and V5.

Results are shown in FIG. 8, confirming that the GFP- and V5-tagged DISC1 protein is immunoprecipitated with the FLAG-tagged FBXW7.

Identification of DISC1 Peptides Capable of Binding to FBXW7

Peptides derived from DISC1 and containing the putative phospho-degron motif were immobilised on membranes and screened for the ability to bind FBXW7. Detectable binding was obtained using the 24-mer peptide GPEVPPTPPGSH-SAFTSSFSFIRL (SEQ ID NO: 114). Phosphorylation at one or both of Thr198 and Ser202 was found to improve binding significantly.

Similar analysis using truncated versions of this peptide showed that at least the peptides P-pT-P-P-G-pS-H-S(SEQ ID NO: 115), P-P-pT-P-P-G-pS-H (SEQ ID NO: 116) and P-pT-P-P-G-pS-H (SEQ ID NO: 21) retain the ability to bind FBXW7.

The 7-mer peptide P-pT-P-P-G-pS-H (SEQ ID NO: 21) was used as the basis for further investigation. L- and D-forms of aspartic acid and glutamic acid (upper and lower case letters respectively) as well as N-methylated versions of each (designated "m") were incorporated at positions 198 and 202. Peptides found to retain or have improved binding to FBXW7 included:

Peptide 16: P-E-P-P-G-d-H (SEQ ID NO: 1);
Peptide 35: P-E-P-P-G-d-H (SEQ ID NO: 1);
Peptide 55: P-e-P-P-G-mE-H (SEQ ID NO: 2);
Peptide 64: P-E-P-P-G-mD-H (SEQ ID NO: 3);
Peptide 75: P-e-P-P-G-mE-H (SEQ ID NO: 2);
Peptide 79: P-e-P-P-G-mD-H (SEQ ID NO: 4);
Peptide 82: P-d-P-P-G-mE-H (SEQ ID NO: 5);
Peptide 90: P-d-P-P-G-mE-H (SEQ ID NO: 5);
Peptide 91: P-d-P-P-G-mE-H (SEQ ID NO: 5);
Peptide 139: G-mE-P-P-G-mE-H (SEQ ID NO: 6);
Peptide 142: G-mD-P-P-G-mE-H (SEQ ID NO: 7);
Peptide 147: G-e-P-P-G-mE-H (SEQ ID NO: 8);
Peptide 173: G-d-P-P-G-mE-H (SEQ ID NO: 9); and
Peptide 181: G-d-P-P-G-mE-H (SEQ ID NO: 9).

Panels of peptides incorporating further truncation and substitution have yielded (amongst others) the following peptides which retain or have improved binding to FBXW7:

A5 G-d-P-P-G-mE (SEQ ID NO: 13)
A12 G-d-P-P-Q-mE-H (SEQ ID NO: 14)
A13 G-d-P-P-q-mE-H (SEQ ID NO: 15)
A18 L-d-P-P-G-mE-H (SEQ ID NO: 16)
A22 G-A-P-P-G-mE-H (SEQ ID NO: 17)
A25 G-e-P-P-G-mE (SEQ ID NO: 18)
A26 e-P-P-G-mE-H (SEQ ID NO: 19)
A31 a-e-P-P-G-mE-H (SEQ ID NO: 20)
A40 P-pT-P-P-G-pS-H (SEQ ID NO: 21)
A45 G-mD-P-P-G-mE (SEQ ID NO: 22)
A51 a-mD-P-P-G-mE-H (SEQ ID NO: 23)
A52 G-mD-P-P-Q-mE-H (SEQ ID NO: 24)
A56 G-mD-P-p-G-mE-H (SEQ ID NO: 25)
A58 L-mD-P-P-G-mE-H (SEQ ID NO: 26)
A71 a-mE-P-P-G-mE-H (SEQ ID NO: 27)
A73 G-mE-P-P-q-mE-H (SEQ ID NO: 28)
A76 G-mE-P-p-G-mE-H (SEQ ID NO: 29)
A79 l-mE-P-P-G-mE-H (SEQ ID NO: 30)
A80 P-pT-P-P-G-pS-H (SEQ ID NO: 21)
A82 P-A-P-P-G-mE-H (SEQ ID NO: 31)
A85 P-d-P-P-G-mE (SEQ ID NO: 32)
A86 d-P-P-G-mE-H (SEQ ID NO: 33)
A97 P-d-p-P-G-mE-H (SEQ ID NO: 34)
A98 L-d-P-P-G-mE-H (SEQ ID NO: 35)
A99 l-d-P-P-G-mE-H (SEQ ID NO: 36)
A100 P-pT-P-P-G-pS-H (SEQ ID NO: 21)
A101 P-e-P-P-G-mD-H (SEQ ID NO: 37)
A102 P-A-P-P-G-mD-H (SEQ ID NO: 38)
A119 P-pT-P-P-G-pS-H (SEQ ID NO: 21)
A124 P-e-P-P-G-mE (SEQ ID NO: 39)
A130 a-e-P-P-G-mE-H (SEQ ID NO: 40)
A131 P-e-P-P-Q-mE-H (SEQ ID NO: 41)
A132 P-e-P-P-q-mE-H (SEQ ID NO: 42)
A135 P-e-P-p-G-mE-H (SEQ ID NO: 43)
A136 P-e-p-P-G-mE-H (SEQ ID NO: 44)
A137 L-e-P-P-G-mE-H (SEQ ID NO: 45)
A138 l-e-P-P-G-mE-H (SEQ ID NO: 46)
A139 P-pT-P-P-G-pS-H (SEQ ID NO: 21)
A144 P-E-P-P-G-mD (SEQ ID NO: 47)
A151 P-E-P-P-Q-mD-H (SEQ ID NO: 48)
A160 G-d-P-P-G-mE-H (SEQ ID NO: 9)
A161 a-d-P-p-G-mE-H (SEQ ID NO: 49)
A162 a-d-p-P-G-mE-H (SEQ ID NO: 50)
A163 a-d-p-p-G-mE-H (SEQ ID NO: 51)
A164 a-d-P-P-G-mE-h (SEQ ID NO: 52)
A165 a-d-P-P-a-mE-H (SEQ ID NO: 53)
A166 a-d-P-P-a-mE-H (SEQ ID NO: 54)
A168 a-d-P-p-a-mE-h (SEQ ID NO: 55)
A169 a-d-p-p-a-mE-h (SEQ ID NO: 56)
A170 G-d-P-p-a-mE-H (SEQ ID NO: 57)
A171 G-d-P-p-a-mE-h (SEQ ID NO: 58)
A172 G-d-p-p-G-mE-H (SEQ ID NO: 59)
A173 G-d-p-p-a-mE-H (SEQ ID NO: 60)
A174 G-d-p-p-G-mE-h (SEQ ID NO: 61)
A175 G-d-p-p-a-mE-h (SEQ ID NO: 62)
A176 a-d-P-p-a-mE-h (SEQ ID NO: 55)
A177 G-d-P-p-a-mE-H (SEQ ID NO: 57)
A180 G-d-p-P-G-mE-H (SEQ ID NO: 63)
A181 p-d-P-P-G-mE-H (SEQ ID NO: 64)
A184 p-d-P-P-G-mE-h (SEQ ID NO: 65)
A185 P-pT-P-P-G-pS-H (SEQ ID NO: 21)
A186 G-d-P-P-G-mE (SEQ ID NO: 66)
A188 d-P-P-G-mE-H (SEQ ID NO: 67)
A189 P-P-G-mE-H (SEQ ID NO: 68)
A192 G-d-P-A-G-mE-K (SEQ ID NO: 69)
A193 G-d-P-a-G-mE-k (SEQ ID NO: 70)
A194 P-d-P-P-G-mE-K (SEQ ID NO: 71)
A195 P-d-P-P-G-mE-k (SEQ ID NO: 72)
A196 G-d-P-P-a-mE-k (SEQ ID NO: 73)
A197 a-d-P-P-a-mE-k (SEQ ID NO: 74)

As elsewhere in this specification, lower case letters represent D-amino acids.

Cell-Permeable Versions of Peptides 139 and 142 Up-Regulate DISC1 Expression

Peptides modified at the N-terminal amino group with stearate moieties to render them cell permeable (Severn Biotech Ltd) were dissolved in sterile DMSO at a stock concentration of 100 mM.

HEK293 cells were seeded into 6 well plates and cultured until 70-80% confluent. Cell permeable peptides 139 and 142 were added at 100 µM. Cells were incubated at 37° C./5% C02. Cells were taken at 0, 1, 2, 3 and 6 hours post peptide addition. After treatment cells were washed briefly with ice cold PBS and lysed on ice using 3T3 lysis buffer (20 mM Hepes (pH 7.4), 50 mM NaCl, 50 mM NaF, 10% (v/v) glycerol, 1% (w/v) Triton X-100, 10 mM EGTA, 30 mM sodium pyrophosphate) containing protease and phosphatase inhibitors. Protein concentrations were assessed using Bradford assay. Cell lysates were separated by SDS-PAGE and levels of DISC1 expression determined by quantitative Western blotting using the Licor Odyssey imaging system. GAPDH was used as a control to confirm equal loading.

Figure 9:
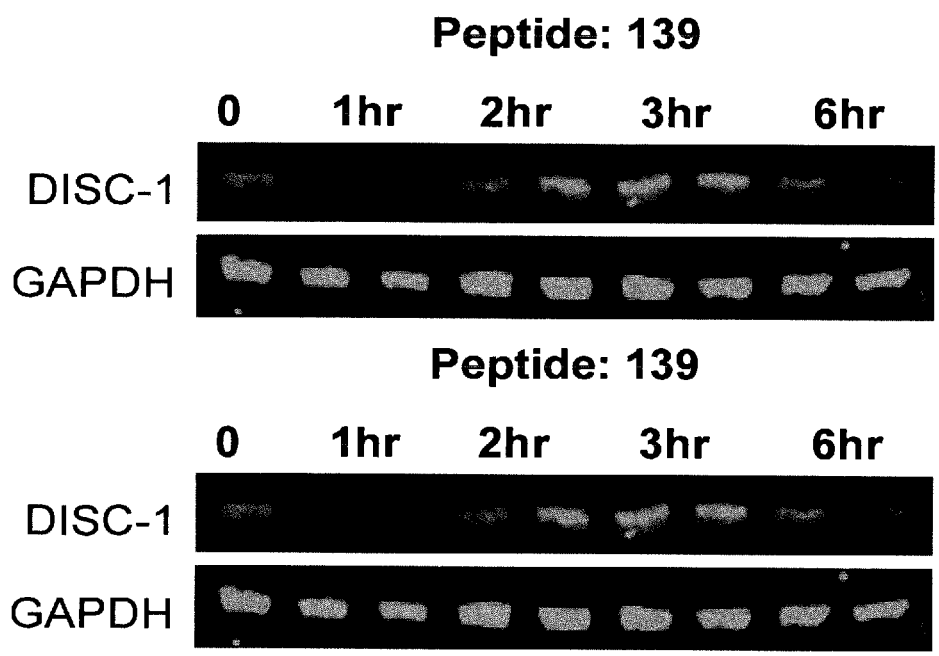
FIG. 9: DISC1 upregulation is time dependent.

FIG. 9 shows that DISC1 is upregulated in a time-dependent manner by these peptides.

In a similar experiment, HEK293 were seeded into 6 well plates and cultured until 70-80% confluent. Cell-permeable peptides 139 and 142 were added over a concentration range: 10 µM, 30 µM, 50 µM, 100 µM in duplicate. Cells were incubated at 37° C./5% C02 for 3 hours. Cells were taken at 0, 1, 2, 3 and 6 hours post peptide addition. After treatment cells were washed briefly with ice cold PBS and lysed on ice as described above.

Figure 10:
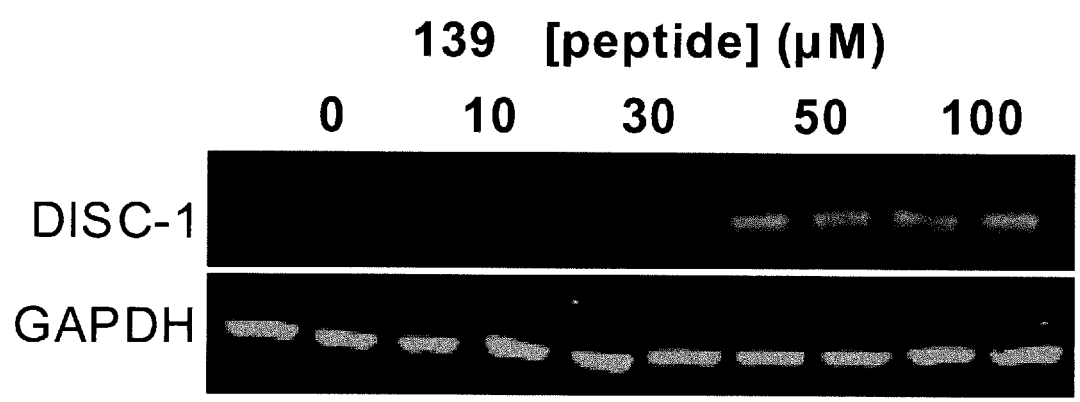
FIG. 10: DISC1 upregulation is dose dependent.

FIG. 10 shows that the effect of peptide 139 on DISC1 up-regulation is dose-dependent. Similar results were obtained for peptide 142 (data not shown). Conditions were as described for FIG. 9.

Figure 11:
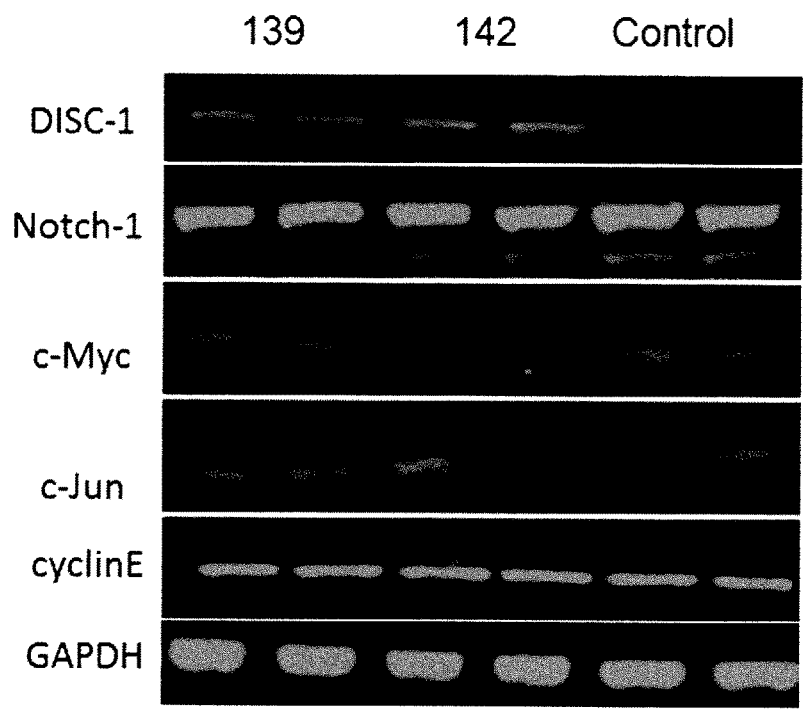
FIG. 11: Peptides 139 and 142 do not upregulate other FBXW7 substrates.

FIG. 11 shows that peptides 139 and 142 have no effect on expression levels of the other FBXW7 substrates Notch-1, c-Myc, c-Jun and cyclinE, thus demonstrating their specificity for the FBXW7-DISC1 interaction.

Co-Crystallisation of FBXW7-SKP1 and DISC1 Phospho-Degron Peptide

N-terminal His$_6$ (SEQ ID NO: 118) tagged human FBXW7 (residues 263-707) and truncated Skp1 (Schulman et al., 2000) were co-expressed as a dicistronic message in Escherichia coli. The Skp1-FBXW7 fusion protein was purified by Ni$^{2+}$-nitrilotriacetic acid (NTA) affinity chromatography followed by tobacco etch virus (TEV) protease cleavage of the His$_6$ tag (SEQ ID NO: 118), and by anion exchange and gel filtration chromatography. For crystallization, the Skp1-FBXW7 fusion was concentrated to 48 mg/ml by ultrafiltration in 20 mM HEPES-Na (pH 7.4), 200 mM NaCl and 5 mM dithiothreitol (DTT).

The Skp1-FBXW7-DISC1 complexes were prepared by mixing a 48 mg/ml solution of Skp1-FBXW7 with a 2-fold molar excess of DISC1 peptide (residues 193-207, phosphorylated at Thr198 and Ser202) in 25 mM Tris-HCl (pH 8.0), 200 mM NaCl, and 5 mM DTT. The Skp1-FBXW7-DISC1 peptide complex was crystallized from 100 mM HEPES-Na (pH 7.4) and 1.2 M Li$_2$SO$_4$ by the hanging-drop vapor diffusion method at 4° C. Crystals were flash-frozen in solutions containing saturated Li$_2$SO$_4$. Diffraction data were collected at the X29 beamline of the National Synchrotron Light Source (NSLS). Data were processed using the HKL2000 suite (Otwinowski and Minor, 1997). All crystals contain one complex in the asymmetric unit. The structures were determined by molecular replacement with the program MOLREP of the CCP4 suite (Vagin and Teplyakov, 2010) and the Skp1-FBXW7 structure (Hao et al., 2007) was used as the search model. The DISC1 peptide was built using $2F_o$-$F_c$ and $F_o$-$F_c$ maps with Coot (Emsley and Wowtan, 2004) and refined using REFMAC5 (Winn et al., 2003). Residues 204-207 of DISC1 are not visible in the electron density maps, and presumably disordered.

The structure suggests that the phosphate of the phospho-threonine residue at position 198 of DISC1 may make important contacts with the side chains of Arg205, Tyr519, Arg465 and Arg479 of FBXW7, while the phosphate of the phospho-serine at position 202 of DISC1 may make important contacts with Arg479, Thr463 and Ser462 of FBXW7. (Data not shown.)

Modelling suggests that, if the phospho-threonine and phospho-serine residues are replaced by other charged amino acids such as glutamic acid, the side chains may be capable of forming an intramolecular hydrogen bond with their respective backbone N-H groups, thus reducing their potential to interact with the relevant residues of FBXW7. (Not shown.) Modification of the peptide backbone to substitute the backbone nitrogen with a suitable group other than hydrogen may therefore increase the strength of interaction between an FBXW7-binding moiety and FBXW7.

Development of Fluorescence Polarisation (FP) Assay Between FBXW7-SKP1 Complex and DISC1 Phopshodegron Peptide A fluorescence polarisation assay has been developed to screen for compounds capable of disrupting the interaction between the DISC1 phopshodegron peptide and FBXW7 (and hence capable of disrupting the DISC1-FBXW7 interaction).

All peptides and compound stocks were made in DMSO. PBS+0.25% Tween20 was used as assay diluent.

5 µl of compound (to give a final concentration of 10 µM in the assay) in DMSO is added to well of a 384-well black, low-binding, round-bottomed plate and plates are read for background fluorescence.

5 µl of FBXW7/Skp1 protein complex (final concentration of 0.4 µM in well) and fluorescent (fluorescein-tagged) DISC1 phosphodegron peptides singly or doubly phosphorylated (Flu-VPPpTPPGSH (SEQ ID NO: 117) or Flu-VPPpTPPGpSH (SEQ ID NO: 117)) or Cyclin E (each at final concentration of 0.1 µM in well) in PBS+0.25% Tween20 is added to each well.

Fluorescence is determined by reading the plates in a Mithras plate-reader using the standard protocol for Fluorescence Polarisation determination.

Figure 12:
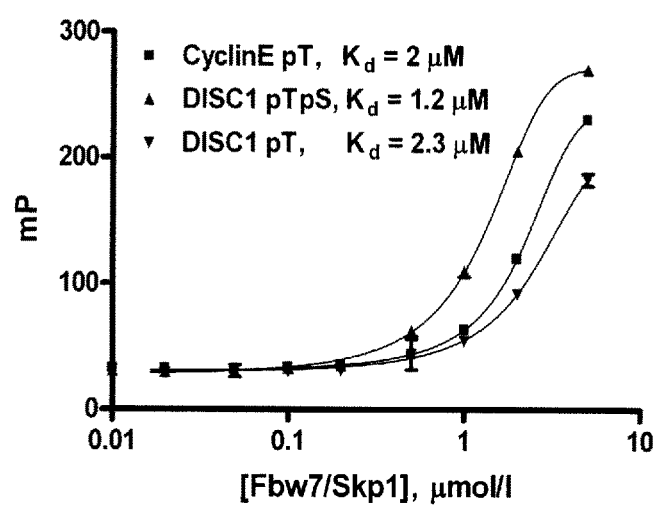
FIG. 12: FP assay between FBXW7-SKP1 complex and DISC1 phospho-degron peptides.

FIG. 12 shows that binding of each of the relevant test agents (Cyclin E and the two phospho-peptides) increases as the concentration of the relevant test agent increases.

Isothermal Titration Calorimetry (ITC)

Affinity of DISC1 analogue peptides (or other binding inhibitors) for FBXW7 may be determined using ITC.

Protein samples are typically dialysed against a solution containing 20 mM HEPES-Na (pH 7.4), 200 mM NaCl, and 2 mM β-mercaptoethanol before combining. Typically, the concentrations of Skp1-FBXW7 and DISC1 peptides used in the assay are 50 µM and 1 mM, respectively.

Titration is performed at 25° C. with a NANO ITC System (TA Instruments, New Castle, Del.) and data analysed using the TA Nano Analyze software. Dissociation constants and their standard deviations are typically derived from two to three independent measurements.

Using this method, the Kd of the doubly-phosphorylated test peptide VPPpTPPGpSH (SEQ ID NO: 119) has been determined to be approximately 1 µM, which is consistent with the determination made by fluoresence polarisation (shown in FIG. 12).

Supplemental Materials and Methods

HEK293 Cell Culture:

HEK (Human Embryonic Kidney)-293 cells were maintained in DMEM (Dulbecco's modified Eagle's medium) supplemented with 2 mM glutamine, 10% (v/v) fetal bovine serum (Sigma), 1% penicillin/streptomycin (100 units/ml) (Sigma) in an atmospheric chamber of 5% C02 and 37° C.

Western Blot

Western blotting was performed using the Novex® protein separation system and reagents (Invitrogen) according to manufacturer's instructions.

Lysates were boiled in Laemmli buffer for 2 minutes prior to SDS-PAGE. Lysates were loaded on to a precast 4-12% bis-tris gel (~10 µg/well). Gels were resolved at 150V (constant) for 90 mins. Proteins were transferred to nitrocellulose membrane at 30V for 1 hour. Membranes were blocked in 5% Milk in 1×TBS-tween20 for 1 hour at room temperature. Primary antibodies were diluted in 1% milk in 1×TBS-tween20 and incubated overnight at 4° C. Membranes were washed three times with 1×TBS-tween20 and the appropriate secondary antibody (diluted using 1% milk in 1×TBS-tween20) was added for 45 mins at room temperature. Membranes were washed a further three times with 1×TBS-tween20 and once in 1×TBS. Protein bands were visulised using the Licor Odyssey scanner and analysed using Odyssey software (version 1.2). DISC-1 protein levels were analysed by densitometry and normalised against those of the loading control (GAPDH).

Antibodies

The following antibodies were used for western blotting.

Primary antibodies: anti-human DISC-1 (α DISC-1) (Dr K Millar/Prof A Sawa) (1/4000), c-myc (Santa Cruz, sc-40) (1/1000), c-Jun (Santa Cruz, sc-1694) (1/1000), cyclinE (Abcam, ab7959) (1/1000), GAPDH (Abcam, ab8245) (1/5000), notch-1 (Abcam, ab52627) (1/1000), HA (Santa Cruz, sc-7392) (1/2000), FLAG (HRP-conjugated; SIGMA, A8592) (1/10000), VSV (SIGMA, V5507) (1/5000).

Secondary Antibodies: IRDye 800CW Donkey anti-Rabbit IgG (926-32213) and IRDye 800CW Goat anti-Mouse IgG (926-32210) (1/10,000).

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, including patent documents, disclosed herein are incorporated by reference in their entirety for all purposes, particularly for the disclosure referenced herein.

REFERENCES

1. Owen, M. J. Schizophr Bull, 2012. 38(5): p. 904-7.
2. Brandon, N. J. and A. Sawa, Nat Rev Neurosci, 2011. 12(12): p. 707-22.
3. Porteous, D. J., et al., Trends Mol Med, 2011. 17(12): p. 699-706.
4. Kamiya, A., T. W. Sedlak, and M. V. Pletnikov, Front Psychiatry, 2012. 3: p. 25.
5. Blackwood, D. H., et al., Am J Hum Genet, 2001. 69(2): p. 428-33.
6. Camargo, L. M., et al. Mol Psychiatry, 2007. 12(1): p. 74-86.
7. Millar, J. K., et al., Science, 2005. 310(5751): p. 1187-91.
8. Eykelenboom, J. E., et al., Hum Mol Genet, 2012. 21(15): p. 3374-86.
9. Williams, J. M., et al., Am J Med Genet A, 2009. 149A(8): p. 1758-62.
10. Crepel, A., et al., Clin Genet, 2010. 77(4): p. 389-94.
11. Jaaro-Peled, H., Prog Brain Res, 2009. 179: p. 75-86.
12. Bradshaw, N. J., et al., J Neurosci, 2011. 31(24): p. 9043-54.
13. Ishizuka, K., et al., Nature, 2011. 473(7345): p. 92-6.
14. Schurov, I. L., et al., Mol Psychiatry, 2004. 9(12): p. 1100-10.
15. Cajigas, I. J., T. Will, and E. M. Schuman, EMBO J, 2010. 29(16): p. 2746-52.
16. Tai, H. C. and E. M. Schuman, Nat Rev Neurosci, 2008. 9(11): p. 826-38.
17. Hao, B., et al., Mol Cell, 2007. 26(1): p. 131-43.
18. Shi, G., et al., Traffic, 2012. 13(7): p. 914-25.
19. Bodor, D. L., et al., Curr Protoc Cell Biol, 2012. Chapter 8
20. Hannoun, Z., et al., Toxicology. 278(3): p. 288-93.
21. Carlyle, B. C., et al., Mol Psychiatry. 16(7): p. 693-4.
    Emsley, P., and Cowtan, K. (2004). Coot: model-building tools for molecular graphics. Acta crystallographica 60, 2126-2132.
    Hao, B., Oehlmann, S., Sowa, M. E., Harper, J. W., and Pavletich, N. P. (2007). Structure of a FBXW7-Skp1-cyclin E complex: multisite-phosphorylated substrate recognition by SCF ubiquitin ligases. Mol Cell 26, 131-143.
    Otwinowski, Z., and Minor, W. (1997). Processing of X-ray diffraction data collected in oscillation mode. Methods Enzymol. 276, 307-326.
    Schulman, B. A., Carrano, A. C., Jeffrey, P. D., Bowen, Z., Kinnucan, E. R., Finnin, M. S., Elledge, S. J., Harper, J. W., Pagano, M., and Pavletich, N. P. (2000). Insights into SCF ubiquitin ligases from the structure of the Skp1-Skp2 complex. Nature 408, 381-386.
    Vagin, A., and Teplyakov, A. (2010). Molecular replacement with MOLREP. Acta crystallographica 66, 22-25.
    Winn, M. D., Murshudov, G. N., and Papiz, M. Z. (2003). Macromolecular TLS refinement in REFMAC at moderate resolutions. Methods in enzymology 374, 300-321.

The invention claimed is:

1. A method for increasing the level of DISC1 (Disrupted in schizophrenia-1 protein) in a subject with schizophrenia or bipolar disorder in which DISC1 levels are decreased, comprising administering to the subject an antagonist capable of inhibiting binding between DISC1 and FBXW7 (F-box/WD repeat-containing protein 7) and comprising a protein component having a maximum length of 25 amino acids, said protein component comprising an FBXW7-binding moiety capable of binding to FBXW7 and inhibiting DISC1 binding to FBXW7, wherein the FBXW7-binding moiety comprises a core sequence having the sequence G-mE-P-P-G-mE-H (SEQ ID NO: 6), wherein mE represents N-methyl glutamic acid, and wherein said core sequence binds to FBXW7.

2. The method of claim 1 wherein the FBXW7-binding moiety has a maximum length of 7, 8, 9, 10, 15 or 20 amino acids.

3. The method of claim 1 wherein the antagonist further comprises a heterologous component selected from a polyethylene glycol (PEG), poly-sialic acid, fatty or lipid moiety;

an immunoglobulin Fc region;

an albumin;

a cell penetrating peptide (CPP) or peptide transduction domain (PTD); and hexamethylenediamine (HMD), putrescine, spermine, spermidine or protamine;

wherein the cell penetrating peptide (CPP) or peptide transduction domain is Penetratin (43-58) (SEQ ID NO: 75), Amphipathic model peptide (SEQ ID NO: 76), Transportan (SEQ ID NO: 77), signal sequence-based peptide (SBP) (SEQ ID NO: 78), fusion sequence-based peptide (FBP) (SEQ ID NO: 79), HIV Tat peptide (48-60) (SEQ ID NO: 80), Syn-B1(SEQ ID NO: 81), Syn-B3 (SEQ ID NO: 82), (Arg)7 (SEQ ID NO: 83) or (Arg)9 (SEQ ID NO: 84).

4. The method of claim 3 wherein the fatty or lipid moiety is a cholesterol or stearoyl moiety.

* * * * *